(12) United States Patent
Robertson et al.

(10) Patent No.: US 7,094,532 B2
(45) Date of Patent: Aug. 22, 2006

(54) GENETIC MUTATION UNDERLYING ORTHOSTATIC INTOLERANCE AND DIAGNOSTIC AND THERAPEUTIC METHODS RELATING THERETO

(75) Inventors: David Robertson, Nashville, TN (US); Randy D. Blakely, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 376 days.

(21) Appl. No.: 09/750,609

(22) Filed: Dec. 28, 2000

(65) Prior Publication Data

US 2003/0170875 A1    Sep. 11, 2003

Related U.S. Application Data

(60) Provisional application No. 60/175,456, filed on Jan. 11, 2000, provisional application No. 60/173,682, filed on Dec. 29, 1999.

(51) Int. Cl.
- C12Q 1/68 (2006.01)
- C12P 19/34 (2006.01)
- C07H 21/04 (2006.01)
- C07K 1/00 (2006.01)

(52) U.S. Cl. ............... 435/6; 435/91.2; 536/24.33; 530/350

(58) Field of Classification Search ............ 435/6, 435/91.2; 536/24.33; 530/350
See application file for complete search history.

(56) References Cited

U.S. PATENT DOCUMENTS

5,580,775 A    12/1996    Fremeau, Jr. et al.
5,763,183 A *  6/1998    Pesonen et al. ............... 435/6
6,248,526 B1 * 6/2001    Weimer ......................... 435/6

FOREIGN PATENT DOCUMENTS

WO    WO 92/17568    10/1992

OTHER PUBLICATIONS

Jonsson et al. Polymorphisms in the dopamine, serotinin and norepinephrine transporter genes and their relationships to monoamine metabolite concentrations in CSF of healthy volunteers. Pscychiatry Res., vol. 79, pp. 1-9, 1998.*
Flattem et al.Identification of a coding mutation in the norepinephrine transporter gene which predisposes a family to orthosattic intolerance. Am. J Human Genetics, vol. 65, No. 4, p. A43, 1999.*
Jacob et al. Abnormal norepinephrine clearance and adrenergic receptor sensitivity in idiopathic orthostatic intolerance. Circulation, vol.. 99, No. 13, pp. 1706-1712, 1999.*
Jonsson et al. Polymorphisms in the dopamine, serotinin and norepinephrine transporter genes and their relationships to monoamine metabolite concentrations in CSF of healthy volunteers. Pscychiatry Res., vol. 79, pp. 1-9, 1998.*
Jacob et al. Abnormal norepinephrine clearance and adrenergic receptor sensitivity in idiopathic orthostatic intolerance. Circulation, vol.. 99, No. 13, pp. 1706-1712, 1999.*
Stober et al. Systemic search for variation in the human norepinephrine transporter gene: Indentification of five naturally occurring missense mutations and study of association with major psychiatric disorders. Am J Med Genet., vol. 67, pp. 523-553 1996.*
Flattem et al., "Identification of a Coding Mutation in the Norepinephrine Transporter Gene WHich Predisposes a Family to Orthostatic Intolerance," Am. J. Human Genet., vol. 65 (No. 4), p. A43, (1999).
Shannon, "Functional Polymorphism of the Norepinephrine Transporter (NET) Presenting as Mitral Valve Prolapse and Orthostatic Intolerance," Circulation, vol. 110 (No. 18), p. I.195, (Nov. 2, 1999).
Owen et al., "Norepinephrine Transporter Gene Polymorphism is not Associated with Susceptibility to Major Depression," Psychiatry Research, vol. 87 (No. 1), p. 1-5, (1999).
Pacholczyk et al., "Expression Cloning of a Cocaine and Antidepressant-Sensitive Human Noradrenaline Transporter," Bio Nature, p. 350-353, (Mar. 28, 1991).
Porzgen et al., "Molecular Cloning and Organization of the Coding region of the Human Norepinephrine Transporter Gene," Biochem. Biophys. Res. Commun., vol. 215 (No. 3), p. 1145-1150, (Oct. 24, 1995).
Wang et al., "Genetic Approaches to Studying Norepinephrine Function: Knockout of the Mouse Norepinephrine Transporter," Gene Biol. Psychiatry, p. 1124-1130, (1999).
Anonymous, "Gene Characterization Kits," In: Stratagene Catalog, p. 39, (1988).
PCT International Search Report for PCT International Application No. PCT/US00/35491.
Jordan et al., "Contrasting Actions of Pressor Agents in Severe Autonomic Failure," Am. J. Med., vol. 105 (No. 2), p. 116-124, (1998), (Abstract only).
Choy et al., "Abnormalities of the QT Intercal in Primary Disorder of Autonomic Failure," Am. Heart J., vol. 136 (No. 4), p. 664-671, (1998). (Abstract only).
Jordan et al., "Contrasting Effects of Vasodilators on Blood Pressure and Sodium Balance in the Hypertension of Autonomic Failure," J. Am. Soc. Nephrol., vol. 10 (No. 1), p. 35-42, (1999). (Abstract only).

(Continued)

*Primary Examiner*—Suryaprabha Chunduru
(74) *Attorney, Agent, or Firm*—Jenkins, Wilson, Taylor & Hunt, P.A.

(57) ABSTRACT

Isolated polynucleotide molecules and peptides encoded by these molecules are used in the analysis of human norepinephrine (NE) transporter variants, as well as in diagnostic and therapeutic applications, relating to a human NE transporter polymorphism. By analyzing genomic DNA or amplified genomic DNA, or amplified cDNA derived from mRNA, it is possible to type a human NE transporter with regard to the human NE transporter polymorphism, for example, in the context of diagnosing and treating NE transport impairments, and disorders associated with NE transport impairments, such as orthostatic intolerance.

14 Claims, 4 Drawing Sheets

OTHER PUBLICATIONS

Jacob et al., "Effects of Standing on Cerebrovascular Resistance in patients with Idiopathic Orthostatic Intolerance," Am. J. Med., vol. 106 (No. 1), p. 59-64, (1999). (Abstract only).

Gilman et al., "Consensus Statement on the Diagnosis of Multiple System Atrophy," J. Neurol. Sci., vol. 163 (No. 1), p. 94-98, (Feb. 1, 1999). (Abstract only).

Shannon et al., "Acute Effect of Ephedrine on 24-h Energy Balance," Clin. Sci. (Colch), vol. 96 (No. 5), p. 483-491, (1999). (Abstract only).

Jacob et al., "Abnormal norepinephrine Clearance and Adrenergic Receptor Seneiticity in Idiopathic Orthostatic Intolerance," Circulation, vol. 99 (No. 13), p. 1706-1712, (Apr. 6, 1999), (Abstract only).

Robertson et al., "Neurally Mediated Syncope: Pthophysiology and IMplications for Treatment," Am. J. Med. Sci., vol. 317 (No. 2), p. 102-109, (1999). (Abstract only).

Austin et al., "Multiple System Atrophy: Clinical Presentation and Diagnosis," Tenn. Med., vol. 92 (No. 2), p. 55-57, (1999). (Abstract only).

Furlan et al., "Chronic Orthostatic Intolerance: a Disorder with Doscordant Cardiac and Vascular Sympathetic Control," Circulation, vol. 98 (No. 20), p. 2154-2159, (Nov. 17, 1998). (Abstract only).

Robertson, "Distribution and Observed Associations of Orthostatic Blood Pressure Changes in Elderly General Medicine Outpatients," Am. J. Med. Si., vol. 315 (No. 5), p. 287-295, (1998). (Abstract only).

Caswell, "Orthostatic Intolerance," NASA West Virginia Space Grant Consortium, (1997).

"Chronic Orthostatic Intolerance (COI) Nerve Abnormality," Causes Disabling Rapid Heart Rate, Dizziness, Dallas, Texas, (Nov. 17, 1998).

National Dysautonomia Research Foundation, "Orthostatic Intolerance Syndromes," (1997).

Stöber et al., Systematic Search for Variation in the Human Norepinephrine Transporter Gene: Identification of Five Naturally Occurring Missense Mutations and Study of Association with Major Psychiatric Disorders, *Am. J. of Medical Genetics* (*Neuropsychiatric Genetics*) 67:523-532 (1996).

* cited by examiner

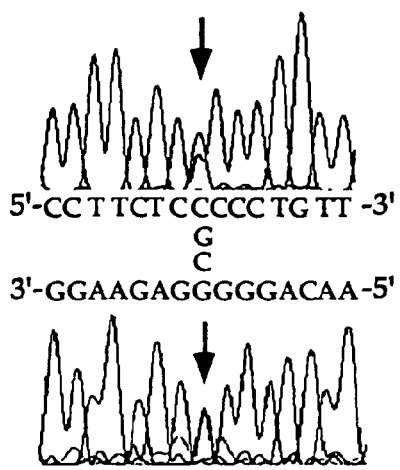
FIG. 2A
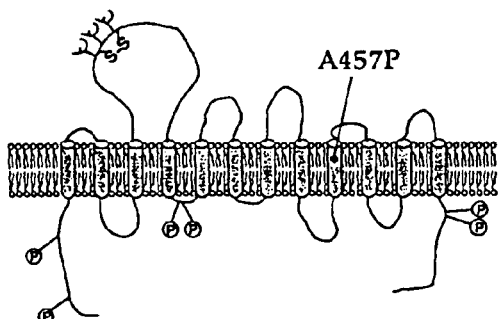
FIG. 2B
TMD 9 *
hNET  LFTFGVTFSTFLLALFCIT
mNET  LFTCVVTIISTFLLALFCIT
bNET  LFTFAVSFGTFLLALFCIT
fET   AFTFAVAFITFLLALLCIT
FIG. 2C
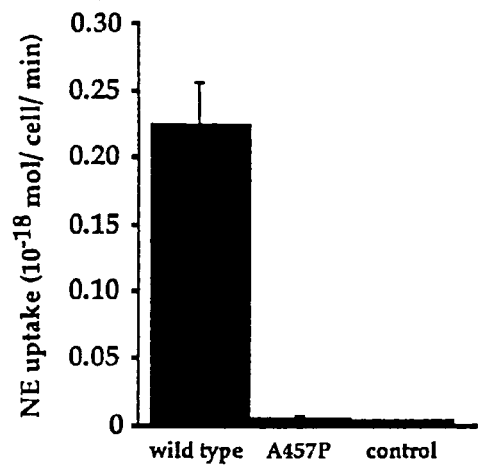
FIG. 2D
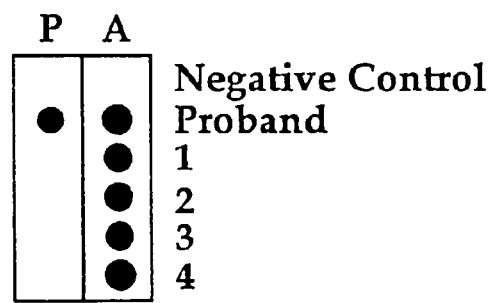
FIG. 2E
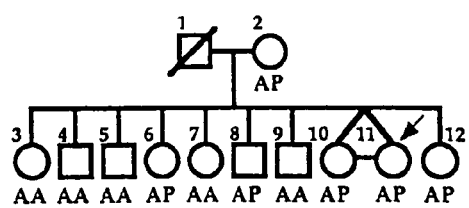
FIG. 2F

SEQUENCE LISTING

<160> NUMBER OF SEQ ID NOS: 40

<210> SEQ ID NO 1
<211> LENGTH: 1854
<212> TYPE: DNA
<213> ORGANISM: Homo sapiens
<220> FEATURE:
<221> NAME/KEY: CDS
<222> LOCATION: (1)..(1851)
<300> PUBLICATION INFORMATION:

```
<301> AUTHORS: Porzgen, P.
      Bonisch, H.
      Bruss, M.
<302> TITLE: Molecular Cloning and Organization of the Coding Region
      of the Human Norepinephrine Tranporter Gene
<303> JOURNAL: Biochem. Biophys. Res. Commun.
<304> VOLUME: 215
<305> ISSUE: (3)
<306> PAGES: 1145-1150
<307> DATE: 1995-10-24
<308> DATABASE ACCESSION NUMBER: x91117
<309> DATABASE ENTRY DATE: 1996-02-20

<400> SEQUENCE: 1 atg ctt ctg gcg cgg atg aac ccg cag gtg cag ccc gag aac aac ggg       48
Met Leu Leu Ala Arg Met Asn Pro Gln Val Gln Pro Glu Asn Asn Gly
 1               5                  10                  15 gcg gac acg ggt cca gag cag ccc ctt cgg gcg cgc aaa act gcg gag       96
Ala Asp Thr Gly Pro Glu Gln Pro Leu Arg Ala Arg Lys Thr Ala Glu
             20                  25                  30 ctg ctg gtg gtg aag gag cgc aac ggc gtc cag tgc ctg ctg gcg ccc      144
Leu Leu Val Val Lys Glu Arg Asn Gly Val Gln Cys Leu Leu Ala Pro
         35                  40                  45 cgc gac ggc gac gcg cag ccc cgg gag acc tgg ggc aag aag atc gac      192
Arg Asp Gly Asp Ala Gln Pro Arg Glu Thr Trp Gly Lys Lys Ile Asp
     50                  55                  60 ttc ctg ctg tcc gta gtc ggc ttc gca gtg gac ctg gcc aac gtg tgg      240
Phe Leu Leu Ser Val Val Gly Phe Ala Val Asp Leu Ala Asn Val Trp
 65                  70                  75                  80 cgc ttc ccc tac ctc tgc tac aag aac ggc ggc ggt gcc ttc ttg atc      288
Arg Phe Pro Tyr Leu Cys Tyr Lys Asn Gly Gly Gly Ala Phe Leu Ile
                 85                  90                  95 ccg tac aca ctg ttc ctt atc atc gcg ggg atg ccc ctg ttc tac atg      336
Pro Tyr Thr Leu Phe Leu Ile Ile Ala Gly Met Pro Leu Phe Tyr Met
            100                 105                 110 gag ctg gct ctg gga cag tac aac cgg gag ggg gct gcc acc gtt tgg      384
Glu Leu Ala Leu Gly Gln Tyr Asn Arg Glu Gly Ala Ala Thr Val Trp
        115                 120                 125 aaa atc tgc cca ttc ttc aaa ggc gtt ggc tat gct gtc atc ctg atc      432
Lys Ile Cys Pro Phe Phe Lys Gly Val Gly Tyr Ala Val Ile Leu Ile
    130                 135                 140 gcc ctg tac gtt ggc ttc tac tac aac gtc atc atc gcc tgg tca ctc      480
Ala Leu Tyr Val Gly Phe Tyr Tyr Asn Val Ile Ile Ala Trp Ser Leu
145                 150                 155                 160 tac tac ctc ttc tcc tcc ttc acc ctc aac ctg ccc tgg acc gac tgt      528
Tyr Tyr Leu Phe Ser Ser Phe Thr Leu Asn Leu Pro Trp Thr Asp Cys
                165                 170                 175 ggc cac acc tgg aac agc ccc aac tgt acc gac ccc aag ctc ctc aat      576
Gly His Thr Trp Asn Ser Pro Asn Cys Thr Asp Pro Lys Leu Leu Asn
            180                 185                 190 ggc tcc gtg ctt ggc aac cac acc aag tac tcc aag tac aag ttc acg      624
Gly Ser Val Leu Gly Asn His Thr Lys Tyr Ser Lys Tyr Lys Phe Thr
        195                 200                 205 ccg gca gcc gag ttt tat gag cgt ggt gtc ctg cac ctt cac gag agc      672
Pro Ala Ala Glu Phe Tyr Glu Arg Gly Val Leu His Leu His Glu Ser
    210                 215                 220 agc ggg att cat gac atc ggc ctg ccc cag tgg cag ctc ttg ctc tgt      720
Ser Gly Ile His Asp Ile Gly Leu Pro Gln Trp Gln Leu Leu Leu Cys
225                 230                 235                 240 ctg atg gtc gtc gtc atc gtc ttg tat ttt agc ctc tgg aaa ggg gtg      768
Leu Met Val Val Val Ile Val Leu Tyr Phe Ser Leu Trp Lys Gly Val
                245                 250                 255
```

-continued

```
aag aca tca gga aag gtg gtg tgg atc aca gcc acg ctg cct tac ttc    816
Lys Thr Ser Gly Lys Val Val Trp Ile Thr Ala Thr Leu Pro Tyr Phe
        260                 265                 270 gtg ctg ttc gtg ctc ctg gtc cat ggc gtc acg ctg ccc gga gcc tcc    864
Val Leu Phe Val Leu Leu Val His Gly Val Thr Leu Pro Gly Ala Ser
            275                 280                 285 aat ggc atc aat gcc tac ctg cac atc gac ttc tac cgc ttg aaa gag    912
Asn Gly Ile Asn Ala Tyr Leu His Ile Asp Phe Tyr Arg Leu Lys Glu
    290                 295                 300 gcc acg gta tgg att gat gcc gca act cag ata ttt ttt tcc ttg ggg    960
Ala Thr Val Trp Ile Asp Ala Ala Thr Gln Ile Phe Phe Ser Leu Gly
305                 310                 315                 320 gct gga ttt gga gta ttg att gca ttt gcc agt tac aac aaa ttt gac   1008
Ala Gly Phe Gly Val Leu Ile Ala Phe Ala Ser Tyr Asn Lys Phe Asp
                325                 330                 335 aac aac tgt tac agg gat gcc ctg ctg acc agc agc atc aac tgt atc   1056
Asn Asn Cys Tyr Arg Asp Ala Leu Leu Thr Ser Ser Ile Asn Cys Ile
        340                 345                 350 acc agc ttc gtc tct ggg ttc gcc atc ttc tcc atc ctt ggt tac atg   1104
Thr Ser Phe Val Ser Gly Phe Ala Ile Phe Ser Ile Leu Gly Tyr Met
            355                 360                 365 gcc cat gaa cac aag gtc aac att gag gat gtg gcc aca gaa gga gct   1152
Ala His Glu His Lys Val Asn Ile Glu Asp Val Ala Thr Glu Gly Ala
    370                 375                 380 ggc cta gtg ttc atc ctg tat cca gag gcc att tct acc ctg tct gga   1200
Gly Leu Val Phe Ile Leu Tyr Pro Glu Ala Ile Ser Thr Leu Ser Gly
385                 390                 395                 400 tct aca ttc tgg gct gtt gtg ttt ttc gtc atg ctc ctg gcg ctg ggc   1248
Ser Thr Phe Trp Ala Val Val Phe Phe Val Met Leu Leu Ala Leu Gly
                405                 410                 415 ctt gac agc tca atg gga ggc atg gag gct gtc atc acg ggc ctg gca   1296
Leu Asp Ser Ser Met Gly Gly Met Glu Ala Val Ile Thr Gly Leu Ala
        420                 425                 430 gat gac ttc cag gtc ctg aag cga cac cgg aaa ctc ttc aca ttt ggc   1344
Asp Asp Phe Gln Val Leu Lys Arg His Arg Lys Leu Phe Thr Phe Gly
            435                 440                 445 gtc acc ttc agc act ttc ctt ctc gcc ctg ttc tgc ata acc aag ggt   1392
Val Thr Phe Ser Thr Phe Leu Leu Ala Leu Phe Cys Ile Thr Lys Gly
    450                 455                 460 gga att tac gtc ttg acc ctc ctg gac acc ttt gct gcg ggc acc tcc   1440
Gly Ile Tyr Val Leu Thr Leu Leu Asp Thr Phe Ala Ala Gly Thr Ser
465                 470                 475                 480 atc ctt ttt gct gtc ctc atg gaa gcc atc gga gtt tcc tgg ttt tat   1488
Ile Leu Phe Ala Val Leu Met Glu Ala Ile Gly Val Ser Trp Phe Tyr
                485                 490                 495 gga gtg gac agg ttc agc aac gac atc cag cag atg atg ggg ttc agg   1536
Gly Val Asp Arg Phe Ser Asn Asp Ile Gln Gln Met Met Gly Phe Arg
        500                 505                 510 ccg ggt cta tac tgg aga ctg tgc tgg aag ttc gtc agt cct gcc ttc   1584
Pro Gly Leu Tyr Trp Arg Leu Cys Trp Lys Phe Val Ser Pro Ala Phe
            515                 520                 525 ctc ctg ttc gtg gtt gtg gtc agc atc atc aac ttc aag cca ctc acc   1632
Leu Leu Phe Val Val Val Ser Ile Ile Asn Phe Lys Pro Leu Thr
    530                 535                 540 tac gac gac tac atc ttc ccg ccc tgg gcc aac tgg gtg ggg tgg ggc   1680
Tyr Asp Asp Tyr Ile Phe Pro Pro Trp Ala Asn Trp Val Gly Trp Gly
545                 550                 555                 560 atc gcc ctg tcc tcc atg gtc ctg gtg ccc atc tac gtc atc tat aag   1728
Ile Ala Leu Ser Ser Met Val Leu Val Pro Ile Tyr Val Ile Tyr Lys
                565                 570                 575
```

```
ttc ctc agc acg cag ggc tct ctt tgg gag aga ctg gcc tat ggc atc      1776
Phe Leu Ser Thr Gln Gly Ser Leu Trp Glu Arg Leu Ala Tyr Gly Ile
        580                 585                 590 acg cca gag aac gag cac cac ctg gtg gct cag agg gac atc aga cag      1824
Thr Pro Glu Asn Glu His His Leu Val Ala Gln Arg Asp Ile Arg Gln
    595                 600                 605 ttc cag ttg caa cac tgg ctg gcc atc tga                              1854
Phe Gln Leu Gln His Trp Leu Ala Ile
    610                 615

<210> SEQ ID NO 2
<211> LENGTH: 617
<212> TYPE: PRT
<213> ORGANISM: Homo sapiens

<400> SEQUENCE: 2
```

| Met | Leu | Leu | Ala | Arg | Met | Asn | Pro | Gln | Val | Gln | Pro | Glu | Asn | Asn | Gly |
|---|---|---|---|---|---|---|---|---|---|---|---|---|---|---|---|
| 1 | | | | 5 | | | | | 10 | | | | | 15 | |

| Ala | Asp | Thr | Gly | Pro | Glu | Gln | Pro | Leu | Arg | Ala | Arg | Lys | Thr | Ala | Glu |
|---|---|---|---|---|---|---|---|---|---|---|---|---|---|---|---|
| | | | 20 | | | | | 25 | | | | | 30 | | |

| Leu | Leu | Val | Val | Lys | Glu | Arg | Asn | Gly | Val | Gln | Cys | Leu | Leu | Ala | Pro |
|---|---|---|---|---|---|---|---|---|---|---|---|---|---|---|---|
| | | | | 35 | | | | | 40 | | | | | 45 | |

| Arg | Asp | Gly | Asp | Ala | Gln | Pro | Arg | Glu | Thr | Trp | Gly | Lys | Lys | Ile | Asp |
|---|---|---|---|---|---|---|---|---|---|---|---|---|---|---|---|
| | 50 | | | | | 55 | | | | | 60 | | | | |

| Phe | Leu | Leu | Ser | Val | Val | Gly | Phe | Ala | Val | Asp | Leu | Ala | Asn | Val | Trp |
|---|---|---|---|---|---|---|---|---|---|---|---|---|---|---|---|
| 65 | | | | | 70 | | | | | 75 | | | | | 80 |

| Arg | Phe | Pro | Tyr | Leu | Cys | Tyr | Lys | Asn | Gly | Gly | Ala | Phe | Leu | Ile |
|---|---|---|---|---|---|---|---|---|---|---|---|---|---|---|
| | | | | 85 | | | | | 90 | | | | | 95 |

| Pro | Tyr | Thr | Leu | Phe | Leu | Ile | Ile | Ala | Gly | Met | Pro | Leu | Phe | Tyr | Met |
|---|---|---|---|---|---|---|---|---|---|---|---|---|---|---|---|
| | | | 100 | | | | | 105 | | | | | 110 | | |

| Glu | Leu | Ala | Leu | Gly | Gln | Tyr | Asn | Arg | Glu | Gly | Ala | Ala | Thr | Val | Trp |
|---|---|---|---|---|---|---|---|---|---|---|---|---|---|---|---|
| | | | | 115 | | | | | 120 | | | | | 125 | |

| Lys | Ile | Cys | Pro | Phe | Phe | Lys | Gly | Val | Gly | Tyr | Ala | Val | Ile | Leu | Ile |
|---|---|---|---|---|---|---|---|---|---|---|---|---|---|---|---|
| | 130 | | | | | 135 | | | | | 140 | | | | |

| Ala | Leu | Tyr | Val | Gly | Phe | Tyr | Tyr | Asn | Val | Ile | Ile | Ala | Trp | Ser | Leu |
|---|---|---|---|---|---|---|---|---|---|---|---|---|---|---|---|
| 145 | | | | | 150 | | | | | 155 | | | | | 160 |

| Tyr | Tyr | Leu | Phe | Ser | Ser | Phe | Thr | Leu | Asn | Leu | Pro | Trp | Thr | Asp | Cys |
|---|---|---|---|---|---|---|---|---|---|---|---|---|---|---|---|
| | | | | 165 | | | | | 170 | | | | | 175 | |

| Gly | His | Thr | Trp | Asn | Ser | Pro | Asn | Cys | Thr | Asp | Pro | Lys | Leu | Leu | Asn |
|---|---|---|---|---|---|---|---|---|---|---|---|---|---|---|---|
| | | | 180 | | | | | 185 | | | | | 190 | | |

| Gly | Ser | Val | Leu | Gly | Asn | His | Thr | Lys | Tyr | Ser | Lys | Tyr | Lys | Phe | Thr |
|---|---|---|---|---|---|---|---|---|---|---|---|---|---|---|---|
| | | | | 195 | | | | | 200 | | | | | 205 | |

| Pro | Ala | Ala | Glu | Phe | Tyr | Glu | Arg | Gly | Val | Leu | His | Leu | His | Glu | Ser |
|---|---|---|---|---|---|---|---|---|---|---|---|---|---|---|---|
| | 210 | | | | | 215 | | | | | 220 | | | | |

| Ser | Gly | Ile | His | Asp | Ile | Gly | Leu | Pro | Gln | Trp | Gln | Leu | Leu | Cys |
|---|---|---|---|---|---|---|---|---|---|---|---|---|---|---|
| 225 | | | | | 230 | | | | | 235 | | | | | 240 |

| Leu | Met | Val | Val | Ile | Val | Leu | Tyr | Phe | Ser | Leu | Trp | Lys | Gly | Val |
|---|---|---|---|---|---|---|---|---|---|---|---|---|---|---|
| | | | | 245 | | | | | 250 | | | | | 255 |

| Lys | Thr | Ser | Gly | Lys | Val | Val | Trp | Ile | Thr | Ala | Thr | Leu | Pro | Tyr | Phe |
|---|---|---|---|---|---|---|---|---|---|---|---|---|---|---|---|
| | | | 260 | | | | | 265 | | | | | 270 | | |

| Val | Leu | Phe | Val | Leu | Leu | Val | His | Gly | Val | Thr | Leu | Pro | Gly | Ala | Ser |
|---|---|---|---|---|---|---|---|---|---|---|---|---|---|---|---|
| | | | 275 | | | | | 280 | | | | | 285 | | |

| Asn | Gly | Ile | Asn | Ala | Tyr | Leu | His | Ile | Asp | Phe | Tyr | Arg | Leu | Lys | Glu |
|---|---|---|---|---|---|---|---|---|---|---|---|---|---|---|---|
| | 290 | | | | | 295 | | | | | 300 | | | | |

| Ala | Thr | Val | Trp | Ile | Asp | Ala | Ala | Thr | Gln | Ile | Phe | Phe | Ser | Leu | Gly |

-continued

```
            305                 310                 315                 320
        Ala Gly Phe Gly Val Leu Ile Ala Phe Ala Ser Tyr Asn Lys Phe Asp
                        325                 330                 335

Asn Asn Cys Tyr Arg Asp Ala Leu Leu Thr Ser Ser Ile Asn Cys Ile
                        340                 345                 350

Thr Ser Phe Val Ser Gly Phe Ala Ile Phe Ser Ile Leu Gly Tyr Met
                        355                 360                 365

Ala His Glu His Lys Val Asn Ile Glu Asp Val Ala Thr Glu Gly Ala
                370                 375                 380

Gly Leu Val Phe Ile Leu Tyr Pro Glu Ala Ile Ser Thr Leu Ser Gly
        385                 390                 395                 400

Ser Thr Phe Trp Ala Val Val Phe Phe Val Met Leu Leu Ala Leu Gly
                        405                 410                 415

Leu Asp Ser Ser Met Gly Gly Met Glu Ala Val Ile Thr Gly Leu Ala
                        420                 425                 430

Asp Asp Phe Gln Val Leu Lys Arg His Arg Lys Leu Phe Thr Phe Gly
                        435                 440                 445

Val Thr Phe Ser Thr Phe Leu Leu Ala Leu Phe Cys Ile Thr Lys Gly
        450                 455                 460

Gly Ile Tyr Val Leu Thr Leu Leu Asp Thr Phe Ala Ala Gly Thr Ser
        465                 470                 475                 480

Ile Leu Phe Ala Val Leu Met Glu Ala Ile Gly Val Ser Trp Phe Tyr
                        485                 490                 495

Gly Val Asp Arg Phe Ser Asn Asp Ile Gln Gln Met Met Gly Phe Arg
                        500                 505                 510

Pro Gly Leu Tyr Trp Arg Leu Cys Trp Lys Phe Val Ser Pro Ala Phe
                        515                 520                 525

Leu Leu Phe Val Val Val Ser Ile Ile Asn Phe Lys Pro Leu Thr
                530                 535                 540

Tyr Asp Asp Tyr Ile Phe Pro Pro Trp Ala Asn Trp Val Gly Trp Gly
        545                 550                 555                 560

Ile Ala Leu Ser Ser Met Val Leu Val Pro Ile Tyr Val Ile Tyr Lys
                        565                 570                 575

Phe Leu Ser Thr Gln Gly Ser Leu Trp Glu Arg Leu Ala Tyr Gly Ile
                        580                 585                 590

Thr Pro Glu Asn Glu His His Leu Val Ala Gln Arg Asp Ile Arg Gln
                        595                 600                 605

Phe Gln Leu Gln His Trp Leu Ala Ile
                610                 615

<210> SEQ ID NO 3
<211> LENGTH: 1854
<212> TYPE: DNA
<213> ORGANISM: Homo sapiens
<220> FEATURE:
<221> NAME/KEY: CDS
<222> LOCATION: (1)..(1851)

<400> SEQUENCE: 3 atg ctt ctg gcg cgg atg aac ccg cag gtg cag ccc gag aac aac ggg       48
Met Leu Leu Ala Arg Met Asn Pro Gln Val Gln Pro Glu Asn Asn Gly
 1               5                  10                  15 gcg gac acg ggt cca gag cag ccc ctt cgg gcg cgc aaa act gcg gag       96
Ala Asp Thr Gly Pro Glu Gln Pro Leu Arg Ala Arg Lys Thr Ala Glu
            20                  25                  30 ctg ctg gtg gtg aag gag cgc aac ggc gtc cag tgc ctg ctg gcg ccc      144
```

```
                Leu Leu Val Val Lys Glu Arg Asn Gly Val Gln Cys Leu Leu Ala Pro
                         35                  40                  45 cgc gac ggc gac gcg cag ccc cgg gag acc tgg ggc aag aag atc gac          192
Arg Asp Gly Asp Ala Gln Pro Arg Glu Thr Trp Gly Lys Lys Ile Asp
         50                  55                  60 ttc ctg ctg tcc gta gtc ggc ttc gca gtg gac ctg gcc aac gtg tgg          240
Phe Leu Leu Ser Val Val Gly Phe Ala Val Asp Leu Ala Asn Val Trp
 65                  70                  75                  80 cgc ttc ccc tac ctc tgc tac aag aac ggc ggt gcc ttc ttg atc              288
Arg Phe Pro Tyr Leu Cys Tyr Lys Asn Gly Gly Ala Phe Leu Ile
                 85                  90                  95 ccg tac aca ctg ttc ctt atc atc gcg ggg atg ccc ctg ttc tac atg          336
Pro Tyr Thr Leu Phe Leu Ile Ile Ala Gly Met Pro Leu Phe Tyr Met
             100                 105                 110 gag ctg gct ctg gga cag tac aac cgg gag ggg gct gcc acc gtt tgg          384
Glu Leu Ala Leu Gly Gln Tyr Asn Arg Glu Gly Ala Ala Thr Val Trp
             115                 120                 125 aaa atc tgc cca ttc ttc aaa ggc gtt ggc tat gct gtc atc ctg atc          432
Lys Ile Cys Pro Phe Phe Lys Gly Val Gly Tyr Ala Val Ile Leu Ile
 130                 135                 140 gcc ctg tac gtt ggc ttc tac tac aac gtc atc atc gcc tgg tca ctc          480
Ala Leu Tyr Val Gly Phe Tyr Tyr Asn Val Ile Ile Ala Trp Ser Leu
145                 150                 155                 160 tac tac ctc ttc tcc tcc ttc acc ctc aac ctg ccc tgg acc gac tgt          528
Tyr Tyr Leu Phe Ser Ser Phe Thr Leu Asn Leu Pro Trp Thr Asp Cys
                 165                 170                 175 ggc cac acc tgg aac agc ccc aac tgt acc gac ccc aag ctc ctc aat          576
Gly His Thr Trp Asn Ser Pro Asn Cys Thr Asp Pro Lys Leu Leu Asn
             180                 185                 190 ggc tcc gtg ctt ggc aac cac acc aag tac tcc aag tac aag ttc acg          624
Gly Ser Val Leu Gly Asn His Thr Lys Tyr Ser Lys Tyr Lys Phe Thr
             195                 200                 205 ccg gca gcc gag ttt tat gag cgt ggt gtc ctg cac ctt cac gag agc          672
Pro Ala Ala Glu Phe Tyr Glu Arg Gly Val Leu His Leu His Glu Ser
 210                 215                 220 agc ggg att cat gac atc ggc ctg ccc cag tgg cag ctc ttg ctc tgt          720
Ser Gly Ile His Asp Ile Gly Leu Pro Gln Trp Gln Leu Leu Leu Cys
225                 230                 235                 240 ctg atg gtc gtc gtc atc gtc ttg tat ttt agc ctc tgg aaa ggg gtg          768
Leu Met Val Val Val Ile Val Leu Tyr Phe Ser Leu Trp Lys Gly Val
                 245                 250                 255 aag aca tca gga aag gtg gtg tgg atc aca gcc acg ctg cct tac ttc          816
Lys Thr Ser Gly Lys Val Val Trp Ile Thr Ala Thr Leu Pro Tyr Phe
             260                 265                 270 gtg ctg ttc gtg ctc ctg gtc cat ggc gtc acg ctg ccc gga gcc tcc          864
Val Leu Phe Val Leu Leu Val His Gly Val Thr Leu Pro Gly Ala Ser
             275                 280                 285 aat ggc atc aat gcc tac ctg cac atc gac ttc tac cgc ttg aaa gag          912
Asn Gly Ile Asn Ala Tyr Leu His Ile Asp Phe Tyr Arg Leu Lys Glu
 290                 295                 300 gcc acg gta tgg att gat gcc gca act cag ata ttt ttt tcc ttg ggg          960
Ala Thr Val Trp Ile Asp Ala Ala Thr Gln Ile Phe Phe Ser Leu Gly
305                 310                 315                 320 gct gga ttt gga gta ttg att gca ttt gcc agt tac aac aaa ttt gac         1008
Ala Gly Phe Gly Val Leu Ile Ala Phe Ala Ser Tyr Asn Lys Phe Asp
                 325                 330                 335 aac aac tgt tac agg gat gcc ctg ctg acc agc agc atc aac tgt atc         1056
Asn Asn Cys Tyr Arg Asp Ala Leu Leu Thr Ser Ser Ile Asn Cys Ile
             340                 345                 350
```

-continued

```
acc agc ttc gtc tct ggg ttc gcc atc ttc tcc atc ctt ggt tac atg    1104
Thr Ser Phe Val Ser Gly Phe Ala Ile Phe Ser Ile Leu Gly Tyr Met
        355                 360                 365 gcc cat gaa cac aag gtc aac att gag gat gtg gcc aca gaa gga gct    1152
Ala His Glu His Lys Val Asn Ile Glu Asp Val Ala Thr Glu Gly Ala
370                 375                 380 ggc cta gtg ttc atc ctg tat cca gag gcc att tct acc ctg tct gga    1200
Gly Leu Val Phe Ile Leu Tyr Pro Glu Ala Ile Ser Thr Leu Ser Gly
385                 390                 395                 400 tct aca ttc tgg gct gtt gtg ttt ttc gtc atg ctc ctg gcg ctg ggc    1248
Ser Thr Phe Trp Ala Val Val Phe Phe Val Met Leu Leu Ala Leu Gly
                405                 410                 415 ctt gac agc tca atg gga ggc atg gag gct gtc atc acg ggc ctg gca    1296
Leu Asp Ser Ser Met Gly Gly Met Glu Ala Val Ile Thr Gly Leu Ala
            420                 425                 430 gat gac ttc cag gtc ctg aag cga cac cgg aaa ctc ttc aca ttt ggc    1344
Asp Asp Phe Gln Val Leu Lys Arg His Arg Lys Leu Phe Thr Phe Gly
        435                 440                 445 gtc acc ttc agc act ttc ctt ctc ccc ctg ttc tgc ata acc aag ggt    1392
Val Thr Phe Ser Thr Phe Leu Leu Pro Leu Phe Cys Ile Thr Lys Gly
450                 455                 460 gga att tac gtc ttg acc ctc ctg gac acc ttt gct gcg ggc acc tcc    1440
Gly Ile Tyr Val Leu Thr Leu Leu Asp Thr Phe Ala Ala Gly Thr Ser
465                 470                 475                 480 atc ctt ttt gct gtc ctc atg gaa gcc atc gga gtt tcc tgg ttt tat    1488
Ile Leu Phe Ala Val Leu Met Glu Ala Ile Gly Val Ser Trp Phe Tyr
                485                 490                 495 gga gtg gac agg ttc agc aac gac atc cag cag atg atg ggg ttc agg    1536
Gly Val Asp Arg Phe Ser Asn Asp Ile Gln Gln Met Met Gly Phe Arg
            500                 505                 510 ccg ggt cta tac tgg aga ctg tgc tgg aag ttc gtc agt cct gcc ttc    1584
Pro Gly Leu Tyr Trp Arg Leu Cys Trp Lys Phe Val Ser Pro Ala Phe
        515                 520                 525 ctc ctg ttc gtg gtt gtg gtc agc atc atc aac ttc aag cca ctc acc    1632
Leu Leu Phe Val Val Val Val Ser Ile Ile Asn Phe Lys Pro Leu Thr
530                 535                 540 tac gac gac tac atc ttc ccg ccc tgg gcc aac tgg gtg ggg tgg ggc    1680
Tyr Asp Asp Tyr Ile Phe Pro Pro Trp Ala Asn Trp Val Gly Trp Gly
545                 550                 555                 560 atc gcc ctg tcc tcc atg gtc ctg gtg ccc atc tac gtc atc tat aag    1728
Ile Ala Leu Ser Ser Met Val Leu Val Pro Ile Tyr Val Ile Tyr Lys
                565                 570                 575 ttc ctc agc acg cag ggc tct ctt tgg gag aga ctg gcc tat ggc atc    1776
Phe Leu Ser Thr Gln Gly Ser Leu Trp Glu Arg Leu Ala Tyr Gly Ile
            580                 585                 590 acg cca gag aac gag cac cac ctg gtg gct cag agg gac atc aga cag    1824
Thr Pro Glu Asn Glu His His Leu Val Ala Gln Arg Asp Ile Arg Gln
        595                 600                 605 ttc cag ttg caa cac tgg ctg gcc atc tga                            1854
Phe Gln Leu Gln His Trp Leu Ala Ile
    610                 615

<210> SEQ ID NO 4
<211> LENGTH: 617
<212> TYPE: PRT
<213> ORGANISM: Homo sapiens

<400> SEQUENCE: 4

Met Leu Leu Ala Arg Met Asn Pro Gln Val Gln Pro Glu Asn Asn Gly
1               5                   10                  15
```

```
Ala Asp Thr Gly Pro Glu Gln Pro Leu Arg Ala Arg Lys Thr Ala Glu
             20                  25                  30

Leu Leu Val Val Lys Glu Arg Asn Gly Val Gln Cys Leu Leu Ala Pro
         35                  40                  45

Arg Asp Gly Asp Ala Gln Pro Arg Glu Thr Trp Gly Lys Lys Ile Asp
     50                  55                  60

Phe Leu Leu Ser Val Val Gly Phe Ala Val Asp Leu Ala Asn Val Trp
 65                  70                  75                  80

Arg Phe Pro Tyr Leu Cys Tyr Lys Asn Gly Gly Ala Phe Leu Ile
                 85                  90                  95

Pro Tyr Thr Leu Phe Leu Ile Ile Ala Gly Met Pro Leu Phe Tyr Met
             100                 105                 110

Glu Leu Ala Leu Gly Gln Tyr Asn Arg Glu Gly Ala Ala Thr Val Trp
         115                 120                 125

Lys Ile Cys Pro Phe Phe Lys Gly Val Gly Tyr Ala Val Ile Leu Ile
     130                 135                 140

Ala Leu Tyr Val Gly Phe Tyr Tyr Asn Val Ile Ile Ala Trp Ser Leu
145                 150                 155                 160

Tyr Tyr Leu Phe Ser Ser Phe Thr Leu Asn Leu Pro Trp Thr Asp Cys
                 165                 170                 175

Gly His Thr Trp Asn Ser Pro Asn Cys Thr Asp Pro Lys Leu Leu Asn
             180                 185                 190

Gly Ser Val Leu Gly Asn His Thr Lys Tyr Ser Lys Tyr Lys Phe Thr
         195                 200                 205

Pro Ala Ala Glu Phe Tyr Glu Arg Gly Val Leu His Leu His Glu Ser
     210                 215                 220

Ser Gly Ile His Asp Ile Gly Leu Pro Gln Trp Gln Leu Leu Leu Cys
225                 230                 235                 240

Leu Met Val Val Ile Val Leu Tyr Phe Ser Leu Trp Lys Gly Val
                 245                 250                 255

Lys Thr Ser Gly Lys Val Val Trp Ile Thr Ala Thr Leu Pro Tyr Phe
             260                 265                 270

Val Leu Phe Val Leu Leu Val His Gly Val Thr Leu Pro Gly Ala Ser
         275                 280                 285

Asn Gly Ile Asn Ala Tyr Leu His Ile Asp Phe Tyr Arg Leu Lys Glu
     290                 295                 300

Ala Thr Val Trp Ile Asp Ala Ala Thr Gln Ile Phe Phe Ser Leu Gly
305                 310                 315                 320

Ala Gly Phe Gly Val Leu Ile Ala Phe Ala Ser Tyr Asn Lys Phe Asp
                 325                 330                 335

Asn Asn Cys Tyr Arg Asp Ala Leu Leu Thr Ser Ile Asn Cys Ile
             340                 345                 350

Thr Ser Phe Val Ser Gly Phe Ala Ile Phe Ser Ile Leu Gly Tyr Met
         355                 360                 365

Ala His Glu His Lys Val Asn Ile Glu Asp Val Ala Thr Glu Gly Ala
     370                 375                 380

Gly Leu Val Phe Ile Leu Tyr Pro Glu Ala Ile Ser Thr Leu Ser Gly
385                 390                 395                 400

Ser Thr Phe Trp Ala Val Val Phe Phe Val Met Leu Leu Ala Leu Gly
                 405                 410                 415

Leu Asp Ser Ser Met Gly Gly Met Glu Ala Val Ile Thr Gly Leu Ala
             420                 425                 430

Asp Asp Phe Gln Val Leu Lys Arg His Arg Lys Leu Phe Thr Phe Gly
```

```
                435                 440                 445
Val Thr Phe Ser Thr Phe Leu Leu Pro Leu Phe Cys Ile Thr Lys Gly
            450                 455                 460
Gly Ile Tyr Val Leu Thr Leu Leu Asp Thr Phe Ala Ala Gly Thr Ser
465                 470                 475                 480
Ile Leu Phe Ala Val Leu Met Glu Ala Ile Gly Val Ser Trp Phe Tyr
                485                 490                 495
Gly Val Asp Arg Phe Ser Asn Asp Ile Gln Gln Met Met Gly Phe Arg
            500                 505                 510
Pro Gly Leu Tyr Trp Arg Leu Cys Trp Lys Phe Val Ser Pro Ala Phe
            515                 520                 525
Leu Leu Phe Val Val Val Ser Ile Ile Asn Phe Lys Pro Leu Thr
            530                 535                 540
Tyr Asp Asp Tyr Ile Phe Pro Pro Trp Ala Asn Trp Val Gly Trp Gly
545                 550                 555                 560
Ile Ala Leu Ser Ser Met Val Leu Val Pro Ile Tyr Val Ile Tyr Lys
                565                 570                 575
Phe Leu Ser Thr Gln Gly Ser Leu Trp Glu Arg Leu Ala Tyr Gly Ile
            580                 585                 590
Thr Pro Glu Asn Glu His His Leu Val Ala Gln Arg Asp Ile Arg Gln
            595                 600                 605
Phe Gln Leu Gln His Trp Leu Ala Ile
            610                 615
```

<210> SEQ ID NO 5
<211> LENGTH: 41
<212> TYPE: DNA
<213> ORGANISM: Homo sapiens

<400> SEQUENCE: 5
ccttcagtac tttccttctc cccctgttct gcataaccaa g                  41

<210> SEQ ID NO 6
<211> LENGTH: 41
<212> TYPE: DNA
<213> ORGANISM: Homo sapiens

<400> SEQUENCE: 6
cttggttatg cagaacaggg ggagaaggaa agtactgaag g                  41

<210> SEQ ID NO 7
<211> LENGTH: 18
<212> TYPE: DNA
<213> ORGANISM: Homo sapiens

<400> SEQUENCE: 7
cattctgggc tgttgtgt                                            18

<210> SEQ ID NO 8
<211> LENGTH: 21
<212> TYPE: DNA
<213> ORGANISM: Homo sapiens

<400> SEQUENCE: 8
gtggttgtgg tcagcatcat c                                        21

<210> SEQ ID NO 9
<211> LENGTH: 15
<212> TYPE: DNA

-continued

<210> SEQ ID NO 9
<211> LENGTH: 15
<212> TYPE: DNA
<213> ORGANISM: Homo sapiens

<400> SEQUENCE: 9
ccttctcgcc ctgtt                                                      15

<210> SEQ ID NO 10
<211> LENGTH: 15
<212> TYPE: DNA
<213> ORGANISM: Homo sapiens

<400> SEQUENCE: 10
ccttctcccc ctgtt                                                      15

<210> SEQ ID NO 11
<211> LENGTH: 1854
<212> TYPE: DNA
<213> ORGANISM: Homo sapiens
<220> FEATURE:
<221> NAME/KEY: CDS
<222> LOCATION: (1)..(1851)

<400> SEQUENCE: 11

```
atg att ctg gcg cgg atg aac ccg cag gtg cag ccc gag aac aac ggg      48
Met Ile Leu Ala Arg Met Asn Pro Gln Val Gln Pro Glu Asn Asn Gly
 1               5                  10                  15 gcg gac acg ggt cca gag cag ccc ctt cgg gcg cgc aaa act gcg gag      96
Ala Asp Thr Gly Pro Glu Gln Pro Leu Arg Ala Arg Lys Thr Ala Glu
             20                  25                  30 ctg ctg gtg gtg aag gag cgc aac ggc gtc cag tgc ctg ctg gcg ccc     144
Leu Leu Val Val Lys Glu Arg Asn Gly Val Gln Cys Leu Leu Ala Pro
         35                  40                  45 cgc gac ggc gac gcg cag ccc cgg gag acc tgg ggc aag aag atc gac     192
Arg Asp Gly Asp Ala Gln Pro Arg Glu Thr Trp Gly Lys Lys Ile Asp
     50                  55                  60 ttc ctg ctg tcc gta gtc ggc ttc gca gtg gac ctg gcc aac gtg tgg     240
Phe Leu Leu Ser Val Val Gly Phe Ala Val Asp Leu Ala Asn Val Trp
 65                  70                  75                  80 cgc ttc ccc tac ctc tgc tac aag aac ggc ggc ggt gcc ttc ttg atc     288
Arg Phe Pro Tyr Leu Cys Tyr Lys Asn Gly Gly Gly Ala Phe Leu Ile
                 85                  90                  95 ccg tac aca ctg ttc ctt atc atc gcg ggg atg ccc ctg ttc tac atg     336
Pro Tyr Thr Leu Phe Leu Ile Ile Ala Gly Met Pro Leu Phe Tyr Met
            100                 105                 110 gag ctg gct ctg gga cag tac aac cgg gag ggg gct gcc acc gtt tgg     384
Glu Leu Ala Leu Gly Gln Tyr Asn Arg Glu Gly Ala Ala Thr Val Trp
        115                 120                 125 aaa atc tgc cca ttc ttc aaa ggc gtt ggc tat gct gtc atc ctg atc     432
Lys Ile Cys Pro Phe Phe Lys Gly Val Gly Tyr Ala Val Ile Leu Ile
    130                 135                 140 gcc ctg tac gtt ggc ttc tac tac aac gtc atc atc gcc tgg tca ctc     480
Ala Leu Tyr Val Gly Phe Tyr Tyr Asn Val Ile Ile Ala Trp Ser Leu
145                 150                 155                 160 tac tac ctc ttc tcc tcc ttc acc ctc aac ctg ccc tgg acc gac tgt     528
Tyr Tyr Leu Phe Ser Ser Phe Thr Leu Asn Leu Pro Trp Thr Asp Cys
                165                 170                 175 ggc cac acc tgg aac agc ccc aac tgt acc gac ccc aag ctc ctc aat     576
Gly His Thr Trp Asn Ser Pro Asn Cys Thr Asp Pro Lys Leu Leu Asn
            180                 185                 190 ggc tcc gtg ctt ggc aac cac acc aag tac tcc aag tac aag ttc acg     624
Gly Ser Val Leu Gly Asn His Thr Lys Tyr Ser Lys Tyr Lys Phe Thr
        195                 200                 205
```

```
ccg gca gcc gag ttt tat gag cgt ggt gtc ctg cac ctt cac gag agc      672
Pro Ala Ala Glu Phe Tyr Glu Arg Gly Val Leu His Leu His Glu Ser
    210             215                 220 agc ggg att cat gac atc ggc ctg ccc cag tgg cag ctc ttg ctc tgt      720
Ser Gly Ile His Asp Ile Gly Leu Pro Gln Trp Gln Leu Leu Leu Cys
225                 230                 235                 240 ctg atg gtc gtc gtc atc gtc ttg tat ttt agc ctc tgg aaa ggg gtg      768
Leu Met Val Val Val Ile Val Leu Tyr Phe Ser Leu Trp Lys Gly Val
                245                 250                 255 aag aca tca gga aag gtg gtg tgg atc aca gcc acg ctg cct tac ttc      816
Lys Thr Ser Gly Lys Val Val Trp Ile Thr Ala Thr Leu Pro Tyr Phe
            260                 265                 270 gtg ctg ttc gtg ctc ctg gtc cat ggc gtc acg ctg ccc gga gcc tcc      864
Val Leu Phe Val Leu Leu Val His Gly Val Thr Leu Pro Gly Ala Ser
        275                 280                 285 aat ggc atc aat gcc tac ctg cac atc gac ttc tac cgc ttg aaa gag      912
Asn Gly Ile Asn Ala Tyr Leu His Ile Asp Phe Tyr Arg Leu Lys Glu
    290                 295                 300 gcc acg gta tgg att gat gcc gca act cag ata ttt ttt tcc ttg ggg      960
Ala Thr Val Trp Ile Asp Ala Ala Thr Gln Ile Phe Phe Ser Leu Gly
305                 310                 315                 320 gct gga ttt gga gta ttg att gca ttt gcc agt tac aac aaa ttt gac     1008
Ala Gly Phe Gly Val Leu Ile Ala Phe Ala Ser Tyr Asn Lys Phe Asp
                325                 330                 335 aac aac tgt tac agg gat gcc ctg ctg acc agc agc atc aac tgt atc     1056
Asn Asn Cys Tyr Arg Asp Ala Leu Leu Thr Ser Ser Ile Asn Cys Ile
            340                 345                 350 acc agc ttc gtc tct ggg ttc gcc atc ttc tcc atc ctt ggt tac atg     1104
Thr Ser Phe Val Ser Gly Phe Ala Ile Phe Ser Ile Leu Gly Tyr Met
        355                 360                 365 gcc cat gaa cac aag gtc aac att gag gat gtg gcc aca gaa gga gct     1152
Ala His Glu His Lys Val Asn Ile Glu Asp Val Ala Thr Glu Gly Ala
    370                 375                 380 ggc cta gtg ttc atc ctg tat cca gag gcc att tct acc ctg tct gga     1200
Gly Leu Val Phe Ile Leu Tyr Pro Glu Ala Ile Ser Thr Leu Ser Gly
385                 390                 395                 400 tct aca ttc tgg gct gtt gtg ttt ttc gtc atg ctc ctg gcg ctg ggc     1248
Ser Thr Phe Trp Ala Val Val Phe Phe Val Met Leu Leu Ala Leu Gly
                405                 410                 415 ctt gac agc tca atg gga ggc atg gag gct gtc atc acg ggc ctg gca     1296
Leu Asp Ser Ser Met Gly Gly Met Glu Ala Val Ile Thr Gly Leu Ala
            420                 425                 430 gat gac ttc cag gtc ctg aag cga cac cgg aaa ctc ttc aca ttt ggc     1344
Asp Asp Phe Gln Val Leu Lys Arg His Arg Lys Leu Phe Thr Phe Gly
        435                 440                 445 gtc acc ttc agc act ttc ctt ctc gcc ctg ttc tgc ata acc aag ggt     1392
Val Thr Phe Ser Thr Phe Leu Leu Ala Leu Phe Cys Ile Thr Lys Gly
    450                 455                 460 gga att tac gtc ttg acc ctc ctg gac acc ttt gct gcg ggc acc tcc     1440
Gly Ile Tyr Val Leu Thr Leu Leu Asp Thr Phe Ala Ala Gly Thr Ser
465                 470                 475                 480 atc ctt ttt gct gtc ctc atg gaa gcc atc gga gtt tcc tgg ttt tat     1488
Ile Leu Phe Ala Val Leu Met Glu Ala Ile Gly Val Ser Trp Phe Tyr
                485                 490                 495 gga gtg gac agg ttc agc aac gac atc cag cag atg atg ggg ttc agg     1536
Gly Val Asp Arg Phe Ser Asn Asp Ile Gln Gln Met Met Gly Phe Arg
            500                 505                 510 ccg ggt cta tac tgg aga ctg tgc tgg aag ttc gtc agt cct gcc ttc     1584
Pro Gly Leu Tyr Trp Arg Leu Cys Trp Lys Phe Val Ser Pro Ala Phe
        515                 520                 525
```

```
ctc ctg ttc gtg gtt gtg gtc agc atc atc aac ttc aag cca ctc acc    1632
Leu Leu Phe Val Val Val Val Ser Ile Ile Asn Phe Lys Pro Leu Thr
        530                 535                 540 tac gac gac tac atc ttc ccg ccc tgg gcc aac tgg gtg ggg tgg ggc    1680
Tyr Asp Asp Tyr Ile Phe Pro Pro Trp Ala Asn Trp Val Gly Trp Gly
545                 550                 555                 560 atc gcc ctg tcc tcc atg gtc ctg gtc ccc atc tac gtc atc tat aag    1728
Ile Ala Leu Ser Ser Met Val Leu Val Pro Ile Tyr Val Ile Tyr Lys
                565                 570                 575 ttc ctc agc acg cag ggc tct ctt tgg gag aga ctg gcc tat ggc atc    1776
Phe Leu Ser Thr Gln Gly Ser Leu Trp Glu Arg Leu Ala Tyr Gly Ile
            580                 585                 590 acg cca gag aac gag cac cac ctg gtg gct cag agg gac atc aga cag    1824
Thr Pro Glu Asn Glu His His Leu Val Ala Gln Arg Asp Ile Arg Gln
        595                 600                 605 ttc cag ttg caa cac tgg ctg gcc atc tga                            1854
Phe Gln Leu Gln His Trp Leu Ala Ile
610                 615

<210> SEQ ID NO 12
<211> LENGTH: 617
<212> TYPE: PRT
<213> ORGANISM: Homo sapiens

<400> SEQUENCE: 12

Met Ile Leu Ala Arg Met Asn Pro Gln Val Gln Pro Glu Asn Asn Gly
1               5                   10                  15

Ala Asp Thr Gly Pro Glu Gln Pro Leu Arg Ala Arg Lys Thr Ala Glu
            20                  25                  30

Leu Leu Val Val Lys Glu Arg Asn Gly Val Gln Cys Leu Leu Ala Pro
        35                  40                  45

Arg Asp Gly Asp Ala Gln Pro Arg Glu Thr Trp Gly Lys Lys Ile Asp
    50                  55                  60

Phe Leu Leu Ser Val Val Gly Phe Ala Val Asp Leu Ala Asn Val Trp
65                  70                  75                  80

Arg Phe Pro Tyr Leu Cys Tyr Lys Asn Gly Gly Gly Ala Phe Leu Ile
                85                  90                  95

Pro Tyr Thr Leu Phe Leu Ile Ile Ala Gly Met Pro Leu Phe Tyr Met
            100                 105                 110

Glu Leu Ala Leu Gly Gln Tyr Asn Arg Glu Gly Ala Ala Thr Val Trp
        115                 120                 125

Lys Ile Cys Pro Phe Phe Lys Gly Val Gly Tyr Ala Val Ile Leu Ile
    130                 135                 140

Ala Leu Tyr Val Gly Phe Tyr Tyr Asn Val Ile Ile Ala Trp Ser Leu
145                 150                 155                 160

Tyr Tyr Leu Phe Ser Ser Phe Thr Leu Asn Leu Pro Trp Thr Asp Cys
                165                 170                 175

Gly His Thr Trp Asn Ser Pro Asn Cys Thr Asp Pro Lys Leu Leu Asn
            180                 185                 190

Gly Ser Val Leu Gly Asn His Thr Lys Tyr Ser Lys Tyr Lys Phe Thr
        195                 200                 205

Pro Ala Ala Glu Phe Tyr Glu Arg Gly Val Leu His Leu His Glu Ser
    210                 215                 220

Ser Gly Ile His Asp Ile Gly Leu Pro Gln Trp Gln Leu Leu Leu Cys
225                 230                 235                 240

Leu Met Val Val Val Ile Val Leu Tyr Phe Ser Leu Trp Lys Gly Val
```

-continued

```
                245                 250                 255
Lys Thr Ser Gly Lys Val Val Trp Ile Thr Ala Thr Leu Pro Tyr Phe
            260                 265                 270
Val Leu Phe Val Leu Leu Val His Gly Val Thr Leu Pro Gly Ala Ser
        275                 280                 285
Asn Gly Ile Asn Ala Tyr Leu His Ile Asp Phe Tyr Arg Leu Lys Glu
    290                 295                 300
Ala Thr Val Trp Ile Asp Ala Ala Thr Gln Ile Phe Phe Ser Leu Gly
305                 310                 315                 320
Ala Gly Phe Gly Val Leu Ile Ala Phe Ala Ser Tyr Asn Lys Phe Asp
                325                 330                 335
Asn Asn Cys Tyr Arg Asp Ala Leu Leu Thr Ser Ser Ile Asn Cys Ile
            340                 345                 350
Thr Ser Phe Val Ser Gly Phe Ala Ile Phe Ser Ile Leu Gly Tyr Met
        355                 360                 365
Ala His Glu His Lys Val Asn Ile Glu Asp Val Ala Thr Glu Gly Ala
    370                 375                 380
Gly Leu Val Phe Ile Leu Tyr Pro Glu Ala Ile Ser Thr Leu Ser Gly
385                 390                 395                 400
Ser Thr Phe Trp Ala Val Val Phe Phe Val Met Leu Leu Ala Leu Gly
                405                 410                 415
Leu Asp Ser Ser Met Gly Gly Met Glu Ala Val Ile Thr Gly Leu Ala
            420                 425                 430
Asp Asp Phe Gln Val Leu Lys Arg His Arg Lys Leu Phe Thr Phe Gly
        435                 440                 445
Val Thr Phe Ser Thr Phe Leu Leu Ala Leu Phe Cys Ile Thr Lys Gly
    450                 455                 460
Gly Ile Tyr Val Leu Thr Leu Leu Asp Thr Phe Ala Ala Gly Thr Ser
465                 470                 475                 480
Ile Leu Phe Ala Val Leu Met Glu Ala Ile Gly Val Ser Trp Phe Tyr
                485                 490                 495
Gly Val Asp Arg Phe Ser Asn Asp Ile Gln Gln Met Met Gly Phe Arg
            500                 505                 510
Pro Gly Leu Tyr Trp Arg Leu Cys Trp Lys Phe Val Ser Pro Ala Phe
        515                 520                 525
Leu Leu Phe Val Val Val Ser Ile Ile Asn Phe Lys Pro Leu Thr
    530                 535                 540
Tyr Asp Asp Tyr Ile Phe Pro Pro Trp Ala Asn Trp Val Gly Trp Gly
545                 550                 555                 560
Ile Ala Leu Ser Ser Met Val Leu Val Pro Ile Tyr Val Ile Tyr Lys
                565                 570                 575
Phe Leu Ser Thr Gln Gly Ser Leu Trp Glu Arg Leu Ala Tyr Gly Ile
            580                 585                 590
Thr Pro Glu Asn Glu His His Leu Val Ala Gln Arg Asp Ile Arg Gln
        595                 600                 605
Phe Gln Leu Gln His Trp Leu Ala Ile
    610                 615

<210> SEQ ID NO 13
<211> LENGTH: 1854
<212> TYPE: DNA
<213> ORGANISM: Homo sapiens
<220> FEATURE:
<221> NAME/KEY: CDS
<222> LOCATION: (1)..(1851)
```

<400> SEQUENCE: 13

```
atg att ctg gcg cgg atg aac ccg cag gtg cag ccc gag aac aac ggg      48
Met Ile Leu Ala Arg Met Asn Pro Gln Val Gln Pro Glu Asn Asn Gly
 1               5                  10                  15 gcg gac acg ggt cca gag cag ccc ctt cgg gcg cgc aaa act gcg gag      96
Ala Asp Thr Gly Pro Glu Gln Pro Leu Arg Ala Arg Lys Thr Ala Glu
             20                  25                  30 ctg ctg gtg gtg aag gag cgc aac ggc gtc cag tgc ctg ctg gcg ccc     144
Leu Leu Val Val Lys Glu Arg Asn Gly Val Gln Cys Leu Leu Ala Pro
         35                  40                  45 cgc gac ggc gac gcg cag ccc cgg gag acc tgg ggc aag aag atc gac     192
Arg Asp Gly Asp Ala Gln Pro Arg Glu Thr Trp Gly Lys Lys Ile Asp
 50                  55                  60 ttc ctg ctg tcc gta gtc ggc ttc gca gtg gac ctg gcc aac gtg tgg     240
Phe Leu Leu Ser Val Val Gly Phe Ala Val Asp Leu Ala Asn Val Trp
 65                  70                  75                  80 cgc ttc ccc tac ctc tgc tac aag aac ggc ggc ggt gcc ttc ttg atc     288
Arg Phe Pro Tyr Leu Cys Tyr Lys Asn Gly Gly Gly Ala Phe Leu Ile
                 85                  90                  95 ccg tac aca ctg ttc ctt atc atc gcg ggg atg ccc ctg ttc tac atg     336
Pro Tyr Thr Leu Phe Leu Ile Ile Ala Gly Met Pro Leu Phe Tyr Met
            100                 105                 110 gag ctg gct ctg gga cag tac aac cgg gag ggg gct gcc acc gtt tgg     384
Glu Leu Ala Leu Gly Gln Tyr Asn Arg Glu Gly Ala Ala Thr Val Trp
        115                 120                 125 aaa atc tgc cca ttc ttc aaa ggc gtt ggc tat gct gtc atc ctg atc     432
Lys Ile Cys Pro Phe Phe Lys Gly Val Gly Tyr Ala Val Ile Leu Ile
130                 135                 140 gcc ctg tac gtt ggc ttc tac tac aac gtc atc atc gcc tgg tca ctc     480
Ala Leu Tyr Val Gly Phe Tyr Tyr Asn Val Ile Ile Ala Trp Ser Leu
145                 150                 155                 160 tac tac ctc ttc tcc tcc ttc acc ctc aac ctg ccc tgg acc gac tgt     528
Tyr Tyr Leu Phe Ser Ser Phe Thr Leu Asn Leu Pro Trp Thr Asp Cys
                165                 170                 175 ggc cac acc tgg aac agc ccc aac tgt acc gac ccc aag ctc ctc aat     576
Gly His Thr Trp Asn Ser Pro Asn Cys Thr Asp Pro Lys Leu Leu Asn
            180                 185                 190 ggc tcc gtg ctt ggc aac cac acc aag tac tcc aag tac aag ttc acg     624
Gly Ser Val Leu Gly Asn His Thr Lys Tyr Ser Lys Tyr Lys Phe Thr
        195                 200                 205 ccg gca gcc gag ttt tat gag cgt ggt gtc ctg cac ctt cac gag agc     672
Pro Ala Ala Glu Phe Tyr Glu Arg Gly Val Leu His Leu His Glu Ser
210                 215                 220 agc ggg att cat gac atc ggc ctg ccc cag tgg cag ctc ttg ctc tgt     720
Ser Gly Ile His Asp Ile Gly Leu Pro Gln Trp Gln Leu Leu Leu Cys
225                 230                 235                 240 ctg atg gtc gtc gtc atc gtc ttg tat ttt agc ctc tgg aaa ggg gtg     768
Leu Met Val Val Val Ile Val Leu Tyr Phe Ser Leu Trp Lys Gly Val
                245                 250                 255 aag aca tca gga aag gtg gtg tgg atc aca gcc acg ctg cct tac ttc     816
Lys Thr Ser Gly Lys Val Val Trp Ile Thr Ala Thr Leu Pro Tyr Phe
            260                 265                 270 gtg ctg ttc gtg ctc ctg gtc cat ggc gtc acg ctg ccc gga gcc tcc     864
Val Leu Phe Val Leu Leu Val His Gly Val Thr Leu Pro Gly Ala Ser
        275                 280                 285 aat ggc atc aat gcc tac ctg cac atc gac ttc tac cgc ttg aaa gag     912
Asn Gly Ile Asn Ala Tyr Leu His Ile Asp Phe Tyr Arg Leu Lys Glu
290                 295                 300 gcc acg gta tgg att gat gcc gca act cag ata ttt ttt tcc ttg ggg     960
Ala Thr Val Trp Ile Asp Ala Ala Thr Gln Ile Phe Phe Ser Leu Gly
```

```
                    -continued

Ala Thr Val Trp Ile Asp Ala Ala Thr Gln Ile Phe Phe Ser Leu Gly
305                 310                 315                 320 gct gga ttt gga gta ttg att gca ttt gcc agt tac aac aaa ttt gac      1008
Ala Gly Phe Gly Val Leu Ile Ala Phe Ala Ser Tyr Asn Lys Phe Asp
                    325                 330                 335 aac aac tgt tac agg gat gcc ctg ctg acc agc agc atc aac tgt atc      1056
Asn Asn Cys Tyr Arg Asp Ala Leu Leu Thr Ser Ser Ile Asn Cys Ile
                340                 345                 350 acc agc ttc gtc tct ggg ttc gcc atc ttc tcc atc ctt ggt tac atg      1104
Thr Ser Phe Val Ser Gly Phe Ala Ile Phe Ser Ile Leu Gly Tyr Met
            355                 360                 365 gcc cat gaa cac aag gtc aac att gag gat gtg gcc aca gaa gga gct      1152
Ala His Glu His Lys Val Asn Ile Glu Asp Val Ala Thr Glu Gly Ala
        370                 375                 380 ggc cta gtg ttc atc ctg tat cca gag gcc att tct acc ctg tct gga      1200
Gly Leu Val Phe Ile Leu Tyr Pro Glu Ala Ile Ser Thr Leu Ser Gly
385                 390                 395                 400 tct aca ttc tgg gct gtt gtg ttt ttc gtc atg ctc ctg gcg ctg ggc      1248
Ser Thr Phe Trp Ala Val Val Phe Phe Val Met Leu Leu Ala Leu Gly
                    405                 410                 415 ctt gac agc tca atg gga ggc atg gag gct gtc atc acg ggc ctg gca      1296
Leu Asp Ser Ser Met Gly Gly Met Glu Ala Val Ile Thr Gly Leu Ala
                420                 425                 430 gat gac ttc cag gtc ctg aag cga cac cgg aaa ctc ttc aca ttt ggc      1344
Asp Asp Phe Gln Val Leu Lys Arg His Arg Lys Leu Phe Thr Phe Gly
            435                 440                 445 gtc acc ttc agc act ttc ctt ctc ccc ctg ttc tgc ata acc aag ggt      1392
Val Thr Phe Ser Thr Phe Leu Leu Pro Leu Phe Cys Ile Thr Lys Gly
        450                 455                 460 gga att tac gtc ttg acc ctc ctg gac acc ttt gct gcg ggc acc tcc      1440
Gly Ile Tyr Val Leu Thr Leu Leu Asp Thr Phe Ala Ala Gly Thr Ser
465                 470                 475                 480 atc ctt ttt gct gtc ctc atg gaa gcc atc gga gtt tcc tgg ttt tat      1488
Ile Leu Phe Ala Val Leu Met Glu Ala Ile Gly Val Ser Trp Phe Tyr
                    485                 490                 495 gga gtg gac agg ttc agc aac gac atc cag cag atg atg ggg ttc agg      1536
Gly Val Asp Arg Phe Ser Asn Asp Ile Gln Gln Met Met Gly Phe Arg
                500                 505                 510 ccg ggt cta tac tgg aga ctg tgc tgg aag ttc gtc agt cct gcc ttc      1584
Pro Gly Leu Tyr Trp Arg Leu Cys Trp Lys Phe Val Ser Pro Ala Phe
            515                 520                 525 ctc ctg ttc gtg gtt gtg gtc agc atc atc aac ttc aag cca ctc acc      1632
Leu Leu Phe Val Val Val Ser Ile Ile Asn Phe Lys Pro Leu Thr
        530                 535                 540 tac gac gac tac atc ttc ccg ccc tgg gcc aac tgg gtg ggg tgg ggc      1680
Tyr Asp Asp Tyr Ile Phe Pro Pro Trp Ala Asn Trp Val Gly Trp Gly
545                 550                 555                 560 atc gcc ctg tcc tcc atg gtc ctg gtg ccc atc tac gtc atc tat aag      1728
Ile Ala Leu Ser Ser Met Val Leu Val Pro Ile Tyr Val Ile Tyr Lys
                    565                 570                 575 ttc ctc agc acg cag ggc tct ctt tgg gag aga ctg gcc tat ggc atc      1776
Phe Leu Ser Thr Gln Gly Ser Leu Trp Glu Arg Leu Ala Tyr Gly Ile
                580                 585                 590 acg cca gag aac gag cac cac ctg gtg gct cag agg gac atc aga cag      1824
Thr Pro Glu Asn Glu His His Leu Val Ala Gln Arg Asp Ile Arg Gln
            595                 600                 605 ttc cag ttg caa cac tgg ctg gcc atc tga                              1854
Phe Gln Leu Gln His Trp Leu Ala Ile
    610                 615
```

<210> SEQ ID NO 14
<211> LENGTH: 617
<212> TYPE: PRT
<213> ORGANISM: Homo sapiens

<400> SEQUENCE: 14

```
Met Ile Leu Ala Arg Met Asn Pro Gln Val Gln Pro Glu Asn Asn Gly
  1               5                  10                  15

Ala Asp Thr Gly Pro Glu Gln Pro Leu Arg Ala Arg Lys Thr Ala Glu
             20                  25                  30

Leu Leu Val Val Lys Glu Arg Asn Gly Val Gln Cys Leu Leu Ala Pro
         35                  40                  45

Arg Asp Gly Asp Ala Gln Pro Arg Glu Thr Trp Gly Lys Lys Ile Asp
     50                  55                  60

Phe Leu Leu Ser Val Val Gly Phe Ala Val Asp Leu Ala Asn Val Trp
 65                  70                  75                  80

Arg Phe Pro Tyr Leu Cys Tyr Lys Asn Gly Gly Gly Ala Phe Leu Ile
                 85                  90                  95

Pro Tyr Thr Leu Phe Leu Ile Ile Ala Gly Met Pro Leu Phe Tyr Met
            100                 105                 110

Glu Leu Ala Leu Gly Gln Tyr Asn Arg Glu Gly Ala Ala Thr Val Trp
        115                 120                 125

Lys Ile Cys Pro Phe Phe Lys Gly Val Gly Tyr Ala Val Ile Leu Ile
    130                 135                 140

Ala Leu Tyr Val Gly Phe Tyr Tyr Asn Val Ile Ala Trp Ser Leu
145                 150                 155                 160

Tyr Tyr Leu Phe Ser Ser Phe Thr Leu Asn Leu Pro Trp Thr Asp Cys
                165                 170                 175

Gly His Thr Trp Asn Ser Pro Asn Cys Thr Asp Pro Lys Leu Leu Asn
            180                 185                 190

Gly Ser Val Leu Gly Asn His Thr Lys Tyr Ser Lys Tyr Lys Phe Thr
        195                 200                 205

Pro Ala Ala Glu Phe Tyr Glu Arg Gly Val Leu His Leu His Glu Ser
    210                 215                 220

Ser Gly Ile His Asp Ile Gly Leu Pro Gln Trp Gln Leu Leu Leu Cys
225                 230                 235                 240

Leu Met Val Val Ile Val Leu Tyr Phe Ser Leu Trp Lys Gly Val
                245                 250                 255

Lys Thr Ser Gly Lys Val Val Trp Ile Thr Ala Thr Leu Pro Tyr Phe
                260                 265                 270

Val Leu Phe Val Leu Leu Val His Gly Val Thr Leu Pro Gly Ala Ser
            275                 280                 285

Asn Gly Ile Asn Ala Tyr Leu His Ile Asp Phe Tyr Arg Leu Lys Glu
    290                 295                 300

Ala Thr Val Trp Ile Asp Ala Ala Thr Gln Ile Phe Phe Ser Leu Gly
305                 310                 315                 320

Ala Gly Phe Gly Val Leu Ile Ala Phe Ala Ser Tyr Asn Lys Phe Asp
                325                 330                 335

Asn Asn Cys Tyr Arg Asp Ala Leu Leu Thr Ser Ser Ile Asn Cys Ile
            340                 345                 350

Thr Ser Phe Val Ser Gly Phe Ala Ile Phe Ser Ile Leu Gly Tyr Met
        355                 360                 365

Ala His Glu His Lys Val Asn Ile Glu Asp Val Ala Thr Glu Gly Ala
    370                 375                 380
```

Gly Leu Val Phe Ile Leu Tyr Pro Glu Ala Ile Ser Thr Leu Ser Gly
385                 390                 395                 400

Ser Thr Phe Trp Ala Val Val Phe Val Met Leu Leu Ala Leu Gly
            405                 410                 415

Leu Asp Ser Ser Met Gly Gly Met Glu Ala Val Ile Thr Gly Leu Ala
            420                 425                 430

Asp Asp Phe Gln Val Leu Lys Arg His Arg Lys Leu Phe Thr Phe Gly
            435                 440                 445

Val Thr Phe Ser Thr Phe Leu Leu Pro Leu Phe Cys Ile Thr Lys Gly
            450                 455                 460

Gly Ile Tyr Val Leu Thr Leu Leu Asp Thr Phe Ala Ala Gly Thr Ser
465                 470                 475                 480

Ile Leu Phe Ala Val Leu Met Glu Ala Ile Gly Val Ser Trp Phe Tyr
                485                 490                 495

Gly Val Asp Arg Phe Ser Asn Asp Ile Gln Gln Met Met Gly Phe Arg
                500                 505                 510

Pro Gly Leu Tyr Trp Arg Leu Cys Trp Lys Phe Val Ser Pro Ala Phe
            515                 520                 525

Leu Leu Phe Val Val Val Ser Ile Ile Asn Phe Lys Pro Leu Thr
530                 535                 540

Tyr Asp Asp Tyr Ile Phe Pro Pro Trp Ala Asn Trp Val Gly Trp Gly
545                 550                 555                 560

Ile Ala Leu Ser Ser Met Val Leu Val Pro Ile Tyr Val Ile Tyr Lys
                565                 570                 575

Phe Leu Ser Thr Gln Gly Ser Leu Trp Glu Arg Leu Ala Tyr Gly Ile
            580                 585                 590

Thr Pro Glu Asn Glu His His Leu Val Ala Gln Arg Asp Ile Arg Gln
            595                 600                 605

Phe Gln Leu Gln His Trp Leu Ala Ile
            610                 615

<210> SEQ ID NO 15
<211> LENGTH: 980
<212> TYPE: DNA
<213> ORGANISM: Homo sapiens
<220> FEATURE:
<221> NAME/KEY: exon
<222> LOCATION: (129)..(257)
<221> NAME/KEY: gene
<222> LOCATION: (129)..(800)
<221> NAME/KEY: exon
<222> LOCATION: (701)..(802)
<300> PUBLICATION INFORMATION:
<301> AUTHORS: Porzgen, P.
       Bonisch, H.
       Bruss, M.
<302> TITLE: Molecular Cloning and Organization of the Coding Region
       of the Human Norepinephrine Tranporter Gene
<303> JOURNAL: Biochem. Biophys. Res. Commun.
<304> VOLUME: 215
<305> ISSUE: (3)
<306> PAGES: 1145-1150
<307> DATE: 1995-10-24
<308> DATABASE ACCESSION NUMBER: x91117
<309> DATABASE ENTRY DATE: 1996-02-20

<400> SEQUENCE: 15
tttctcgaga gaggcaaggc agcctacatg agtcctgggc tgcaggaggc tctaggaacc    60
ctggggcctg agactgaggt ccagggagac cctaattcct gcaccccacc cctcctggtt   120 ccctccag atg gga ggc atg gag gct gtc atc acg ggc ctg gca gat gac   170

```
ttc cag gtc ctg aag cga cac cgg aaa ctc ttc aca ttt ggc gtc acc        218 ttc agc act ttc ctt ctc gcc ctg ttc tgc ata acc aag gtgagtaggg         267 gctgggctct gggtcacctg ggggcctctg aggccgcatt tcaataaagt caaacattcc      327
tagccttaga actgggctga gctcagggag aacaatgcag gatccagcat cctcaattca      387
gcggcctgac ccactagggt taggcccagt agtcttcttc catctctgas sctgaggatt      447
ccattcagcc ctgttaattg ccttattgac ttgagggsca gcaaaagtcc ctttggaacc      507
catctaactc tttattggct gaaactgagg tgactgtaac gtcaatacaa cagcaccaca      567
gccctatgcc ctgggttttc aaatagagct ccgagcaagt gggacagggg gcaggtaaga      627
gttgacagac acaacaatca gttcccacgt ttgaccaaag agggcctctt ggcttcttct      687
ctccctgtgc cag ggt gga att tac gtc ttg acc ctc ctg gac acc ttt         736 gct gcg ggc acc tcc atc ctt ttt gct gtc ctc atg gaa gcc atc gga        784 gtt tcc tgg ttt tat ggt atgtgagtgt gtggaaaagc ctcagctccc               832
agtcctccta gaatcctgca cctggaggtg tgcagggagg ccttccattt ccaggacagc      892
cacctaaaat tccagagtcc agcaagtcac ttattgggaa caaatctcaa tcctcggctc      952
atctttggat gaacctgccc ttaacagg                                         980
```

```
<210> SEQ ID NO 16
<211> LENGTH: 22
<212> TYPE: DNA
<213> ORGANISM: Homo sapiens

<400> SEQUENCE: 16
aggaccggta aagttcctct cg                                               22

<210> SEQ ID NO 17
<211> LENGTH: 22
<212> TYPE: DNA
<213> ORGANISM: Homo sapiens

<400> SEQUENCE: 17
tccgtgtgta ttccagctcc tg                                               22

<210> SEQ ID NO 18
<211> LENGTH: 21
<212> TYPE: DNA
<213> ORGANISM: Homo sapiens

<400> SEQUENCE: 18
gattgctgcg cgtcgccttt g                                                21

<210> SEQ ID NO 19
<211> LENGTH: 21
<212> TYPE: DNA
<213> ORGANISM: Homo sapiens

<400> SEQUENCE: 19
ccttagatct caccactgga g                                                21

<210> SEQ ID NO 20
<211> LENGTH: 20
<212> TYPE: DNA
<213> ORGANISM: Homo sapiens

<400> SEQUENCE: 20
```

```
catgcgacag gtcactggtg                                        20

<210> SEQ ID NO 21
<211> LENGTH: 22
<212> TYPE: DNA
<213> ORGANISM: Homo sapiens

<400> SEQUENCE: 21
tagtgtttgg ctcaggtcat ac                                     22

<210> SEQ ID NO 22
<211> LENGTH: 20
<212> TYPE: DNA
<213> ORGANISM: Homo sapiens

<400> SEQUENCE: 22
agagtggcca ggtcctgtct                                        20

<210> SEQ ID NO 23
<211> LENGTH: 22
<212> TYPE: DNA
<213> ORGANISM: Homo sapiens

<400> SEQUENCE: 23
cttgcacttc cagctccatc tt                                     22

<210> SEQ ID NO 24
<211> LENGTH: 23
<212> TYPE: DNA
<213> ORGANISM: Homo sapiens

<400> SEQUENCE: 24
tggcttcagg gccttgccta gag                                    23

<210> SEQ ID NO 25
<211> LENGTH: 23
<212> TYPE: DNA
<213> ORGANISM: Homo sapiens

<400> SEQUENCE: 25
acaagcctgg cccaaggctt ggt                                    23

<210> SEQ ID NO 26
<211> LENGTH: 24
<212> TYPE: DNA
<213> ORGANISM: Homo sapiens

<400> SEQUENCE: 26
ctgcccatct ctggttcaga ccat                                   24

<210> SEQ ID NO 27
<211> LENGTH: 23
<212> TYPE: DNA
<213> ORGANISM: Homo sapiens

<400> SEQUENCE: 27
ggagagttgg cttccagacc aga                                    23

<210> SEQ ID NO 28
<211> LENGTH: 22
<212> TYPE: DNA
<213> ORGANISM: Homo sapiens

<400> SEQUENCE: 28
```

```
gtatccatgt ggcagcagga gc                                        22

<210> SEQ ID NO 29
<211> LENGTH: 22
<212> TYPE: DNA
<213> ORGANISM: Homo sapiens

<400> SEQUENCE: 29
cacggaagag ccatgcagcc aa                                        22

<210> SEQ ID NO 30
<211> LENGTH: 26
<212> TYPE: DNA
<213> ORGANISM: Homo sapiens

<400> SEQUENCE: 30
ctatcatgtg cagctcagac caatgg                                    26

<210> SEQ ID NO 31
<211> LENGTH: 27
<212> TYPE: DNA
<213> ORGANISM: Homo sapiens

<400> SEQUENCE: 31
gtctgcaatt taaatagggc cttctgg                                   27

<210> SEQ ID NO 32
<211> LENGTH: 24
<212> TYPE: DNA
<213> ORGANISM: Homo sapiens

<400> SEQUENCE: 32
caaggcagcc tacatgagtc ctgg                                      24

<210> SEQ ID NO 33
<211> LENGTH: 25
<212> TYPE: DNA
<213> ORGANISM: Homo sapiens

<400> SEQUENCE: 33
taacagggct gaatggaatc ctcag                                     25

<210> SEQ ID NO 34
<211> LENGTH: 24
<212> TYPE: DNA
<213> ORGANISM: Homo sapiens

<400> SEQUENCE: 34
ggtgcaggat tctaggagga ctgg                                      24

<210> SEQ ID NO 35
<211> LENGTH: 24
<212> TYPE: DNA
<213> ORGANISM: Homo sapiens

<400> SEQUENCE: 35
catcttgcct cactgccctg ctct                                      24

<210> SEQ ID NO 36
<211> LENGTH: 26
<212> TYPE: DNA
<213> ORGANISM: Homo sapiens
```

-continued

```
<400> SEQUENCE: 36
ttgaccctag tgtctgtgtc cttctg                                          26

<210> SEQ ID NO 37
<211> LENGTH: 24
<212> TYPE: DNA
<213> ORGANISM: Homo sapiens

<400> SEQUENCE: 37
gctgcaggat caaatagcag gtgg                                            24

<210> SEQ ID NO 38
<211> LENGTH: 24
<212> TYPE: DNA
<213> ORGANISM: Homo sapiens

<400> SEQUENCE: 38
tgctcctctc ctctgagcta acag                                            24

<210> SEQ ID NO 39
<211> LENGTH: 23
<212> TYPE: DNA
<213> ORGANISM: Homo sapiens

<400> SEQUENCE: 39
ggaggtgctt ggagatcatt tgg                                             23

<210> SEQ ID NO 40
<211> LENGTH: 23
<212> TYPE: DNA
<213> ORGANISM: Homo sapiens

<400> SEQUENCE: 40
gcttcagtct cacattagcg agg                                             23
```

GENETIC MUTATION UNDERLYING ORTHOSTATIC INTOLERANCE AND DIAGNOSTIC AND THERAPEUTIC METHODS RELATING THERETO

CROSS REFERENCE TO RELATED APPLICATIONS

This application is based on and claims priority to U.S. Provisional Application Ser. No. 60/173,682, filed Dec. 29, 1999, and to U.S. Provisional Application Ser. No. 60/175,456, filed Jan. 11, 2000, each of which are herein incorporated by reference in their entirety.

GRANT STATEMENT

This work was supported by NIH grants MH58921, PO1 HL56693 and RR00095, and by NASA grant NAS 9 19483. Thus, the U.S. Government has certain rights in the invention.

TECHNICAL FIELD

The present invention relates to isolated polynucleotide molecules useful for analyzing novel norepinephrine (NE) transporter variants, to peptides encoded by these molecules, and to the diagnostic and therapeutic uses thereof relating to a newly identified NE transporter polymorphism. Among such uses are methods for determining the susceptibility of a subject to orthostatic intolerance based on an analysis of a biological sample from the subject.

Table of Abbreviations

| | |
|---|---|
| A457P | alanine to proline amino acid mutation of amino acid 457 of the norepinephrine transporter polypeptide |
| ASO | allele-specific oligonucleotide |
| ATP | adenosine triphosphate |
| bp | base pair(s) |
| BP | blood pressure |
| bpm | beats per minute |
| BSA | bovine serum albumin |
| COMT | catechol-O-methyltransferase |
| dbp | diastolic blood pressure |
| DHPG | dihydroxyphenyl glycol |
| Epi | epinephrine |
| fl | full length |
| HAT | hypoxanthine, aminopterin, thymidine |
| HR or hr | heart rate |
| KDa | kilodalton |
| KLH | keyhole limpet hemocyanin |
| l | liter |
| LAT | ligation activated translation |
| LCR | ligase chain reaction |
| MAO | monoamine oxidase |
| MN | metanephrine |
| ml | milliliter(s) |
| mmHg | millimeters of mercury - standard blood pressure unit |
| MSNA | muscle sympathetic nerve activity |
| NAG | n-acetyl glutamate |
| NASDA ™ | nucleic acid sequence-based amplification |
| NE | norepinephrine |
| NET | norepinephrine transporter |
| NMN | normetanephrine |
| NO | nitric oxide |
| NTP | nitroprusside infusion |
| OI | orthostatic intolerance |
| OLA | oligonucleotide ligate assays |
| PBSCT | peripheral blood stem-cell transplantation |
| pg | picogram(s) |
| POTS | postural tachycardia syndrome |
| PCR | polymerase chain reaction |
| RCR | repair chain reaction |
| sbp | systolic blood pressure |
| SSCP | single strand conformation polymorphism |
| SDA | strand displacement activation |
| REF | Restriction endonuclease fingerprinting |

BACKGROUND ART

Orthostatic intolerance (OI) is a syndrome characterized by adrenergic symptoms brought on by upright posture. Usually, there is a heart rate increase of at least 30 bpm on standing without significant orthostatic hypotension. Jacob et al., *Circulation* (1997). Females are disproportionately affected and patients usually present in the second to fourth decade of life. Low et al., *Neurology* (1995). This dysautonomic syndrome is quite common and may have been first described as Da Costa's syndrome more than 100 years ago. Jordan et al., *Chin J. Physiol* (1997); Novak et al., *J Aut N Syst* (1996); Streeten, *Orthostatic Disorders of the Circulation: Mechanisms, Manifestations and Treatment* (1987). It has been re-recognized over the years as soldiers heart, neurocirculatory asthenia, and mitral valve prolapse syndrome. It also bears many similarities to chronic fatigue syndrome. Because of the prominent feature of orthostatic tachycardia, postural tachycardia syndrome (POTS) is a current popular name. Rosen et al., *Am J Med* (1982).

These features and their improvement with salt and volume replacement are consistent with hypovolemia and a secondary sympathetic activation. However, most patients are not hypovolemic. Excessive venous pooling with upright posture, hypersensitivity of veins to alpha-adrenoreceptor agonists and decreased autonomic latencies in the lower extremities are consistent with partial autonomic denervation as another mechanism which could cause secondary sympathetic activation. However, increased heart rate, plasma norepinephrine and muscle sympathetic nerve activity (MSNA) even in the supine position coupled with widely oscillating heart rate with upright posture and disparities among heart rate, plasma norepinephrine and MSNA responses to upright tilt are more consistent with fundamentally disordered autonomic regulation. Novak et al., *J Aut N Syst* (1996); Furlan et al., *Circulation* (1998); Shannon et al., *Circulation* (1998); Puddu et al., *Am Heart J* (1983); Pasternac et al., *Am J Med* (1982); Coghlan et al., *Am J Med* (1979).

Thus far, most explanations of the physiological and biochemical abnormalities in OI have focused on alterations in norepinephrine release (i.e., compensatory, excessive, or disordered). Streeten et al., *J Lab Clin Med* (1988); Furlan et al., *Circulation* (1998); Novak et al., *Stroke* (1998). An alternative explanation is an abnormality in synaptic norepinephrine clearance. Approximately 80–90% of norepinephrine released into many synapses can be cleared by neuronal re-uptake via the presynaptic norepinephrine transporter (NET), while the remaining 10–20% spills over into the circulation or extraneuronal tissue, as disclosed by Esler et al., *Physiol Rev* (1990).

To date, attempts to identify a genetic basis within the NE transporter gene for OI or other NE transport impairment have not been undertaken. It is further noted that drugs inhibiting NET (e.g., cocaine, amphetamines, tricyclic antidepressants) cause features typical of OI (i.e., tachycardia, orthostatic symptoms, and elevated plasma catecholamines). Thus, exploration of impaired NET function, including exploration of a genetic basis for such impaired NET function, would provide important information about the biological and addictive effects of these drugs.

What is needed, then, is further characterization of the structure of the NE transporter gene generally and in OI patients. Since the NE transporter plays a pivotal role in norepinephrine uptake at the synaptic cleft, further characterization of the structure and role of the NE transporter gene would meet a long-felt need in the art for diagnostic and therapeutic methods associated with NE transporter-mediated biological functions.

SUMMARY OF THE INVENTION

A method of screening for sub-optimal NE transporter-mediated physiological responses function in a subject is disclosed. The method comprises: (a) obtaining a biological sample from the subject; and (b) detecting a polymorphism of a NE transporter gene in the biological sample from the subject, the presence of the polymorphism indicating that the susceptibility of the subject to sub-optimal NET-mediated physiological responses. In accordance with a preferred embodiment of the present invention, detection of the polymorphism is employed with respect to determining the susceptibility of a subject to orthostatic intolerance (OI).

Preferably, the polymorphism of the NE transporter polypeptide comprises a G to C transversion in exon 9 of the NE transporter gene. Preferably, the G to C transversion further comprises a change in the triplet code from GCA/GCC/GCG/GCU to CCA/CCC/CCG/CCU, which encodes a NE transporter polypeptide having a proline moiety at amino acid residue 457 instead of an alanine moiety.

Kits and reagents, including oligonucleotides, nucleic acid probes and antibodies suitable for use in carrying out the methods of the present invention and for use in detecting the polypeptides and polynucleotides of the present invention are also disclosed herein. Methods for preparing the polynucleotides and polypeptides of the present invention are also disclosed herein.

In a further embodiment, this invention pertains to diagnostic methods based upon a polymorphism of a NE transporter gene as described herein. Such diagnostic methods include detection of NE transporter deficiencies and disorders related thereto based upon a comparison of NE transporter function related data to data observed in patients having the NE transporter polymorphism disclosed here.

It is therefore an object of the present invention to provide polynucleotide molecules that can be used in analyzing NE transporter genes in vertebrate subjects.

It is also an object of the present invention to provide for the determination of NE transporter genotype in vertebrate subjects and particularly human subjects, based on information obtained through the analysis of nucleic acids, including genomic DNA and cDNA, derived from tissues from the subject.

It is yet another object of the present invention to provide a ready method for determining NE transporter genotype.

It is still a further object of the present invention to provide polypeptide and polynucleotide molecules for use in generating antibodies that distinguish between the different forms of NE transporter which constitute the NE transporter polymorphism.

It is yet a further object of the present invention is to provide methods for diagnosing clinical syndromes related to and associated with the NE transporter polymorphism and/or sub-optimal NE transporter function.

Some of the objects of the invention having been stated hereinabove, other objects will become evident as the description proceeds, when taken in connection with the accompanying Drawings and Examples as best described hereinbelow.

BRIEF DESCRIPTION OF THE DRAWINGS

FIGS. 2A–2F depict evaluation of norepinephrine transporter (NET) mutation. DNA sequencing (FIG. 2A) identified the presence of both C and G nucleotides (arrows) in both the sense and antisense DNA indicating heterozygosity at this locus. This C to G nucleotide change results in an alanine to proline change in amino acid 457 (A457P). FIG. 2B shows the position of the A457P mutation within NET. This mutation occurs in transmembrane domain 9 which is highly conserved among the related murine and bovine NETs and the frog epinephrine transporter (fET) as seen in FIG. 2C. FIG. 2D shows that compared to the wild type NET, the A457P mutation results in significant impairment of NE uptake in transiently transfected Chinese Hamster Ovary cells which is not significantly different from the nonspecific uptake observed in cells transfected with the vector alone. FIGS. 2E and 2F evaluated the presence of the mutant (P) and wild type (A) alleles within the family of the OI proband (arrow).

DETAILED DESCRIPTION OF THE INVENTION

Orthostatic intolerance (OI) is a common syndrome characterized by lightheadedness, palpitations, fatigue, altered mentation, and a syncope and is often accompanied by postural tachycardia and elevated plasma norepinephrine. Previous studies suggest that heart rate and plasma norepinephrine are elevated out of proportion to increase in sympathetic outflow. The cocaine and antidepressant sensitive L-norepinephrine transporter (NET) is responsible for synaptic norepinephrine inactivation.

Figure 4A:
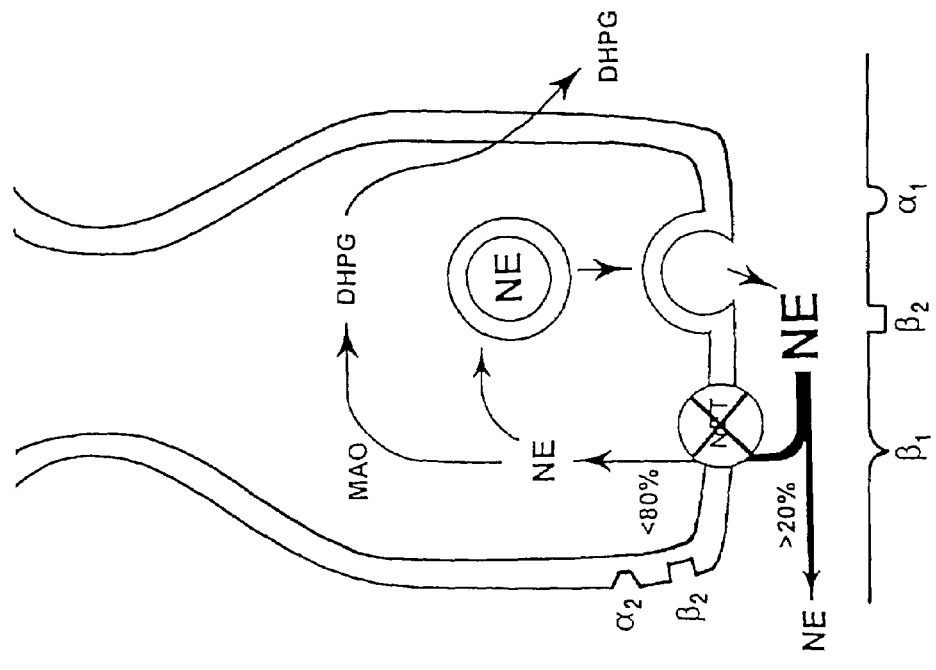
FIG. 4A is a schematic depicting neuronal metabolism of norepinephrine (NE) in normal conditions.

As shown in FIG. 4A, under normal conditions exocytotic release of NE from intraneuronal vesicles into the synaptic space where the amine can interact with post-synaptic and pre-synaptic adrenoreceptors (a). Approximately 80% of the synapic NE is taken up into the neuron by NET. Approximately 20% spills over into the circulation (b). Captured NE is preferentially converted to DHPG by monoamine oxidase (MAO); some is repackaged into synaptic vesicles (c). DHPG diffuses out of the neuron into the circulation (d).

Figure 4B:
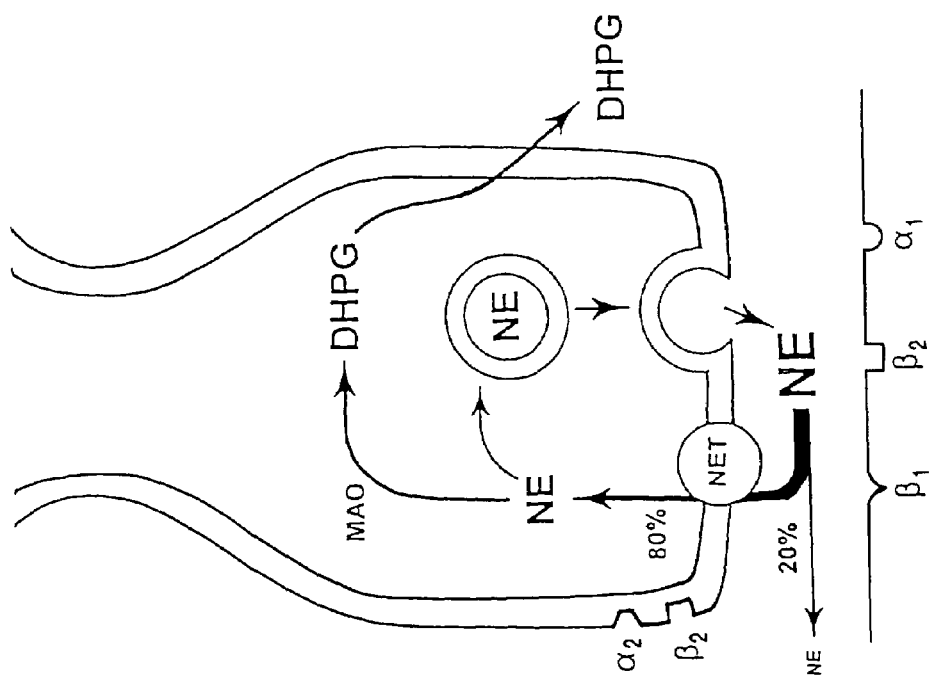
FIG. 4B is a schematic depicting neuronal metabolism of norepinephrine (NE) in NET deficiency conditions.

As shown in FIG. 4B, release of NE into the synaptic space is unaffected (e). Because of decreased NET activity, less than 80% of the synapic NE is taken up into the neuron by NET and the spillover into the circulation is greater than 20%. Also because of decreased NET activity, NE has greater opportunity for interaction with adrenoreceptors (f). Because the reuptake of NE is decreased, DHPG production is decreased (g). Lower DHPG concentration in the neuron results in lower DHPG concentrations in the plasma and, subsequently, a reduced plasma DHPG/NE ration (h).

Whether abnormal NET function might contribute to the pathophysiology of OI, using a battery of bedside physiological, pharmacological, biochemical, and molecular biological tests was tested. In a proband with significant orthostatic symptoms and tachycardia, the present co-inventors found disproportionately elevated plasma norepinephrine with standing, impaired systemic clearance of infused titrated norepinephrine, impaired tyramine responsiveness, and a dissociation between plasma norepinephrine and DHPG elevation. Analysis of the norepinephrine transporter (SCL6A2, referred to herein as the "NE transporter" or "NET") revealed the proband to be a heterozygote for an inactivating coding mutation in exon 9. Analysis of norepinephrine transport activity produced by the mutant cDNA in transfected cells demonstrated greater than 98% reduction in function relative to normal. Presence of the mutant allele in the proband's family segregated with postural tachycardia and alteration in plasma catecholamine homeostasis.

Thus, the present invention pertains to the first identification of a specific genetic defect in OI and to the first identification of a disease linked to a coding alteration in a Na+/Cl– dependent neurotransmitter transporter. The present invention also pertains to the discovery that genetic or acquired deficits in norepinephrine inactivation underlie hyperadrenergic states leading to orthostatic intolerance.

As disclosed herein is the discovery of a polymorphism of the norepinephrine transporter, the transport polypeptide that plays a role in norepinephrine reuptake at the synaptic cleft, among other in vivo roles. Particularly, the polymorphism is characterized by an amino acid substitution, alanine/proline at amino acid 457 in the encoded NE transporter polypeptide.

Also disclosed herein is the observation that a single nucleotide change in the NE transporter gene is responsible for the functional polymorphism of the NE transporter. Particularly, a G to C transversion with exon 9 of the NE transporter gene leads to an A457P change in the encoded NE transporter polypeptide.

In light of these discoveries, manipulation of biological samples derived from vertebrate subjects can be effected to provide for the analysis of NE transporter phenotypes, for the generation of peptides encoded by such nucleic acid molecules, and for diagnostic methods relating to the NE transporter polymorphism. Nucleic acid molecules utilized in these contexts may be amplified, as described below, and generally include RNA, genomic DNA and cDNA derived from RNA.

A. Polynucleotide Screening Techniques

In accordance with one embodiment of the present invention, a method of screening for susceptibility to sub-optimal norepinephrine (NE) transport function resulting in decreased NE clearance in a subject is provided. The method comprising the steps of: (a) obtaining a nucleic acid sample from the subject; and (b) detecting a polymorphism of a norepinephrine transporter ("NE transporter" or "NET") gene in the nucleic acid sample from the subject, the presence of the polymorphism indicating that the susceptibility of the subject to sub-optimal NE transport function, which results in decreased NE transport. In accordance with the present invention, detection of the polymorphism is particularly provided with respect to determining the susceptibility of a subject to orthostatic intolerance (OI).

As used herein and in the claims, the term "polymorphism" refers to the occurrence of two or more genetically determined alternative sequences or alleles in a population. A polymorphic marker is the locus at which divergence occurs. Preferred markers have at least two alleles, each occurring at frequency of greater than 1%. A polymorphic locus may be as small as one base pair.

Useful nucleic acid molecules according to the present invention include those which will specifically hybridize to NE transporter sequences in the region of the G to C transversion at base 237 within exon 9 (GenBank Accession No. x91127, SEQ ID NO:15) of the NE transporter gene, changing the triplet code from GCA or GCC or GCG or GCU to CCA or CCC or CCG or CCU. This transversion leads to the A457P change in the encoded NE transporter polypeptide. Typically these are at least about 20 nucleotides in length and have the nucleotide sequence corresponding to the region of the G to C transversion in a cDNA (e.g. SEQ ID NO:3) encoding a NE transporter polypeptide and including exon 9 of the NE transporter gene. The cDNA sequence set forth in SEQ ID NO:1 is referred to herein as a NE transporter "consensus sequence". The term "consensus sequence", as used herein, is meant to refer to a nucleic acid or protein sequence for NET, the nucleic or amino acids of which are known to occur with high frequency in a population of individuals who carry the gene which codes for a normally functioning protein, or which nucleic acid itself has normal function.

Provided nucleic acid molecules can be labeled according to any technique known in the art, such as with radiolabels, fluorescent labels, enzymatic labels, sequence tags, etc. According to another aspect of the invention, the nucleic acid molecules contain the G to C transversion of exon 9. Such molecules can be used as allele-specific oligonucleotide probes to track a particular mutation, for example, through a family of subjects.

Body samples can be tested to determine whether the NE transporter gene contains the G to C transversion of exon 9. Suitable body samples for testing include those comprising DNA, RNA or protein obtained from biopsies, including liver and intestinal tissue biopsies; or from blood, prenatal; or embryonic tissues, for example.

In one embodiment of the invention a pair of isolated oligonucleotide primers are provided: RB655 (SEQ ID NO:32) and RB667(SEQ ID NO:33). These primers are derived from NE transporter exon 9 (the location of the polymorphism of the present invention), and amplify a yield a 448 base pair (bp) product. Other primers are also derived from NE transporter exon 9 (the location of the polymorphism of the present invention, GenBank Accession No. x91127, SEQ ID NO:15). The oligonucleotide primers are useful in diagnosis of a subject at risk for impaired or sub-optimal NET function and orthostatic intolerance. The primers direct amplification of a target polynucleotide prior to sequencing. These unique NE transporter exon 9 oligonucleotide primers were designed and produced based upon identification of the G to C transversion in exon 9.

In another embodiment of the invention isolated allele specific oligonucleotides (e.g. SEQ ID NOS: 9 & 10) are provided. Sequences substantially similar thereto are also provided in accordance with the present invention. The allele specific oligonucleotides are useful in diagnosis of a subject at risk for impaired or sub-optimal NET function. These unique NE transporter exon 9 oligonucleotide primers were designed and produced based upon identification of the G to C transversion in exon 9.

The terms "substantially complementary to" or "substantially the sequence of" refer to sequences which hybridize to the sequences provided (e.g. SEQ ID NOs: 9 and 10) under stringent conditions and/or sequences having sufficient homology with any of SEQ ID NOs: 9 and 10, such that the allele specific oligonucleotides of the invention hybridize to the sequence. The term "isolated" as used herein includes oligonucleotides substantially free of other nucleic acids, proteins, lipids, carbohydrates or other materials with which they may be associated, such association being either in cellular material or in a synthesis medium. A "target polynucleotide" or "target nucleic acid" refers to the nucleic acid sequence of interest e.g., a NE transporter-encoding polynucleotide. Other primers which can be used for primer hybridization are readily ascertainable to those of skill in the art based upon the disclosure herein of the NE transporter polymorphism.

The primers of the invention embrace oligonucleotides of sufficient length and appropriate sequence so as to provide initiation of polymerization on a significant number of nucleic acids in the polymorphic locus (See FIG. 2). Specifically, the term "primer" as used herein refers to a sequence comprising two or more deoxyribonucleotides or ribonucleotides, preferably more than three, and more preferably more than eight and most preferably at least about 20 nucleotides of the NE transporter gene wherein the DNA sequence contains the G to C transversion within to NE transporter exon 9. The allele including guanosine (G) within NE transporter exon 9 is referred to herein as the "NET-a allele", the "A457 allele", or the "alanine-encoding allele". The allele including cytosine (C) within NE transporter exon 9 is referred to herein as the "NET-b allele", the "P457 allele", or the "proline-encoding allele".

An oligonucleotide that distinguishes between the NET-a and the NET-b alleles of the NE transporter gene, wherein the oligonucleotide hybridizes to a portion of the NE transporter gene that includes nucleotide 237 of exon 9 of the NE transporter gene when the nucleotide 237 is cytosine, but does not hybridize with the portion of the NE transporter gene when the nucleotide 237 is guanosine is also provided in accordance with the present invention. An oligonucleotide that distinguishes between the NET-a and the NET-b alleles of the NE transporter gene, wherein the oligonucleotide hybridizes to a portion of the NE transporter gene that includes nucleotide 237 of exon 9 of the NE transporter gene when the nucleotide 237 is guanosine, but does not hybridize with the portion of the NE transporter gene when the nucleotide 237 is cytosine is also provided in accordance with the present invention. Such oligonucleotides are preferably between ten and thirty bases in length. Such oligonucleotides can optionally further comprise a detectable label.

Environmental conditions conducive to synthesis include the presence of nucleoside triphosphates and an agent for polymerization, such as DNA polymerase, and a suitable temperature and pH. The primer is preferably single stranded for maximum efficiency in amplification, but can be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it can contain fewer nucleotides.

Primers of the invention are designed to be "substantially" complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the transversion to hybridize therewith and permit amplification of the genomic locus.

Oligonucleotide primers of the invention are employed in the amplification method which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention can be prepared using any suitable method, such as conventional phosphotriester and phosphodiester methods or automated embodiments thereof. In one such automated embodiment, diethylphosphoramidites are used as starting materials and can be synthesized as described by Beaucage et al., *Tetrahedron Letters* 22:1859–1862 (1981). One method for synthesizing oligonucleotides on a modified solid support is described in U.S. Pat. No. 4,458,066.

Any nucleic acid specimen, in purified or non-purified form, can be utilized as the starting nucleic acid or acids, providing it contains, or is suspected of containing, a nucleic acid sequence containing the polymorphic locus. Thus, the method can amplify, for example, DNA or RNA, including messenger RNA, wherein DNA or RNA can be single stranded or double stranded. In the event that RNA is to be used as a template, enzymes, and/or conditions optimal for reverse transcribing the template to DNA would be utilized. In addition, a DNA-RNA hybrid which contains one strand of each can be utilized. A mixture of nucleic acids can also be employed, or the nucleic acids produced in a previous amplification reaction herein, using the same or different primers can be so utilized. The specific nucleic acid sequence to be amplified, i.e., the polymorphic locus, can be a fraction of a larger molecule or can be present initially as a discrete molecule, so that the specific sequence constitutes the entire nucleic acid. It is not necessary that the sequence to be amplified be present initially in a pure form; it can be a minor fraction of a complex mixture, such as contained in whole human DNA.

DNA utilized herein can be extracted from a body sample, such as blood, tissue material, preferably white blood cells, and the like by a variety of techniques such as that described by Maniatis et. al. in *Molecular Cloning: A Laboratory Manual*, Cold Spring Harbor, N.Y., p 280–281 (1982). If the extracted sample is impure, it can be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90–100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization can also be added together with the other reagents if it is heat stable. This synthesis (or amplification) reaction can occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization can be any compound or system which will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the method. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. *PCR. A Practical Approach*, ILR Press, Eds. McPherson et al. (1992).

The amplification products can be detected by Southern blot analysis with or without using radioactive probes. In one such method, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as dideoxy sequencing, PCR, oligomer restriction (Saiki et al., *Bio/Technology* 3:1008–1012 (1985), allele-specific oligonucleotide (ASO) probe analysis (Conner et al., *Proc. Natl. Acad. Sci. U.S.A.* 80:278 (1983), oligonucleotide ligation assays (OLAs) (Landgren et. al., *Science* 241:1007, 1988), and the like. Molecular techniques for DNA analysis have been reviewed (Landgren et. al., *Science* 242:229–237, 1988).

Preferably, the method of amplifying is by PCR, as described herein and in U.S. Pat. Nos. 4,683,195; 4,683,202; and 4,965,188 each of which is hereby incorporated by reference; and as is commonly used by those of ordinary skill in the art. Alternative methods of amplification have been described and can also be employed as long as the NE transporter locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA.

Another nucleic acid amplification technique is nucleic acid sequence-based amplification (NASBA™) which uses reverse transcription and T7 RNA polymerase and incorporates two primers to target its cycling scheme. NASBA™ amplification can begin with either DNA or RNA and finish with either, and amplifies to about $10^8$ copies within 60 to 90 minutes.

Alternatively, nucleic acid can be amplified by ligation activated transcription (LAT). LAT works from a single-stranded template with a single primer that is partially single-stranded and partially double-stranded. Amplification is initiated by ligating a cDNA to the promoter olignucleotide and within a few hours, amplification is about $10^8$ to about $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest.

Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligo probe pairs, and the RCR fills and joins the gap, mimicking normal DNA repair.

Nucleic acid amplification by strand displacement activation (SDA) utilizes a short primer containing a recognition site for HincII with short overhang on the 5' end which binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the cite of the nick and begins to polymerize, displacing the initial primer strand downstream and building a new one which serves as more primer.

SDA produces greater than about a $10^7$-fold amplification in 2 hours at 37° C. Unlike PCR and LCR, SDA does not require instrumented temperature cycling. Another amplification system useful in the method of the invention is the QB Replicase System. Although PCR is the preferred method of amplification if the invention, these other methods can also be used to amplify the NE transporter locus as described in the method of the invention. Thus, the term "amplification technique" as used herein and in the claims is meant to encompass all the foregoing methods.

In another embodiment of the invention a method is provided for diagnosing or identifying a subject having a predisposition or higher susceptibility to (at risk of) impaired sub-optimal NET function, comprising sequencing a target nucleic acid of a sample from a subject by dideoxy sequencing, preferably following amplification of the target nucleic acid.

In another embodiment of the invention a method is provided for diagnosing a subject having a predisposition or higher susceptibility to (at risk of) impaired sub-optimal NET function, comprising contacting a target nucleic acid of a sample from a subject with a reagent that detects the presence of the NE transporter polymorphism and detecting the reagent.

Another method comprises contacting a target nucleic acid of a sample from a subject with a reagent that detects the presence of the G to C transversion at base 237, within exon 9, and detecting the transversion. A number of hybridization methods are well known to those skilled in the art. Many of them are useful in carrying out the invention.

The materials for use in the method of the invention are ideally suited for the preparation of a diagnostic kit. Such a kit can comprise a carrier being compartmentalized to receive in close confinement one or more containers such as vials, tubes, and the like, each of the container comprising one of the separate elements to be used in the method. For example, one of the containers can comprise a reagent or reagents for amplifying NE transporter DNA, the reagent or reagents comprising the necessary enzyme(s) and oligonucleotide primers for amplifying said target DNA from the subject.

The oligonucleotide primers include primers having a sequence of NET exon 9 selected from the group including, but not limited to: SEQ ID NO:15, or primer sequences substantially complementary or substantially homologous thereto. The target flanking 5' and 3' polynucleotide sequence of NET exon 9 has substantially the sequence set forth in SEQ ID NO:15, and sequences substantially complementary or homologous thereto. Other oligonucleotide primers for amplifying NE transporter are readily ascertainable to those of skill in the art given the disclosure of the present invention presented herein.

A kit in accordance with the present invention can further comprise a reagent or reagents for extracting a nucleic acid sample from a biological sample obtained from a subject. Any such reagent or reagents as would be readily apparent to one of ordinary skill in the art falls within the scope of the present invention. By way of particular example, a suitable lysis buffer for the tissue along with a suspension of glass beads for capturing the nucleic acid sample and an elution buffer for eluting the nucleic acid sample off of the glass beads comprise means for extracting a nucleic acid sample from a biological sample obtained from a subject.

Other examples include commercially available, such as the GENOMIC ISOLATION KIT A.S.A.P.™ (Boehringer Mannheim, Indianapolis, Ind.), Genomic DNA Isolation System (GIBCO BRL, Gaithersburg, Md.), ELU-QUIK™ DNA Purification Kit (Schleicher & Schuell, Keene, N.H.), DNA Extraction Kit (Stratagene, La Jolla, Calif.), TURBO-GEN™ Isolation Kit (Invitrogen, San Diego, Calif.), and the like. Use of these kits according to the manufacturer's instructions is generally acceptable for purification of DNA prior to practicing the methods of the present invention.

B. Definitions Affecting NE Transporter-Encoding Polynucleotide and NET Transporter Polypeptides Encoded by Same In accordance with the present invention, purified and isolated NE transporter-encoding polynucleotides and NE transporter polypeptides encoded by same are provided. A particularly provided NE transporter-encoding polynucleotide comprises a NE transporter encoding polynucleotide which includes a G to C transversion at base 237 within exon 9 of the NE transporter gene which changes the triplet code from GCA or GCC or GCG or GCU to CCA or CCC or CCG or CCU and leads to the A457P change in the encoded NE transporter polypeptide. The encoded NE transporter polypeptide comprising the A457P change is also particularly provided. Thus, allelic variant polynucleotides and polypeptides encoded by same are provided in accordance with the present invention. Further, a biologically active NE transporter polypeptide is also provided in accordance with the present invention, as is a NE transporter-encoding polynucleotide encoding such a NE transporter polypeptide. Exemplary biological activities include the biological activity of mediating NE uptake and the biological activity of cross-reacting with an anti-NE transporter antibody.

The provided NE transporter-encoding polynucleotides and polypeptides have broad utility given the biological significance of NE uptake, as is known in the art. By way of example, the NE transporter-encoding polynucleotides and polypeptides are useful in the preparation of screening assays and assay kits that are used to detect the presence of the proteins and nucleic acids of this invention in biological samples, and in the detection and analysis of polymorphic sequences and polypeptides encoded by such sequences, as disclosed herein.

Preferably, the provided NE transporter polynucleotides and polypeptides are isolated from vertebrate and invertebrate sources. Thus, homologs of NE transporter, including, but not limited to, mammalian, yeast and bacterial homologs are provided in accordance with the present invention. Preferred mammalian homologs of NE transporter members include, but are not limited to, bovine, rat, mouse and human homologs.

The terms "NE transporter gene product", "NE transporter protein" and "NE transporter polypeptide" refer to proteins having amino acid sequences which are substantially identical to the native amino acid sequences in NE transporter and which are biologically active in that they are capable of mediating NE uptake, or cross-reacting with anti-NE transporter antibodies raised against a NE transporter polypeptide.

The terms "NE transporter gene product", "NE transporter protein" and "NE transporter polypeptide" also include analogs of NE transporter molecules which exhibit at least some biological activity in common with native NE transporter gene products. Furthermore, those skilled in the art of mutagenesis will appreciate that other analogs, as yet undisclosed or undiscovered, can be used to construct NE transporter analogs. There is no need for an "NE transporter gene product", "NE transporter protein" or "NE transporter polypeptide" to comprise all, or substantially all of the amino acid sequence of a native NE transporter gene product. Shorter or longer sequences are anticipated to be of use in the invention. Thus, the term "NE transporter gene product" also includes fusion or recombinant NE transporter polypeptides and proteins. Methods of preparing such proteins are described herein.

The terms "NE transporter-encoding polynucleotide", "NE transporter gene", "NE transporter gene sequence" and "NE transporter gene segment" refer to any DNA sequence that is substantially identical to a polynucleotide sequence encoding a NE transporter gene product, NE transporter protein or NE transporter polypeptide as defined above. The terms also refer to RNA, or antisense sequences, compatible with such DNA sequences. A "NE transporter-encoding polynucleotide", "NE transporter gene", "NE transporter gene sequence" and "NE transporter gene segment" can also comprise any combination of associated control sequences.

The term "substantially identical", when used to define either a NE transporter gene product or NE transporter amino acid sequence, or a NE transporter gene or NE transporter nucleic acid sequence, means that a particular sequence, for example, a mutant sequence, varies from the sequence of a natural NE transporter by one or more deletions, substitutions, or additions, the net effect of which is to retain at least some of biological activity of NE transporter. Alternatively, DNA analog sequences are "substantially identical" to specific DNA sequences disclosed herein if: (a) the DNA analog sequence is derived from coding regions of the natural NE transporter gene; or (b) the DNA analog sequence is capable of hybridization of DNA sequences of (a) under moderately stringent conditions and which encode biologically active NE transporter gene product; or (c) the DNA sequences are degenerative as a result of the genetic code to the DNA analog sequences defined in (a) and/or (b). Substantially identical analog proteins will be greater than about 60% identical to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences.

B.1. Percent Similarity

Percent similarity can be determined, for example, by comparing sequence information using the GAP computer program, available from the University of Wisconsin Geneticist Computer Group. The GAP program utilizes the alignment method of Needleman et al., *J. Mol. Biol.* 48:443 (1970), as revised by Smith et al., *Adv. Appl. Math.* 2:482 (1981). Briefly, the GAP program defines similarity as the number of aligned symbols (i.e. nucleotides or amino acids) which are similar, divided by the total number of symbols in the shorter of the two sequences. The preferred default parameters for the GAP program include: (1) a unitary comparison matrix (containing a value of 1 for identities and 0 for non-identities) of nucleotides and the weighted comparison matrix of Gribskov et al., *Nucl. Acids. Res.* 14:6745 (1986), as described by Schwartz et al., eds., *Atlas of Protein Sequence and Structure*, National Biomedical Research Foundation, pp.357–358 (1979); (2) a penalty of 3.0 for each gap and an additional 0.01 penalty for each symbol and each gap; and (3) no penalty for end gaps. Other comparison techniques are described in the Examples.

The term "homology" describes a mathematically based comparison of sequence similarities which is used to identify genes or proteins with similar functions or motifs. Accordingly, the term "homology" is synonymous with the term "similarity" and "percent similarity" as defined above. Thus, the phrases "substantial homology" or "substantial similarity" have similar meanings.

B.2. Nucleic Acid Sequences

In certain embodiments, the invention concerns the use of NE transporter genes and gene products that include within their respective sequences a sequence which is essentially that of a NE transporter gene, or the corresponding protein. The term "a sequence essentially as that of a NE transporter gene", means that the sequence substantially corresponds to a portion of a NE transporter polypeptide or NE transporter encoding polynucleotide and has relatively few bases or amino acids (whether DNA or protein) which are not identical to those of a NE transporter protein or NE transporter gene, (or a biologically functional equivalent of, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of a NE transporter protein or NE transporter gene, will be sequences which are "essentially the same".

NE transporter gene products and NE transporter genes which have functionally equivalent codons are also covered by the invention. The term "functionally equivalent codon" is used herein to refer to codons that encode the same amino acid, such as the ACG and AGU codons for serine. Thus, when referring to the sequence examples presented in SEQ ID NO's:1–4 and 11–14, applicants provide substitution of functionally equivalent codons of Table 1 into the sequence examples of SEQ ID NO's:1–4 and 11–14. Thus, applicants are in possession of amino acid and nucleic acids sequences which include such substitutions but which are not set forth herein in their entirety for convenience.

TABLE 1

Table of the Genetic Code

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |

TABLE 1-continued

Table of the Genetic Code

| Amino Acids | | | Codons |
| --- | --- | --- | --- |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and nucleic acid sequences can include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which can, for example, include various non-coding sequences flanking either of the 5' or 3' portions of the coding region or can include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are base-pairing according to the standard Watson-Crick complementarity rules. As used herein, the term "complementary sequences" means nucleic acid sequences which are substantially complementary, as can be assessed by the same nucleotide comparison set forth above, or as defined as being capable of hybridizing to the nucleic acid segment in question under relatively stringent conditions such as those described herein. A particular example of a provided complementary nucleic acid segment is an antisense oligonucleotide.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. (See e.g., Wetmur & Davidson, *J. Mol. Biol.* 31:349–370 (1968)).

Probe sequences can also hybridize specifically to duplex DNA under certain conditions to form triplex or other higher order DNA complexes. The preparation of such probes and suitable hybridization conditions are well known in the art.

As used herein, the term "DNA segment" refers to a DNA molecule which has been isolated free of total genomic DNA of a particular species. Furthermore, a DNA segment encoding a NE transporter polypeptide refers to a DNA segment which contains NE transporter coding sequences, yet is isolated away from, or purified free from, total genomic DNA of a source species, such as *Homo sapiens*. Included within the term "DNA segment" are DNA segments and smaller fragments of such segments, and also recombinant vectors, including, for example, plasmids, cosmids, phages, viruses, and the like.

Similarly, a DNA segment comprising an isolated or purified NE transporter gene refers to a DNA segment including NE transporter coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, the NE transporter gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a NE transporter polypeptide that includes within its amino acid sequence an amino acid sequence of any of SEQ ID NOs:2, 4, 12 and 14. In other particular embodiments, the invention concerns isolated DNA segments and recombinant vectors incorporating DNA sequences which encode a protein that includes within its amino acid sequence the amino acid sequence of a NE transporter polypeptide corresponding to human tissues.

It will also be understood that this invention is not limited to the particular nucleic acid and amino acid sequences of SEQ ID NO's:1–4 and 11–14. Recombinant vectors and isolated DNA segments can therefore variously include the NE transporter polypeptide-encoding region itself, include coding regions bearing selected alterations or modifications in the basic coding region, or include encoded larger polypeptides which nevertheless include NE transporter polypeptide-encoding regions or can encode biologically functional equivalent proteins or peptides which have variant amino acid sequences.

In certain embodiments, the invention concerns isolated DNA segments and recombinant vectors which encode a protein or peptide that includes within its amino acid sequence an amino acid sequence essentially as set forth in any of SEQ ID NOs:2, 4, 12 and 14. Naturally, where the DNA segment or vector encodes a full length NE transporter gene product, the most preferred nucleic acid sequence is that which is essentially as set forth in any of SEQ ID NOs: 1, 3, 11 and 13 and which encode a protein that exhibits NE uptake-modulating activity, as can be determined by, for example, assays to detect NE uptake, as disclosed herein in the Examples.

The term "a sequence essentially as set forth in any of SEQ ID NO:2, 4, 12 and 14" means that the sequence substantially corresponds to a portion an amino acid sequence either of SEQ ID NOs:2, 4, 12 and 14 and has relatively few amino acids which are not identical to, or a biologically functional equivalent of, the amino acids of an amino acid sequence of any of SEQ ID NOs:2, 4, 12 and 14. The term "biologically functional equivalent" is well understood in the art and is further defined in detail herein. Accordingly, sequences, which have between about 70% and about 80%; or more preferably, between about 81% and about 90%; or even more preferably, between about 91% and about 99%; of amino acids which are identical or functionally equivalent to the amino acids in any of SEQ ID NOs: 2, 4, 12 and 14, will be sequences which "a sequence essentially as set forth in SEQ ID NOs:2, 4, 12 and 14".

In particular embodiments, the invention concerns gene therapy methods that use isolated DNA segments and recombinant vectors incorporating DNA sequences which encode a protein that includes within its amino acid sequence an amino acid sequence of any of SEQ ID NOs:2, 4, 12 and 14, SEQ ID NOs:2, 4, 12 and 14 including sequences which are derived from human tissue. In other particular embodiments, the invention concerns isolated DNA sequences and recombinant DNA vectors incorporating DNA sequences which encode a protein that includes within its amino acid sequence the amino acid sequence of the NE transporter protein from human hepatic tissue.

In certain other embodiments, the invention concerns isolated DNA segments and recombinant vectors that include within their sequence a nucleic acid sequence essentially as set forth in any of SEQ ID NO:1, 3, 11 and 13. The term "a sequence essentially as set forth in any of SEQ ID NO:1, 3, 11 and 13" is used in the same sense as described above and means that the nucleic acid sequence substantially corresponds to a portion of any of SEQ ID NOs:1, 3, 11 and 13, respectively, and has relatively few codons which are not identical, or functionally equivalent, to the codons of any of SEQ ID NOs:1, 3, 11 and 13, respectively. Again, DNA segments which encode gene products exhibiting NE transport activity, cross-reactivity with an anti-NE transporter antibody, or other biological activity of the NE transporter gene product will be most preferred. The term "functionally equivalent codon" is used herein to refer to codons that encode the same amino acid, such as the six codons for arginine or serine, and also to refer to codons that encode biologically equivalent amino acids (see Table 1).

The nucleic acid segments of the present invention, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. It is therefore provided that a nucleic acid fragment of almost any length can be employed, with the total length preferably being limited by the ease of preparation and use in the intended recombinant DNA protocol. For example, nucleic acid fragments can be prepared which include a short stretch complementary to a nucleic acid sequence set for in any of SEQ ID NOs:1, 3, 11 and 13 respectively, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also useful.

The DNA segments of the present invention encompass biologically functional equivalent NE transporter proteins and peptides. Such sequences can rise as a consequence of codon redundancy and functional equivalency which are known to occur naturally within nucleic acid sequences and the proteins thus encoded. Alternatively, functionally equivalent proteins or peptides can be created via the application of recombinant DNA technology, in which changes in the protein structure can be engineered, based on considerations of the properties of the amino acids being exchanged, e.g. substitution of Ile and Leu at amino acid 2 in SEQ ID NOs:11–14. Changes designed by man can be introduced through the application of site-directed mutagenesis techniques, e.g., to introduce improvements to the antigenicity of the protein or to test NE transporter mutants in order to examine NE transport activity, or other activity at the molecular level.

If desired, one can also prepare fusion proteins and peptides, e.g., where the NE transporter coding region is aligned within the same expression unit with other proteins or peptides having desired functions, such as for purification or immunodetection purposes (e.g., proteins which can be purified by affinity chromatography and enzyme label coding regions, respectively).

Recombinant vectors form important further aspects of the present invention. Particularly useful vectors are those vectors in which the coding portion of the DNA segment is positioned under the control of a promoter. The promoter can be in the form of the promoter which is naturally associated with the NE transporter gene, e.g., in mammalian tissues, as can be obtained by isolating the 5' non-coding sequences located upstream of the coding segment or exon, for example, using recombinant cloning and/or PCR technology, in connection with the compositions disclosed herein.

In other embodiments, certain advantages will be gained by positioning the coding DNA segment under the control of a recombinant, or heterologous, promoter. As used herein, a recombinant or heterologous promoter is intended to refer to a promoter that is not normally associated with a NE transporter gene in its natural environment. Such promoters can include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al., 1989, incorporated herein by reference. The promoters employed can be constitutive, or inducible, and can be used under the appropriate conditions to direct high level expression of the introduced DNA segment, such as is advantageous in the large-scale production of recombinant proteins or peptides. Appropriate promoter systems provided for use in high-level expression include, but are not limited to, the vaccina virus promoter and the baculovirus promoter.

In an alternative embodiment, the present invention provides an expression vector comprising a polynucleotide that encodes a NE transporter polypeptide having NE transport activity, cross-reacting with an anti-NE transporter antibody, or other biological activity in accordance with the present invention. Also preferably, an expression vector of the present invention comprises a polynucleotide that encodes a human NE transporter gene product. More preferably, an expression vector of the present invention comprises a polynucleotide that encodes a polypeptide comprising an amino acid residue sequence of any of SEQ ID NOs:2, 4, 12 and 14. More preferably, an expression vector of the present invention comprises a polynucleotide comprising the nucleotide base sequence of any of SEQ ID NO:1, 3, 11 and 13.

Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a NE transporter polypeptide having NE transport activity, cross-reactivity with an anti-NE transporter antibody, or other biological activity in accordance with the present invention. SEQ ID NO's: 1–4 and 11–14 set forth nucleotide and amino acid sequences from an exemplary vertebrate, human. Also provided by the present invention are homologous or biologically equivalent polynucleotides and NE transporter polypeptides found in other vertebrates, including bovine, mouse and rat.

Preferably, a recombinant host cell of the present invention is transfected with the polynucleotide that encodes human NE transporter polypeptide. More preferably, a recombinant host cell of the present invention is transfected with the polynucleotide sequence of any of SEQ ID NOs:1, 3, 11 and 13. Even more preferably, a host cell of the invention is a eukaryotic host cell. Still more preferably, a recombinant host cell of the present invention is a vertebrate cell. Preferably, a recombinant host cell of the invention is a mammalian cell.

In another aspect, a recombinant host cell of the present invention is a prokaryotic host cell. Preferably, a recombinant host cell of the invention is a bacterial cell, preferably a strain of *Escherichia coli*. More preferably, a recombinant host cell comprises a polynucleotide under the transcriptional control of regulatory signals functional in the recombinant host cell, wherein the regulatory signals appropriately control expression of the NE transporter polypeptide in a manner to enable all necessary transcriptional and post-transcriptional modification.

In yet another embodiment, the present invention provides a method of preparing a NE transporter polypeptide comprising transfecting a cell with polynucleotide that encodes a NE transporter polypeptide having NE transport activity, cross-reacting with an anti-NE transporter antibody, or other biological activity in accordance with the present invention, to produce a transformed host cell; and maintaining the transformed host cell under biological conditions sufficient for expression of the polypeptide. More preferably, the transformed host cell is a eukaryotic cell. More preferably still, the eukaryotic cell is a vertebrate cell. Alternatively, the host cell is a prokaryotic cell. More preferably, the prokaryotic cell is a bacterial cell of *Escherichia coli*. Even more preferably, a polynucleotide transfected into the transformed cell comprises a nucleotide base sequence of any of SEQ ID NOs:1, 3, 11 and 13. SEQ ID NO's:1–4 and 11–14 set forth nucleotide and amino acid sequences for an exemplary vertebrate, human. Also provided by the present invention are homologues or biologically equivalent NE transporter polynucleotides and polypeptides found in other vertebrates, particularly warm blooded vertebrates, and more particularly bovine, mouse and rat.

As mentioned above, in connection with expression embodiments to prepare recombinant NE transporter proteins and peptides, it is provided that longer DNA segments will most often be used, with DNA segments encoding the entire NE transporter protein, functional domains or cleavage products thereof, being most preferred. However, it will be appreciated that the use of shorter DNA segments to direct the expression of NE transporter peptides or epitopic core regions, such as can be used to generate anti-NE transporter antibodies, also falls within the scope of the invention.

DNA segments which encode peptide antigens from about 15 to about 50 amino acids in length, or more preferably, from about 15 to about 30 amino acids in length are particularly useful. DNA segments encoding peptides will generally have a minimum coding length in the order of about 45 to about 150, or to about 90 nucleotides. DNA segments encoding full length proteins can have a minimum coding length on the order of about 4,500 to about 4,600 nucleotides for a protein in accordance with any of SEQ ID NOs: 2, 4, 12 and 14.

Naturally, the present invention also encompasses DNA segments which are complementary, or essentially complementary, to the sequences set forth in any of SEQ ID NO's: 1, 3, 11 and 13. The terms "complementary" and "essentially complementary" are defined above. Excepting intronic or flanking regions, details of which are disclosed graphically in FIG. 2, and allowing for the degeneracy of the genetic code, sequences which have between about 70% and about 80%; or more preferably, between about 81% and about 90%; or even more preferably, between about 91% and about 99%; of nucleotides which are identical or functionally equivalent (i.e. encoding the same amino acid) of nucleotides in any of SEQ ID NOs:1, 3, 11 and 13 will be sequences which are "a sequence essentially as set forth in any of SEQ ID NOs:1, 3, 11 and 13". Sequences which are essentially the same as those set forth in any of SEQ ID NOs:1, 3, 11 and 13 can also be functionally defined as sequences which are capable of hybridizing to a nucleic acid segment containing the complement in any of SEQ ID NOs:1, 3, 11 and 13 under relatively stringent conditions. Suitable relatively stringent hybridization conditions are described herein and will be well known to those of skill in the art.

B.3. Biologically Functional Equivalents

As mentioned above, modification and changes can be made in the structure of the NE transporter proteins and peptides described herein and still obtain a molecule having like or otherwise desirable characteristics. For example, certain amino acids can be substituted for other amino acids in a protein structure without appreciable loss of interactive capacity with structures such as, for example, in the nucleus of a cell. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). Thus, various changes can be made in the sequence of the NE transporter proteins and peptides (or underlying DNA) without appreciable loss of their biological utility or activity.

It is also well understood by the skilled artisan that, inherent in the definition of a biologically functional equivalent protein or peptide, is the concept that there is a limit to the number of changes that can be made within a defined portion of the molecule and still result in a molecule with an acceptable level of equivalent biological activity. Biologically functional equivalent peptides are thus defined herein as those peptides in which certain, not most or all, of the amino acids can be substituted. Of course, a plurality of distinct proteins/peptides with different substitutions can easily be made and used in accordance with the invention.

It is also well understood that where certain residues are shown to be particularly important to the biological or structural properties of a protein or peptide, e.g., residues in active sites, such residues can not generally be exchanged. This is the case in the present invention, where if any changes, for example, in the phosphorylation domains of a NE transporter polypeptide, could result in a loss of an aspect of the utility of the resulting peptide for the present invention.

Amino acid substitutions, such as those which might be employed in modifying the NE transporter proteins and peptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, *J. Mol. Biol.* 157:105–132 (1982), incorporated herein by reference). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

B.4. Sequence Modification Techniques

Modifications to the NE transporter proteins and peptides described herein can be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is preferred, with about 5 to 10 residues on both sides of the junction of the sequence being altered.

In general, the technique of site-specific mutagenesis is well known in the art as exemplified by publications (e.g., Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes, for example, a human NE transporter polypeptide. An oligonucleotide primer bearing the desired mutated sequence is prepared, generally synthetically, for example by the method of Crea et al. (1978). This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected gene using site-directed mutagenesis is provided as a means of producing potentially useful NE transporter polypeptide or other species having NE transport activity and is not meant to be limiting as there are other ways in which sequence variants of these peptides can be obtained. For example, recombinant vectors encoding the desired genes can be treated with mutagenic agents to obtain sequence variants (see, e.g., a method described by Eichenlaub, 1979) for the mutagenesis of plasmid DNA using hydroxylamine.

B.5. Other Structural Equivalents

In addition to the NE transporter peptidyl compounds described herein, the inventors also provide that other sterically similar compounds can be formulated to mimic the key portions of the peptide structure. Such compounds can be used in the same manner as the peptides of the invention and hence are also functional equivalents. The generation of a structural functional equivalent can be achieved by the techniques of modeling and chemical design known to those of skill in the art. It will be understood that all such sterically similar constructs fall within the scope of the present invention.

C. Introduction of Gene Products

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the NE transporter gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One can also desire to incorporate into the transcriptional unit of the vector an appropriate polyadenylation site (e.g., 5'-AATAAA-3'), if one was not contained within the original inserted DNA. Typically, these polyA addition sites are placed about 30 to 2000 nucleotides "downstream" of the coding sequence at a position prior to transcription termination.

While use of the control sequences of the specific gene (i.e., a NE transporter promoter for a NE transporter gene) will be preferred, there is no reason why other control sequences could not be employed, so long as they are compatible with the genotype of the cell being treated. Thus, one can mention other useful promoters by way of example, including, e.g., an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Techniques for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

For introduction of, for example, the human NE transporter gene including allelic variations thereof, it is proposed that one will desire to preferably employ a vector construct that will deliver the desired gene to the affected cells. This will, of course, generally require that the construct be delivered to the targeted cells, for example, mammalian cardiac cells. It is proposed that this can be achieved most preferably by introduction of the desired gene through the use of a viral vector to carry the NE transporter sequence to efficiently infect the cells. These vectors will preferably be an adenoviral, a retroviral, a vaccinia viral vector or adeno-associated virus. These vectors are preferred because they have been successfully used to deliver desired sequences to cells and tend to have a high infection efficiency. Suitable vector-NE transporter gene constructs are adapted for administration as pharmaceutical compositions, as described herein below.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments can also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication can be provided either by construction of the vector to include an exogenous origin, such as can be derived from SV40 or other viral (e.g., Polyoma, Adeno, VSV, BPV) source, or can be provided by the host cell chromosomal replication mechanism. If the vector is integrated into the host cell chromosome, the latter is often sufficient.

Where a NE transporter gene itself is employed it will be most convenient to simply use a wild type NE transporter gene directly. Preferably, the NE transporter gene comprises the alanine encoding allele such that amino acid 457 of the encoded polypeptide comprises alanine. Additionally, it is provided that certain regions of a NE transporter gene can be employed exclusively without employing an entire wild type NE transporter gene or an entire allelic variant thereof. It is proposed that it will ultimately be preferable to employ the smallest region needed to modulate NE transport so that one is not introducing unnecessary DNA into cells which receive a NE transporter gene construct. Techniques well known to those of skill in the art, such as the use of restriction enzymes, will allow for the generation of small regions of an exemplary NE transporter gene. The ability of these regions to modulate NE transport can easily be determined by the assays reported in the Examples. In general, techniques for assessing the modulation of NE transport are known in the art.

C.1. Transgenic Animals

It is also within the scope of the present invention to prepare a transgenic non-human animal which expresses a NE transporter gene of the present invention or in which expression of a NE transporter gene is "knocked-out". The present invention provides transgenic non-human animals that express either the A457 form of NE transporter or the P457 form of NE transporter. A preferred transgenic animal is a mouse.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), the entire contents of each of which are herein incorporated by reference.

With respect to an exemplary method for the preparation of a transgenic mouse, cloned recombinant or synthetic DNA sequences or DNA segments encoding a NE transporter gene product are injected into fertilized mouse eggs. The injected eggs are implanted in pseudo pregnant females and are grown to term to provide transgenic mice whose cells express a NE transporter gene product. Preferably, the injected sequences are constructed having promoter sequences connected so as to express the desired protein in cardiac cells of the transgenic mouse.

C.2. Gene Therapy

NE transporter genes can be used for gene therapy in accordance with the present invention. Exemplary gene therapy methods, including liposomal transfection of nucleic acids into host cells, are described in U.S. Pat. Nos. 5,279,833; 5,286,634; 5,399,346; 5,646,008; 5,651,964; 5,641,484; and 5,643,567, the contents of each of which are herein incorporated by reference.

Briefly, NE transporter gene therapy directed toward modulation of NE transport in a target cell is described. Target cells include but are not limited cardiac cells. In one embodiment, a therapeutic method of the present invention provides a method for modulating of NE transport in a cell comprising the steps of: (a) delivering to the cell an effective amount of a DNA molecule comprising a polynucleotide that encodes a NE transporter polypeptide that modulates NE transport; and (b) maintaining the cell under conditions sufficient for expression of said polypeptide.

Delivery is preferably accomplished by injecting the DNA molecule into the cell. Where the cell is in a subject delivering is preferably administering the DNA molecule into the circulatory system of the subject. In a preferred embodiment, administering comprises the steps of: (a) providing a vehicle that contains the DNA molecule; and (b) administering the vehicle to the subject.

A vehicle is preferably a cell transformed or transfected with the DNA molecule or a transfected cell derived from such a transformed or transfected cell. An exemplary and preferred transformed or transfected cell is a hepatic cell. Means for transforming or transfecting a cell with a DNA molecule of the present invention are set forth above.

Alternatively, the vehicle is a virus or an antibody that specifically infects or immunoreacts with an antigen of the tumor. Retroviruses used to deliver the constructs to the host target tissues generally are viruses in which the 3'-LTR (linear transfer region) has been inactivated. That is, these are enhancerless 3'-LTR's, often referred to as SIN (self-inactivating viruses) because after productive infection into the host cell, the 3'-LTR is transferred to the 5'-end and both viral LTR's are inactive with respect to transcriptional activity. A use of these viruses well known to those skilled in the art is to clone genes for which the regulatory elements of the cloned gene are inserted in the space between the two LTR's. An advantage of a viral infection system is that it allows for a very high level of infection into the appropriate recipient cell.

Antibodies have been used to target and deliver DNA molecules. An N-terminal modified poly-L-lysine (NPLL)-antibody conjugate readily forms a complex with plasmid DNA. A complex of monoclonal antibodies against a cell surface thrombomodulin conjugated with NPLL was used to target a foreign plasmid DNA to an antigen-expressing mouse lung endothelial cell line and mouse lung. Those targeted endothelial cells expressed the product encoded by that foreign DNA.

It is also envisioned that this embodiment of the present invention can be practiced using alternative viral or phage vectors, including retroviral vectors and vaccinia viruses whose genome has been manipulated in alternative ways so as to render the virus non-pathogenic. Methods for creating such a viral mutation are set forth in detail in U.S. Pat. No. 4,769,331, incorporated herein by reference.

By way of specific example, a human NE transporter-encoding polynucleotide or a NE transporter-encoding polynucleotide homolog from another warm-blooded vertebrate is introduced into isolated cardiac cells or other relevant cells. The re-injection of the transgene-carrying cells into the heart or other relevant tissues provides a treatment for susceptibility to impaired NET function, orthostatic intolerance, or other relevant diseases in human and animals.

D. Pharmaceutical Compositions

In a preferred embodiment, the present invention provides pharmaceutical compositions comprising a polypeptide or polynucleotide of the present invention and a physiologically acceptable carrier. More preferably, a pharmaceutical composition comprises a polynucleotide that encodes a biologically active NE transporter polypeptide.

A composition of the present invention is typically administered orally or parenterally in dosage unit formulations containing standard, well-known nontoxic physiologically acceptable carriers, adjuvants, and vehicles as desired. The term "parenteral" as used herein includes intravenous, intramuscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono-or di-glycerides. In addition, fatty acids such as oleic acid find use in the preparation of injectables.

Preferred carriers include neutral saline solutions buffered with phosphate, lactate, Tris, and the like. Of course, in the case of a pharmaceutical composition provided in use in gene therapy, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A transfected cell can also serve as a carrier. By way of example, a liver cell can be removed from an organism, transfected with a polynucleotide of the present invention using methods set forth above and then the transfected cell returned to the organism (e.g. injected intra-vascularly).

D.1. Dosages

As used herein, an "effective" dose refers to one that is administered in doses tailored to each individual patient manifesting symptoms of NE transport deficiency sufficient to cause an improvement therein. After review of the disclosure herein of the present invention, one of ordinary skill in the art can tailor the dosages to an individual patient, taking into account the particular formulation and method of administration to be used with the composition as well as patient height, weight, severity of symptoms, and stage of the disorder to be treated.

An effective dose and a therapeutically effective dose are generally synonymous. However, compounds can be administered to patients having reduced symptoms or even administered to patients as a preventative measure. Hence, the composition can be effective in therapeutic treatment even in the absence of symptoms of the disorder.

A unit dose can be administered, for example, 1 to 4 times per day. Most preferably, the unit dose is administered twice a day (BID). The dose depends on the route of administration and the formulation of a composition containing the compound or compounds. Further, it will be appreciated by one of ordinary skill in the art after receiving the disclosure of the present invention that it can be necessary to make routine adjustments or variations to the dosage depending on the combination of agents employed, on the age and weight of the patient, and on the severity of the condition to be treated.

Such adjustments or variations, as well as evaluation of when and how to make such adjustments or variations, are well known to those of ordinary skill in the art of medicine. Evaluation parameters and techniques can vary with the patient and the severity of the disease. Particularly useful evaluative techniques for NE transport include NE clearance, tyramine administration and other standard tests such as are disclosed in the Examples.

D.2. Gene Therapy Vector Construct Dosing.

Maximally tolerated dose (MTD) of vector construct when administered directly into the affected tissue is determined. Primary endpoints are: 1) the rate of transduction in abnormal and/or normal cells, 2) the presence and stability of this vector in the systemic circulation and in affected cells, and 3) the nature of the systemic (fever, myalgias) and local (infections, pain) toxicities induced by the vector. A secondary endpoint is the clinical efficacy of the vector construct.

For example, a 4 ml serum-free volume of viral (e.g. adenoviral, retroviral, etc.) vector construct (containing up to $5 \times 10^7$ viral particles in AIM V media) is administered daily per session. During each session, 1 ml of medium containing the appropriate titer of vector construct is injected into 4 regions of the affected tissue for a total of 4 ml per session in a clinical examination room. This is repeated daily for 4 days (4 sessions). This 16 ml total inoculum volume over 4 days is proportionally well below the one safely tolerated by nude mice (0.5 ml/20 g body weight).

Patient evaluation includes history and physical examination prior to initiation of therapy and daily during the 4 day period of vector construct injection. Toxicity grading is done using the ECOG Common Toxicity Criteria. CBC, SMA-20, urinalysis, and conventional studies are performed daily during this period.

D.3. Dose Escalation and MTD.

Patients are treated with $3 \times 10^6$ viral particles×4. Once they have all recovered from all grade 2 or less toxicities (except alopecia), and as long as grade 3–4 toxicity is not encountered, a subsequent dose level is initiated in patients. As one grade 3 or 4 toxicity occurs at a given dose level, a minimum of 6 patients are enrolled at that level. As only 1 of 6 patients has grade 3 or 4 toxicity, dose escalation continues. The MTD of vector construct is defined as the dose where 2 of 6 patients experience grade 3 or 4 toxicity. If 2 of 3, or if 3 of 6 patients experience grade 3 or 4 toxicity, the MTD is defined as the immediately lower dose level.

The following escalation schema is followed: 1) level 1, $3 \times 10^6$ viral particles; 2) level 2, $1 \times 10^7$; 3) level 3, $3 \times 10^7$; 4) level 4, $5 \times 10^7$. Patients with measurable disease are evaluated for a clinical response to vector construct. Histology and local symptoms are followed. NE clearance, tyramine administration and other standard tests such as are disclosed in the Examples are employed.

E. Generation of Antibodies

In still another embodiment, the present invention provides an antibody immunoreactive with a polypeptide or polynucleotide of the present invention. Preferably, an antibody of the invention is a monoclonal antibody. Techniques for preparing and characterizing antibodies are well known in the art (See e.g. *Antibodies: A Laboratory Manual*, E. Howell and D. Lane, Cold Spring Harbor Laboratory, 1988). More preferred antibodies distinguish between the different forms of NE transporter polypeptides (e.g. SEQ ID NOs:2 and 4) that comprise the NE transporter polymorphism.

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide can vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Techniques and reagents for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies, inter alia, upon the nature of the immunogen as well as the animal used for immunization. A variety of routes can be used to administer the immunogen, e.g. subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention provides a method of producing an antibody immunoreactive with a NE transporter polypeptide, the method comprising the steps of (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. Preferably, the NE transporter polypeptide is capable of mediating NE transport, cross-reacting with anti-NE transporter antibody, or other biological activity in accordance with the present invention. Even more preferably, the present invention provides antibodies prepared according to the method described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 µg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

F. Detection Methods

Alternatively, the present invention provides a method of detecting a polypeptide of the present invention, wherein the method comprises immunoreacting the polypeptides with antibodies prepared according to the methods described above to form antibody-polypeptide conjugates, and detecting the conjugates.

In yet another embodiment, the present invention provides a method of detecting messenger RNA transcripts that encode a polypeptide of the present invention, wherein the method comprises hybridizing the messenger RNA transcripts with polynucleotide sequences that en code the polypeptide to form duplexes; and detecting the duplex. Alternatively, the present invention provides a method of detecting DNA molecules that encode a polypeptide of the present invention, wherein the method comprises hybridizing DNA molecules with a polynucleotide that encodes that polypeptide to form duplexes; and detecting the duplexes.

The detection and screening assays disclosed herein can be also used as a part of a diagnostic method. Human NE transporter-encoding polynucleotides as well as their protein products can be readily used in clinical setting to diagnose susceptibility to orthostatic intolerance and to other heritable NE transporter-related diseases in humans.

F.1. Screening Assays for a Polypeptide of the Present Invention

The present invention provides a method of screening a biological sample for the presence of a NE transporter polypeptide. Preferably, the NE transporter polypeptide possesses NE transport activity, cross-reactivity with an anti-NE transporter antibody, or other biological activity in accordance with the present invention. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide. Hepatic tissues comprise particularly contemplated tissues.

Preferably, antibodies which distinguish between the A457 NE transporter polypeptide and the P457 NE transporter polypeptide are provided. Such antibodies can comprise polyclonal antibodies but are preferably monoclonal antibodies prepared as described hereinabove.

In accordance with a screening assay method, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the polypeptide.

Exposure time will vary inter alia with the biological conditions used, the concentration of antibody and polypeptide and the nature of the sample (e.g., fluid or tissue sample). Techniques for determining exposure time are well known to one of ordinary skill in the art. Typically, where the sample is fluid and the concentration of polypeptide in that sample is about $10^{-10}$M, exposure time is from about 10 minutes to about 200 minutes.

The presence of polypeptide in the sample is detected by detecting the formation and presence of antibody-polypeptide conjugates. Techniques for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}$P, $^{125}$I, $^{14}$C), a second antibody or an enzyme such as horse radish peroxidase. Techniques for affixing indicators to antibodies are well known in the art. Commercial kits are available.

F.2. Screening Assay for Anti-Polypeptide Antibody

In another aspect, the present invention provides a method of screening a biological sample for the presence of antibodies immunoreactive with a NE transporter polypeptide. Optionally, the NE transporter polypeptide has NE transport activity, cross-reactivity with an anti-NE transporter antibody, or other biological activity in accordance with the present invention.

In accordance with such a method, a biological sample is exposed to a NE transporter polypeptide under biological conditions and for a period of time sufficient for antibody-polypeptide conjugate formation and the formed conjugates are detected. Autoimmune antibodies associated with acquired impaired NET function are particularly contemplated for detection.

Thus, binding substances comprising a NE transporter polypeptide as described herein have selective binding activity with an antibody epitope (antigen recognition specificity). This binding specificity can be employed for detecting and/or purifying the antibody or fragment thereof. The term "fragment" thus refers any fragment of the antibody, such as Fab and F(ab')$_2$ fragments.

A NE transporter polypeptide is prepared as described herein above. The polypeptide is then conjugated to, or labeled with, a material that will enable visualization of the presence of the NE transporter polypeptide.

The NE transporter polypeptide can thus be used in a variety of applications to detect antibodies or antibody fragments. For example, fluoresceinated, alkaline phosphatase labeled, peroxidase labeled, or biotinylated NE transporter polypeptides are used in indirect cytochemical assays to detect antibody binding to cells and tissues in histological or flow cytometric assays. Such detection can be used in a variety of research or clinical contexts.

Similarly, immobilized NE transporter polypeptides can be used to precipitate immune complexes in radioimmune and other quantitative immune or antigen capture assays. Such immunoprecipitation assays where immune complexes of radiolabeled antigens are captured on immobilized NE transporter polypeptides of the present invention have wide application in the art.

By way of elaboration, the NE transporter polypeptides are used to detect the presence of antibodies and fragments thereof, in solutions, or on surfaces exposed to antibodies, or fragments thereof, by a variety of techniques. Techniques which are used include: enzyme-linked immunosorbent assay (ELISA), radioimmunoassay (RIA), immunoblot analysis, immunofluorescent assay (IFA), immunohistochemistry, immunoelectron microscopy (IEM), and immunoilluminescence. Each technique utilizes conjugates including NE transporter polypeptides to visualize the binding of the conjugate to antibody molecules or fragments thereof.

Commonly used conjugates include, but are not limited to, enzymes such as biotin, horseradish peroxidase, alkaline phosphatase (O'Sullivan et al. (1978) *FEBS Letters* 95:311), acid phosphatase, beta-galactosidase (Ishikawa et al. (1978) *Scand. J. Immunol.* 8:43) and luciferase; radioisotopes such as $^{125}I$, $^{35}S$, $^{14}C$, and $^3H$; fluorescent dyes such as fluorescein, rhodamine, dichlorotriazinylaminofluorescein (DTAF; Blakeslee et al., *J. Immunol Meth.* 13:320 (1977)), ferritin (Carlsson et al. (1978) *Biochem. J.* 173:723), fluoroscene isothiocyanste (FITC; McKinney et al. (1966) *Anal. Biochem.* 14:421), sulforhodamine 101 acid chloride (Texas Red) and tetra-methyrhodamine isothiocyanate (TRITC; Amante et al., *J. Immunol. Meth.*, 1:289 (1972)); colloidal gold particles (Horisberger et al., *Histochem.* 82:219 (1985)); and the like. Effective procedures for such conjugations are generally conventional, as described by Harlow et al., 1988, *Antibodies: a laboratory manual*, Cold Spring Harbor Laboratory, Cold Spring Harbor, N.Y.

The protein conjugate is stored in appropriate buffers until needed. Colloidal gold conjugates can be maintained in Tris-based stabilizing buffer, such as those described in Robinson et al., (1984) *Infect. Immun.* 46:361–366. For other conjugates, the buffer would typically be phosphate-buffered saline, pH 7.2 (PBS). However, physiological buffers such as Tris- or borate-buffered saline (TBS or BBS) in pH ranging from 6.5 to 8.0, or non-saline buffers such as acetates, bicarbonates, or citrates within this pH range can be utilized.

When needed to detect the presence of antibodies or fragments thereof in a preparation, the NE transporter polypeptide conjugate can be first diluted in an appropriate buffer. The extent of dilution varies according to the conjugate and sensitivity required, and is normally determined empirically for a given conjugate preparation and detection method. Dilutions typically range from 1:10 to 1:10,000. After dilution the conjugate is incubated with a sample suspected of containing antibodies or fragments thereof. The incubation should proceed for about 15–60 minutes at room temperature, or about 4–16 hours at about 4° C., during which time from one to ten (optimally) NE transporter polypeptide molecules will bind to any antibodies or fragments thereof present. Following incubation, the sample is washed twice for about 5-10 minutes each with dilution buffer or with buffer which is compatible with the visualization conditions (if different). The presence of bound NE transporter polypeptide can then be detected or visualized by chromogenic assay, radioactivity, illuminescence, fluorescence, flow cytometry or electron density, as appropriate for the conjugate.

Thus, a method for detecting an antibody or fragment thereof, in a sample suspected of an antibody or fragment thereof, is provided in accordance with the present invention. The method comprises: (a) contacting the sample with a binding substance comprising a NE transporter polypeptide under conditions favorable to binding an antibody or fragment thereof, to the binding substance to form a complex therebetween; and (b) detecting the complex by means of a label conjugated to the binding substance or by means of a labeled reagent that specifically binds to the complex subsequent to its formation.

In the detection method of the present invention, the binding substance can be immobilized on a solid substrate. In such case, the detecting step (b) comprises: (i) contacting the complex with a reagent conjugated with a detectable label wherein the reagent specifically binds to the antibody or fragment thereof, and (ii) detecting the detectable label.

In the detection method of the present invention, the binding substance can be conjugated with a detectable label. In such case, the detecting step (b) comprises: (i) separating the complex from unbound labeled binding substance; and (ii) detecting the detectable label which is present in the complex or which is unbound.

The detection method of the present invention can further comprise: (i) contacting the complex with a reagent immobilized on a solid substrate to form immobilized complex thereon wherein the reagent binds the antibody or fragment, present in the complexes; and (ii) separating the immobilized complex from the remaining mixture.

F.3. Screening Assay for Polynucleotide That Encodes a NE Transporter Polypeptide of the Present Invention A nucleic acid molecule and, particularly a probe molecule, can be used for hybridizing as an oligonucleotide probe to a nucleic acid source suspected of encoding a NE transporter polypeptide of the present invention. Optimally, the NE transporter polypeptide has NE transport activity, cross-reactivity with an anti-NE transporter antibody, or other biological activity in accordance with the present invention. The probing is usually accomplished by hybridizing the oligonucleotide to a DNA source suspected of possessing a NE transporter gene. In some cases, the probes constitute only a single probe, and in others, the probes constitute a collection of probes based on a certain amino acid sequence or sequences of the polypeptide and account in their diversity for the redundancy inherent in the genetic code.

A suitable source of DNA for probing in this manner is capable of expressing a polypeptide of the present invention and can be a genomic library of a cell line of interest. Alternatively, a source of DNA can include total DNA from the cell line of interest. Once the hybridization method of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells, such as a NE transporter polymorphism described herein; (2) tools for detecting and isolating other members of the polypeptide family and related polypeptides from a DNA library potentially containing such sequences; (3) primers for hybridizing to related sequences for the purpose of amplifying those sequences; (4) primers for altering native NE transporter DNA sequences; as well as other techniques which rely on the similarity of the DNA sequences to those of the DNA segments herein disclosed.

As set forth above, in certain aspects, DNA sequence information provided by the invention allows for the preparation of relatively short DNA (or RNA) sequences (e.g., probes) that specifically hybridize to encoding sequences of a selected NE transporter gene. In these aspects, nucleic acid probes of an appropriate length are prepared based on a consideration of the encoding sequence for a polypeptide of this invention. The ability of such nucleic acid probes to specifically hybridize to other encoding sequences lend them particular utility in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of a nucleic acid sequence of the present invention, such as a sequence shown in any of SEQ ID NOs:1, 3, 11 and 13. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical means, by application of nucleic acid reproduction technology, such as the PCR technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M salt at temperatures of about 50° C. to about 70° C. including particularly temperatures of about 55° C., about 60° C. and about 65° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15M–0.9M salt, at temperatures ranging from about 20° C. to about 55° C., including particularly temperatures of about 25° C., about 37° C., about 45° C., and about 50° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, via the label.

F.4. Assay Kits

In another aspect, the present invention provides diagnostic assay kits for detecting the presence of a polypeptide of the present invention in biological samples, where the kits comprise a first container containing a first antibody capable of immunoreacting with the polypeptide, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also provides a diagnostic kit for screening agents. Such a kit can contain a polypeptide of the present invention. The kit can contain reagents for detecting an interaction between an agent and a receptor of the present invention. The provided reagent can be radiolabeled. The kit can contain a known radiolabelled agent capable of binding or interacting with a receptor of the present invention.

In an alternative aspect, the present invention provides diagnostic assay kits for detecting the presence, in biological samples, of a polynucleotide that encodes a polypeptide of the present invention, the kits comprising a first container that contains a second polynucleotide identical or complementary to a segment of at least 10 contiguous nucleotide bases of, as a preferred example, in any of SEQ ID NOs:1, 3, 11 and 13.

In another embodiment, the present invention provides diagnostic assay kits for detecting the presence, in a biological sample, of antibodies immunoreactive with a polypeptide of the present invention, the kits comprising a first container containing a NE transporter polypeptide, that immunoreacts with the antibodies, with the polypeptide present in an amount sufficient to perform at least one assay.

Autoimmune antibodies associated with acquired impaired NET function are particularly contemplated for detection. Preferably, the NE transporter polypeptide has NE transport activity, cross-reactivity on an anti-NE transporter antibody, or other biological activity in accordance with the present invention. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

G. Other Diagnostic Methods

The present invention also provides the detection and diagnoses of impaired NE transport and disorders related thereto based on the use of standard tests associated with evaluating NE transport function, such as the NE clearance and tyramine tests described in the Examples. Such test results are prepared, and the results are compared to results observed in patients having the NET mutation disclosed herein. Test results that indicate a correlation with the results observed in a patient having the polymorphism disclosed herein indicates the presence of a deficiency in NE transport in a patient so screened.

For example, in the NE clearance evaluations described in the Examples, NE transport deficient patients, (i.e. those having the NET polymorphism disclosed herein) were observed to have NE clearance rates ranging from about 1–2 liters per minute. In contrast, NE clearance rates are 2–3 liters per minute in normal patients.

Additionally, in the tyramine administration test disclosed in the Examples, elevated plasma NE levels after administration of the unit dose of tyramine were observed to range from about 1 to about 20 pg/ml and more particularly from about 5 to about 50 pg/ml in patients having the NE transporter polymorphism disclosed herein. In contrast, plasma NE levels after administration of a unit dose of tyramine in a normal patient ranges from about 40 to about 70 pg/ml, and usually ranges from about 50 to about 60 pg/mL.

Urinary NE levels range from about 100 to about 500 μg/24 hrs and usually from about 200 to about 400 in the patients observed to have the NET polymorphism. In contrast, in normal patients, urinary NE levels range from about 0 to about 90 μg/24 hrs. Thus, these data can be used in accordance with the present invention to detect impaired NE transport and disorders related thereto.

In accordance with the present invention, the ratio of DHPG to NE in blood is also used to detect impaired NE transport and disorders related thereto. DHPG is a metabolite of NE, resulting from the enzymatic action of monoamine oxidase. Since the monoamine oxidase is predominantly in the neuron itself, NE pumped back into the neuron by the NET is exposed to the enzyme and can be broken down into DHPG, which can then leak out into the plasma. If the NET is not functioning appropriately or if there is a deficiency of NET, not as much norepinephrine is pumped up into the neuron and subsequently metabolized to DHPG. Thus, the ratio of DHPG to NE in blood is less in patients with NET deficiency. This difference can appear during upright posture or with exercise. The ratio of DHPG to NE in blood is determined, and the results are compared to results observed in patients having the NET mutation disclosed herein. Test results that indicate a correlation with the results observed in a patient having the polymorphism disclosed herein indicates the presence of a deficiency in NE transport in a patient so screened.

In accordance with the present invention, the ratio of DHPG to normetanephrine (NMN) is also used to detect impaired NE transport and disorders related thereto. When NE is not pumped into the neuron by the NE transporter, NE is exposed to extraneuronal tissue which contains a different enzyme called catechol-O-methyltransferase (COMT), which catalyzes the metabolism of NE to NMN. The metabolism of NE to NMN is enhanced under circumstances where NE transport into the neuron is impaired, and thus, a ratio of DHPG to normetanephrine (NMN) can also be used to detect impaired NE transport and disorders related thereto. The ratio of DHPG to NMN is determined, and the results are compared to results observed in patients having the NET mutation disclosed herein. Test results that indicate a correlation with the results observed in a patient having the polymorphism disclosed herein indicates the presence of a deficiency in NE transport in a patient so screened.

In another aspect, the method can be used to detect susceptibility to a NET mediated disorder in a patient. The detection of secondary test results indicative of impaired NET function can thus be used to detect susceptibility to mental illness, hypertension, heart disease and psycho stimulant abuse (e.g. cocaine or amphetamine abuse). Thus, the methods of the present invention are believed to meet a long felt need in the art for further characterization of NE transport impairments and predictive ability to detect susceptibility to disorders related thereto.

Stated differently, the identification of the NET transporter mutation as set forth herein represents the first establishment of a link between genetic causes of NET deficiencies and more indirect measures of NET deficiencies, such as the tyramine and NE clearance tests disclosed in the Examples presented below. This information is thus useful in facilitating diagnoses of approximately half a million patients in the United States alone who are suffering from disorders associated with NET deficiencies.

EXAMPLES

The following Examples have been included to illustrate preferred modes of the invention. Certain aspects of the following Examples are described in terms of techniques or procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only in that numerous changes, modification, and alterations can be employed without departing from the spirit and scope of the invention.

MATERIALS AND METHODS USED IN EXAMPLES

Clinical Characteristics

The proband was a 33-year old female with a 20 year history of exertional and orthostatic provocation of tachycardia, dyspnea, concentration difficulty, and syncope. She had volatile blood pressure during or following anaesthesia with each of her three Caesarean sections with blood pressures as high as 210/180 mm Hg. Standard treatment for syncope (β-blockers, compression stockings, fludrocortisone) had been unsatisfactory. Implantation of a dual chamber pacemaker seemed to decrease the frequency of syncope, but symptoms of orthostatic intolerance persisted. An echocardiogram revealed mild mitral regurgitation and possible mitral valve prolapse. The probands identical twin also had a history of mitral valve prolapse and syncope as well as multiple symptoms worsened by stress and upright posture.

Experimental Design

The proband and her twin were admitted to the General Clinical Research Center at Vanderbilt University Medical Center, Nashville, Tenn. They were placed on a caffeine-free, low monoamine diet containing 150 mEq Na$^+$ and 70 mEq K$^+$ per day for 3 days. All medications had been discontinued at least two weeks prior to admission. After fasting supine overnight, blood pressure, heart rate, and plasma catecholamines were measured supine and after standing. At least two hours after breakfast standard autonomic function testing was performed as described by Mosqueda-Gracia, *Disorders of the Autonomic Nervous System* (1995). Urine was collected over a 24 hour period for catecholamines and catecholamine metabolites.

In the proband, and a group of normal volunteers, systemic norepinephrine spillover and clearance and plasma norepinephrine concentrations were determined before and at the maximal blood pressure increase after an intravenous injection of 3 mg tyramine. Supine and upright blood pressure and heart rate, plasma catecholamines, norepinephrine spillover and clearance, and tyramine-mediated plasma catecholamine responses were compared to responses among subjects in a group of 10 normal volunteers (8 females, 2 males, 33±2 years).

In seven additional siblings and the proband's mother, blood pressure and heart rate were determined after twenty minutes supine and five minutes standing. Blood was obtained for determination of plasma catecholamines after twenty minutes supine and then after thirty minutes upright. In addition, blood was obtained from the proband, all nine of her siblings and her mother for DNA analysis. Plasma catecholamine or orthostatic vitals signs from one sister of the proband were not obtained. Her father is deceased. All subjects gave informed consent prior to study.

Plasma was analyzed for catecholamines by a modification of a high pressure liquid chromatographic method described by Goldstein et al., *J Clin Invest* (1988). Urine samples for catecholamines were assayed using analogous methods. See Goldstein et al., *J Clin Invest* (1988), Shoup et al., *Clin Chem* (1977). Tyramine responsiveness was determined by assaying blood pressure and heart rate after administration of 3 mg intravenous tyramine.

Systemic Norepinephrine Spillover and Clearance

The proband and normal controls were studied after overnight rest. Catheters were placed in a brachial artery, the ipsilateral femoral vein, and bilateral antecubital veins. Blood pressure was monitored intraarterially and heart rate was monitored by continuous ECG. After instrumentation and 30 minutes recovery, tritiated norepinephrine (3H-NE) was infused intraveneously at 0.9 µCi/mL/min (see Riley et al., *Clin Sci* (1991)) after a loading dose of 25 µCi over 2 min. See Esler et al., *Physiol Rev* (1990). After allowing 30 to 40 minutes to reach steady state, blood for baseline norepinephrine concentration was obtained from the artery. Norepinephrine spillover and clearance were determined before and during baroreflex-mediated sympathetic activation with infusion of nitroprusside sufficient to decrease systolic blood pressure by 20 mmHg. $^3$H-NE concentration in plasma samples was determined as described by Shannon et al., *Circulation* (1999).

Detection of Mutations

Genomic DNA was isolated from venous blood using the PureGene DNA Extraction Kit (Gentra Systems, Minneapolis, Minn.). The exons of the human NET gene (SLC6A2, McKusick # 163970) were amplified using the polymerase chain reaction (PCR) with sense and antisense primers set forth in Table 2 as follows:

TABLE 2

Primer Sets for Amplification of the Exons of the Human NET Gene

| | |
|---|---|
| Exon 1: | |
| RB639 (5'-aggaccggtaaagttcctctcg-3') | (SEQ ID NO:16) |
| RB640 (5'-tccgtgtgtattccagctcctg-3') | (SEQ ID NO:17) |
| | |
| Exon 2: | |
| RB641 (5'-gattgctgcgcgtcgcctttg-3') | (SEQ ID NO:18) |
| RB642 (5'-ccttagatctcaccactggag-3') | (SEQ ID NO:19) |
| | |
| Exon 3: | |
| RB643 (5'-catgcgacaggtcactggtg-3') | (SEQ ID NO:20) |
| RB644 (5'-tagtgtttggctcaggtcatac-3') | (SEQ ID NO:21) |
| | |
| Exon 4: | |
| RB645 (5'-agagtggccaggtcctgtct-3') | (SEQ ID NO:22) |
| RB646 (5'-cttgcacttccagctccatctt-3') | (SEQ ID NO:23) |

TABLE 2-continued

Primer Sets for Amplification of the Exons of the Human NET Gene

```
Exon 5:
RB647 (5'-tggcttcagggccttgcctagag-3')        (SEQ ID NO:24)
RB648 (5'-acaagcctggcccaaggcttggt-3')        (SEQ ID NO:25)

Exon 6:
RB649 (5'-ctgcccatctctggttcagaccat-3')       (SEQ ID NO:26)
RB650 (5'-ggagagttggcttccagaccaga-3')        (SEQ ID NO:27)

Exon 7:
RB651 (5'-gtatccatgtggcagcaggagc-3')         (SEQ ID NO:28)
RB652 (5'-cacggaagagccatgcagccaa-3')         (SEQ ID NO:29)

Exon 8:
RB653 (5'-ctatcatgtgcagctcagaccaatgg-3')     (SEQ ID NO:30)
RB654 (5'-gtctgcaatttaaatagggccttctgg-3')    (SEQ ID NO:31)

Exon 9:
RB655 (5'-caaggcagcctacatgagtcctgg-3')       (SEQ ID NO:32)
RB667 (5'-taacagggctgaatggaatcctcag-3')      (SEQ ID NO:33)

Exons 9 and 10:
RB655 (5'-caaggcagcctacatgagtcctgg-3')       (SEQ ID NO:32)
RB656 (5'-ggtgcaggattctaggaggactgg-3')       (SEQ ID NO:34)

Exons 11 and 12:
RB657 (5'-catcttgcctcactgccctgctct-3')       (SEQ ID NO:35)
RB658 (5'-catcttgcctcactgccctgctct-3')       (SEQ ID NO:36)

Exons 13 and 14:
RB659 (5'-gctgcaggatcaaatagcaggtgg-3')       (SEQ ID NO:37)
RB660 (5'-tgctcctctcctctgagctaacag-3')       (SEQ ID NO:38)

Exon 15:
RB746 (5'-ggaggtgcttggagatcatttgg-3')        (SEQ ID NO:39)
RB747 (5'-gcttcagtctcacattagcgagg-3')        (SEQ ID NO:40)
```

Amplified products (60 ng) were directly sequenced using PCR primers with AmpliTaq®-FS fluorescent dideoxy chain terminators (Perkin Elmer, Wellesley, Mass.) using 25 cycles of 96° C. for 30 sec, 50° C. for 15 sec, and 60° C. for 4 min. After ethanol precipitation, the reactions were analyzed on an ABI 310™ automated DNA sequencer (Vanderbilt University Center for Molecular Neuroscience DNA Sequencing Core, Nashville, Tenn.). Sequences were compared to the hNET genomic sequences reported in GenBank (Accession numbers x91117 to x91127) and the sequences reported by Pörzgen and colleagues (Pörzgen et al., *Biochimica et Biophysica Acta* (1998)), as well as in comparison with DNA from asymptomatic volunteers.

Functional Analysis of Identified Coding Mutation

DNA encoding the hNET A457P mutant was created using QuikChange™ Site-Directed Mutagenesis Kit (Stratagene, La Jolla, Calif.) according to manufacturer's protocol using the oligonucleotides RB675 (5'ccttcagtactttccttctc-ccctgttctgcataaccaag-3') (SEQ ID NO:5) and RB676 (5'ct-tggttatgcagaacagggggagaaggaaagtactgaagg-3') (SEQ ID NO:6). The underlying bases indicate modified bases to introduce the g237c mutation or to introduce a Sca I restriction site that could be used to identify mutated plasmids. Amplified DNA was cloned into a pcDNA3 (Invitrogen, Carlsbad, Calif.) construct containing wild type hNET cDNA that had been previously mutated to introduce a silent mutation (L438L), creating a unique Afi II site to facilitate subcloning of the mutated sequences back into the wild type construct. The subcloned region was sequenced using hNET oligonuceotides RB252 (SEQ ID NO:7) (5'-cattctgggctgt-tgtgt-3') and RB584 (SEQ ID NO:8) (5'-gtggttgtggtcagcat-catc-3'). DNA from multiple isolates of mutant clones were purified (Qiagen Inc., Santa Clarita, Calif.) to test for the impact of the A457P mutation on transporter activity.

hNET, hNET A457P, and pcDNA3 plasmids were transiently tranfected in parallel into Chinese Hamster Ovary (CHO; American Type Culture Collection, Manasas, Va., accession no. CCL-61) cells using lipofectamine (Gibco-BRL, Grand Island, N.Y.) according to manufacturer's protocols. CHO cells were cultured at 37° C. in 5% $CO_2$ in Dulbelco's Minimum Essential Medium with 10% fetal bovine serum (Hyclone, Logan, Utah), 2 mM glutamine (Gibco-BRL, Grand Island, N.Y.), 100 I. U./ml penicillin (Gibco-BRL, Grand Island, N.Y.), and 100 μg/ml streptomycin (Gibco-BRL, Grand Island, N.Y.). Twelve well plates (Falcon™ 3043 plates, Becton Dickinson, N.J.) were seeded with 2.0–2.5×10⁵ cells per well. Approximately 48 hours later, the cells were transfected with the appropriate DNA constructs (A457P mutant, wild type hNET, or pcDNA3) in a 1:2 DNA:lipofectamine ratio. Cells were supplemented with fresh medium at 8 hours and then refed with fresh medium after a subsequent 14 hours. The cells were assayed for ³H-NE transport activity (20 nM) 72 hours after initial transfection as described by Apparsundaram et al., *J Pharm Exp Ther* (1998).

Genotyping of A457P Alleles

Allele specific oligonucleotide hybridization (ASO) was used to genotype individuals for the A457P mutation with RB704 (5'-ccttctcgccctgtt-3') (SEQ ID NO:9) hybridizing to the wild type allele and RB705 (5'-ccttctccccctgtt-3') (SEQ ID NO: 10) hybridizing to the mutant allele. The underlined bases identify the single nucleotide polymorphism. All genomic DNA was coded prior to analysis to preserve anonymity of the sample. Genotypes were assigned without knowledge of the sample's identity and then used to associate genotype with a phenotype.

Statistical Analysis

Results are expressed as mean±SEM. Paired and unpaired two tail t-tests were used for comparisons between groups and within one group before and after the various stimuli. Data were analyzed using GRAPHPAD PRISM™ software. (GraphPAD Software Inc., San Diego, Calif.) A p value less than 0.05 was considered significant.

Example 1

Autonomic Responses

Figure 1A:
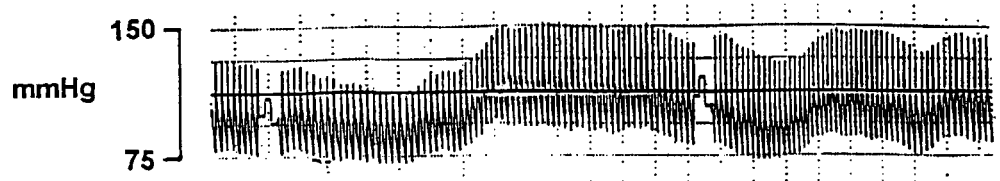
FIGS. 1A–1C depict continuous blood pressure (BP) and heart rate (HR) recordings. Beat-by-beat BP as determined by photoplethysmography and continuous HR recording illustrates spontaneous excursions of up to 50 mmHg and 25 bpm respectively in the proband (FIG. 1A) and her identical twin (FIG. 1B). With tilt (FIG. 1C), BP and HR volatility is intensified.
Figure 1B:
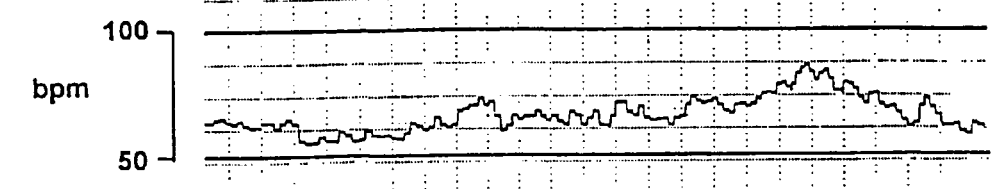
Figure 1C:
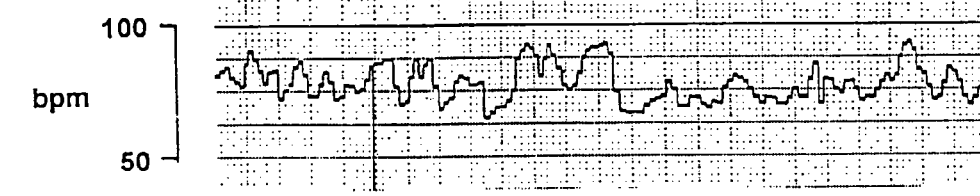

Autonomic reflexes in both the proband and her twin were intact. The proband and twin had volatility of blood pressure and heart rate (FIG. 1). Supine and upright blood pressure, heart rate, and plasma catecholamines of the proband and her twin as compared to control subjects (Shannon et al., *Circulation* (1999)) are depicted in Table 3. The plasma levels of dihydroxyphenylglycol (DHPG, intraneuronal monoamine oxidase (MAO) metabolite of norepinephrine) (Goldstein et al., *J Clin Invest* (1988)) in the proband and her twin were low relative to the plasma level of norepinephrine. In normal controls, the supine DHPG/norepinephrine ratio was approximately 5:1 while in the proband and her twin, the ratio was approximately 2:1. With standing, the ratios in normal controls averaged 3:1 while in the proband and twin, they were 1:1. Urinary norepinephrine was elevated outside the normal range in both the proband and her twin (Table 3).

Example 2

Systemic Norepinephrine Spillover and Clearance

Arterial norepinephrine concentration at rest was slightly elevated in the proband compared to controls (280 pg/ml vs 204±18 pg/ml). This greater concentration was primarily due to decreased NE clearance since, despite a lower NE spillover rate in the proband (436 ng/min in the proband vs 514±98 ng/min in controls, clearance in the proband was less than half of normal controls (1.56 vs 2.42±0.25 L/min). With nitroprusside infusion, NE spillover increased to 1072 ng/min in the proband but only 745±75 ng/min in control subjects. Norepinephrine clearance did not change appreciably after nitroprusside in either the proband (1.76 L/min) or the control group (2.31±0.24 L/min).

Example 3

Response to Tyramine

Tyramine is an indirectly-acting amine that exerts its effect by releasing cytosolic norepinephrine. To cause norepinephrine release, tyramine must first be taken up into the neuron by NET, as described by Blakely et al., *J Exp Biol* (1994), and Demanet, *Cardiology* (1976). Intravenous injection of tyramine 3 mg increased systolic blood pressure 19±2 mmHg and plasma norepinephrine by 56±21 pg/ml in normal controls. In the proband, the same dose increased systolic blood pressure similarly (118 mmHg), but the elevation in plasma norepinephrine was significantly blunted (12 pg/ml).

Example 4

Identification of a Functional Missense Mutation in hNet

The combination of the low plasma DHPG/norepinephrine ratio, decrease of plasma norepinephrine clearance, and blunted response to tyramine suggested a potential defect in NET in the proband. The presence of a similar syndrome in her identical twin suggested a genetic origin.

Direct sequence analysis of the human norepinephrine transporter (hNET) gene (SLC6A2) in the proband revealed no divergence from previously published sequences in exons 1 through 8 and 10 through 15. In addition, all exonic boundaries preserved canonical gt/ag donor/acceptor sequences. However, two novel polymorphisms were identified within exon 9, one silent (c154a) and one missense (g237c) mutation. The proband is heterozygous for both the c154a and g237c polymorphisms (FIG. 2A). The g237c mutation results in a coding alteration of alanine to proline (A457P) within a highly conserved region of transmembrane domain 9 (FIG. 2B and FIG. 2C).

Heterologous expression of hNET in parallel with hNETA457P cDNAs revealed that $^3$H-NE uptake is severely compromised by the A457P mutation. Chinese hamster ovary (CHO) cells transiently transfected with hNET cDNA display a >10 fold elevation in norepinephrine transport activity over vector transfected cells. CHO cells transiently transfected with A457P NET cDNA possessed ≦2% of the uptake activity of the wild type NET transfected cells (FIG. 2D). Multiple clones were tested and all were found to be devoid of transport activity in a different cell host (LLC PK1 cells).

Example 5

Segregation of A457P Mutation with Phenotype

Figure 3A:
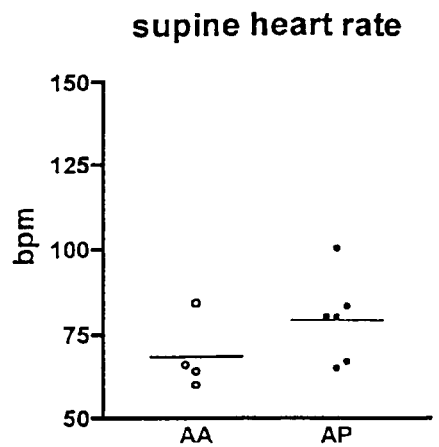
FIGS. 3A–3F depict supine and upright heart rate and plasma catecholamines in the proband's family. Heart rate (HR) and plasma concentrations of norepinephrine (NE) and its intraneuronal metabolite dihydroxyphenylglycol (DHPG) in family members with (AP) and without (AA) the A457P mutation. Supine HR (FIG. 3A) was similar in AA and AP individuals. Upright HR (FIG. 3B) and NE (FIG. 3D) were significantly greater in AP family members than in AA individuals. Supine NE (FIG. 3C) trended toward higher values in AP individuals but did not reach statistical significance. The ratio of DHPG to NE was significantly lower in AP individuals both supine and upright with impairment of NE reuptake. (*$p=0.08$, $p<0.05$, *$p=0.01$). Plasma DHPG/norepinephrine ratio was significantly greater in AA individuals that in AP individuals with both supine and upright postures (FIG. 3E and FIG. 3F).
Figure 3B:
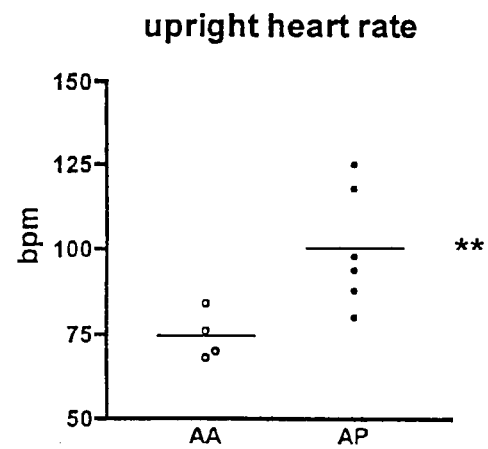
Figure 3C:
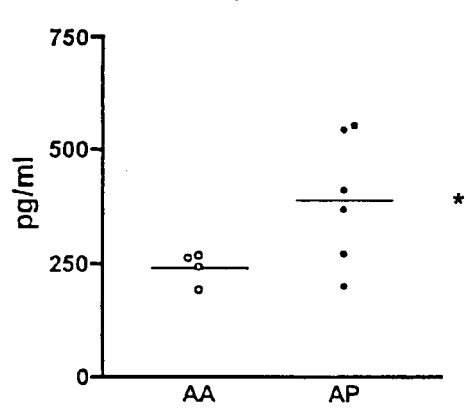
Figure 3D:
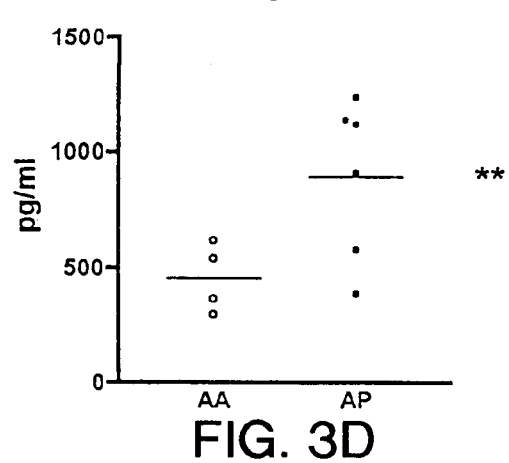
Figure 3E:
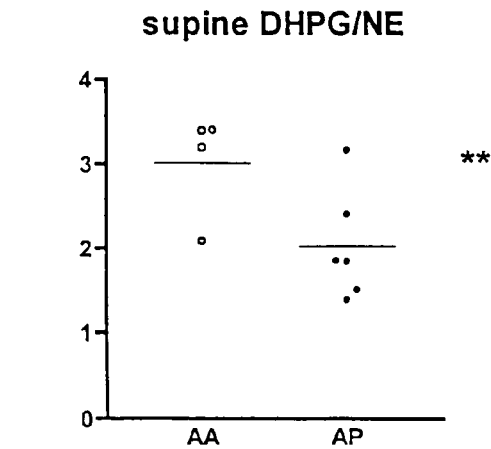
Figure 3F:
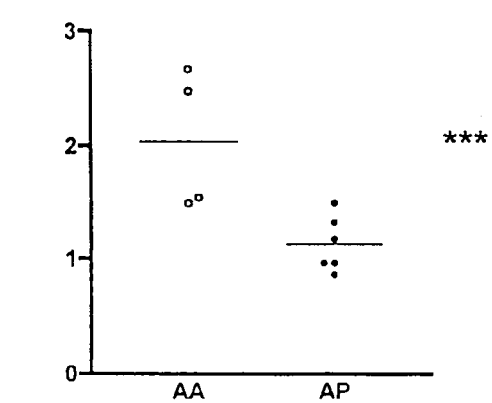

The proband's mother and 4 of her 8 siblings were genotyped by ASO and were found to be heterozygous for the mutant allele (AP), including her twin (FIG. 2E and FIG. 2F). Independently, heart rates and plasma catecholamines were obtained from the family. Supine heart rates displayed a trend toward elevation associated with the AP genotype (p=ns). However, upon standing, the heart rate was significantly greater in family members carrying the A457P mutation (AP) than in family members homozygous for the A457 genotype (AA) (FIG. 3A and FIG. 3B). Similarly, supine plasma norepinephrine tended to be greater in AP that AA family members, whereas upright norepinephrine was significantly greater in AP individuals (FIG. 3C and FIG. 3D). Finally, the plasma DHPG/norepinephrine ratio was significantly greater in AA individuals that in AP individuals with both supine and upright postures (FIG. 3E and FIG. 3F).

Example 6

Mechanism Underlying the Loss of Transport of A457P

As disclosed herein above, the norepinephrine transporter (NET) is responsible for clearance of norepinephrine (NE) from the synapse and is a target for antidepressant drugs and psychostimulants. A human NET (hNET; SLC6A2) coding mutation, A457P, linked to orthostatic Intolerance which results in near complete loss of [$^3$H]NE transport (<2% of wild type (wt)) is also disclosed herein above. This Example pertains to the identification of a mechanism underlying the loss of transport of A457P. Biotinylation of cell surface proteins and Western analysis reveal that the 80–100 kD form of hNET, the major species in the plasma membrane, is decreased in total cell extracts and in plasma membrane from COS-7 cells transfected with A457P compared to wt. Competition of [$^{125}$I]RTI-55 binding to membrane preparations demonstrates alterations in both antagonist and substrate binding to A457P. Cotransfection of A457P with wt hNET reveals a dominant negative interaction of decreased [$^3$H]NE uptake to 59±2.4% of wt alone.

Example 7

Additional hNET Single Nucleotide Polymorphisms

Using techniques described in Example 6 above, applicants have also characterized additional hNET single nucleotide polymorphisms (SNPs) that have been identified, e.g. Stober et al. (1996) *American Journal of Medical Genetics* 67:523–532 and Halushka et al. (1999) *Nature Genetics* 22:239–247. Characterization of these SNPs has led to the observation of both loss of function as well as significant increases in transport in different mutants. By screening susceptible populations for hNET mutations and characterizing mutant proteins, structural components underlying transport function are identified and the role and prevalence of hNET mutations in disease are illuminated.

Discussion of Examples

The NET deficiency in this family represents the first demonstration of a functional mutation in a monoamine transporter in humans. Previously, coding polymorphisms have been found in hNET, but these had no effect on norepinephrine transport activity. See e.g. Stober et al., *Genetics* (1996). In contrast, the A457P mutation renders the transporter nonfunctional and segregates with an alteration in heart rate regulation and norepinephrine metabolism. Bedside physiological, pharmacological, and biochemical tests in the proband indicated a defect in norepinephrine reuptake. Supine resting heart rate was within normal range but about 10 bpm greater than age matched controls, as described by Shannon et al., *Hypertension* (1998), and rose substantially with upright posture. This heart rate change was paralleled by an increase in plasma norepinephrine which rose almost four-fold with upright posture.

The proband's blunted plasma norepinephrine increase with tyramine, and her reduced systemic norepinephrine clearance compared to normal subjects were consistent with impaired norepinephrine reuptake as the primary deficit. The relationship of plasma DHPG and norepinephrine provided further evidence of impaired norepinephrine reuptake. Some NE taken up into the neuron by NET reaches the vesicles where it is stored for re-release, but much is converted to DHPG by MAO, as described in Esler et al., *Physiol Rev* (1990). DGPG can then enter the circulation and serve as a marker of uptake and MAO activity (FIG. 4) (see Goldstein et al., *J Clin Invest* (1988)). The relatively low DHPG compared to norepinephrine in the plasma of the proband and her twin are consistent with impaired NET activity.

These several observations and their consistency between the proband and her twin were highly suggestive of a genetic abnormality in the NET gene, which was previously mapped to chromosome 16q by Bruss, M., et al., *Human Genetics* 91:278–280 (1993). To confirm such a defect, the structure of the proband's NET gene was examined. One missense (g237c) mutation resulting in a coding alteration of alanine to proline (A457P) in a highly conserved transmembrane region was found. Proline disrupts α-helical secondary structures permitted by alanine residues. Therefore, substitution of a proline for alanine in this region is envisioned to disrupt permeation of norepinephrine or its coupled ions Na+ or Cl+. Chimera studies have shown that this transmembrane domain (TMD) 9 falls within a region likely to influence substrate affinity and stereoselectivity of catecholamine transporters (Giros et al., *J Biol Chem* (1994)). Subsequent functional analysis of the proband's NET demonstrated ≦2% activity compared to normal NET.

The A457P mutation is the first genetic defect identified in the syndrome of OI. The pathophysiology of OI has elicited considerable interest in recent years, and a number of potential mechanisms have been suggested. Most invoke a primary or secondary activation of sympathetic outflow to account for the tachycardia and raised norepinephrine with physiological stress. Postulated mechanisms include partial dysautonomia, central hyperadrenergia, abnormal β-adrenoreceptor function and hypovolemia. (Novak et al., *J Aut N Syst* (1996), Rosen et al., *Am J Med* (1982), Fouad et al., *Ann Int Med* (1986), Schodorf et al., *Circulation* (1998), Davies et al., *Am J Med* (1987), Davies et al., *J Clin Endocrinol Metab* (1991)).

NET deficiency can at least partially explain a number of clinical features in patients with OI. Elevated supine heart rate, elevated plasma norepinephrine associated with relatively decreased plasma DHPG, the reduced norepinephrine response to tyramine, reduced systemic norepinephrine clearance, and the disparity of the change in heart rate and plasma norepinephrine as compared to sympathetic nerve activity with upright posture are all contemplated to be attributed to impaired NET activity and/or NET deficiency.

The noradrenergic synaptic clefts in the heart rate are approximately three times narrower than the synapic clefts in the vasculature. See Novi, *Anatomical Record* (1968). Therefore, removal of synaptic norepinephrine in the heart is far more dependent on NET that it is in vascular beds. See Goldstein et al., *Circulation* (1988). Thus, one would expect a disproportionate effect on heart rate and myocardial contractility as compared with blood pressure if NET were dysfunctional. That is precisely what is observed in patients with OI.

The above features primarily represent manifestations of peripheral NET impairment. Central nervous system NET impairment is considerably more complicated. Noradrenergic and adrenergic neurons located at several sites in the central nervous system (e.g. the nucleus tractus solitarii (NTS) and the ventrolateral nuclei in the medulla) are involved in cardiovascular regulation. Increasing concentrations of norepinephrine, epinephrine, and their cogeners in the NTS greatly reduce blood pressure and heart rate in the rat by binding to $α_2$-adrenoreceptors as disclosed by Goldberg et al., *Clinical & Experimental Hypertension—Part A Theory & Practice* (1982), and Tung et al., *J Pharm Exp Ther* (1983).

Agents which stimulate central $α_2$-adrenoreceptors (e.g., cloridine and α-methyldopa) and thus mimic increased central norepinephrine concentrations in sensitive areas are widely used to reduce central sympathetic outflow. The prominent side effects of such agents include fatigue, a common complaint of patients with OI. Acute pharmacological blockade of NET causes a decrease in sympathetic outflow, as described by Esler et al., *American Journal of Physiology* (1991), presumably by increasing norepinephrine concentration in central synapses. Similarly, with NET deficiency, one would expect a decrease in the indices of sympathetic tone. Yet, in the proband and in many patients with OI, central sympathetic tone seems to be increased. Thus, chronic NET impairment, or perhaps compensatory (e.g., baroreflex) responses to it, is contemplated to further complicate phenotype. Peripheral and central impairment of NET could disrupt the fine control of autonomic balance. A limited capacity to clear synaptic norepinephrine might prolong the duration and increase the intensity of adrenoreceptor stimulation resulting from sympathetic nerve electrical activation. The supranormal and prolonged synaptic norepinephrine concentrations interacting with baroreflex-mediated withdrawal of sympathetic nerve traffic could coarsen blood pressure and heart rate patterns. This coarsening of sympathetic modulation could result in a spontaneous cycle of variability in heart rate and, to a lesser extent, vascular tone. Volatility of heart rate in patients with OI has not been reported, see Coghlan et al., *Am J Med* (1979), and was evident in the proband (FIG. 1).

While family members having the A457P mutation had physiological and biochemical similarity to the affected twins and other patients with OI, not all of them manifested the full-blown syndrome. This is contemplated to be attributable to the hemizygous nature of the A457P mutation and preliminary understanding of complex regulatory control over NET mRNA and protein expression. See Apparsundaram et al., *J Pharm Exp Ther* (1998) and Cubells et al., *J Neurochem* (1995).

The disclosure of the present invention, as indicated in the Examples, facilities the discovery of other NET mutations, non-genetic NET defects, and other noradrenergic defects affecting NET function in patients with OI. Among these are autoantibodies to NET or membrane structures essential to NET function. The importance of such a role for autoantibodies is underscored by the preponderance of OI in females in whom autoimmune illnesses are more common, but by the fact that approximately 50% of patients report an antecedent viral illness which could trigger an autoimmune response. See Low et al., *Neurology* (1995). Regardless, the identification of defective norepinephrine transport in patients with OI shifts attention toward a heretofore unexplored mechanism of a very common clinical problem.

TABLE 3

Orthostatic Blood Pressure, Heart Rate, and Plasma Catecholamines Systolic blood pressure (sbp), diastolic blood pressure (dbp) and heart rate (hr) were determined on multiple occasions in the proband and twin and on one occasion in each of eight normal volunteers. Norepinephrine (NE), epinephrine (Epi) and dihydroxyphenylglycol (DPHG) were determined once each in the proband and twin and once in each of the eight normal volunteers. Data are presented as mean ± SEM.

|  |  |  | proband | twin | normals |
|---|---|---|---|---|---|
| Supine and Upright Blood Pressure and Heart Rate | | | | | |
| supine | sbp | (mmHg) | 107 ± 2 | 122 ± 6 | 108 ± 2 |
|  | dpb | (mmHg) | 61 ± 1 | 65 ± 4 | 63 ± 2 |
|  | hr | (bpm) | 75 ± 2 | 72 ± 3 | 65 ± 2 |
| upright | sbp | (mmHg) | 109 ± 3 | 127 ± 5 | 106 ± 3 |
|  | dpb | (mmHg) | 68 ± 2 | 77 ± 3 | 67 ± 3 |
|  | hr | (bpm) | 105 ± 3 | 108 ± 6 | 83 ± 4 |
| Supine and Upright Plasma Catecholamines | | | | | |
| supine | NE | (pg/ml) | 269 | 199 | 200 ± 20 |
|  | Epi | (pg/ml) | 11 | 22 | 25 ± 3 |
|  | DHPG | (pg/ml) | 824 | 480 | 1104 ± 115 |
|  | DHPG/NE |  | 3.06 | 2.41 | 5.52 |
| upright | NE | (pg/ml) | 923 | 911 | 485 ± 50 |
|  | Epi | (pg/ml) | 23 | 116 | 49 ± 4 |
|  | DHPG | (pg/ml) | 968 | 1068 | 1379 ± 133 |
|  | DHPG/NE |  | 1.05 | 1.17 | 2.84 |

TABLE 4

Urinary Catecholmines and Catecholamine Metabolites Norepinephrine (NE), Epinephrine (Epi), norometanephrine (NMN), and metanephrine (MN) in the proband and twin.

|  |  | proband | twin | normal values |
|---|---|---|---|---|
| NE | (μg/24 hrs) | 435 | 125 | 0–90 |
| Epi | (μg/24 hrs) | 22 | 53 | 0–25 |
| NMN | (μg/24 hrs) | 166 | 236 | 50–500 |
| MN | (μg/24 hrs) | 122 | 179 | 50–400 |

REFERENCES

The references listed below as well as all references cited in the specification are incorporated herein by reference to the extent that they supplement, explain, provide a background for or teach methodology, techniques and/or compositions employed herein.

Adelman et al., *DNA* 2:183 (1983).
Adler-Graschinsky et al., *Br J Pharm* 53:43–50 (1975).
Amante et al., *J. Immunol Meth.*, 1:289 (1972)
Apparsundaram et al., *J Pharm Exp Ther* 287:744–751 (1998).
Apparsundaram et al., *J Pharm Exp Ther* 287:733–743 (1998).
Bachmann et al., *New England Journal of Medicine* 304:543 (1981).
Beaucage et al., *Tetrahedron Letters* 22:1859–1862 (1981).
Blakely et al., *J Exp Biol* 196:263–281 (1994).
Blakeslee et al., *J. Immunol. Meth.* 13:320 (1977)
Boudoulas et al., *Circulation* 61:1200–1205 (1980).
Bruss et al., *Human Genetics* 91:278–280 (1993).
Carlsson et al. (1978) *Biochem. J.* 173:723
Coghlan et al., *Am J Med* 67:236–244 (1979).
Crea et al., *Proc. Natl. Acad. Sci. USA* 75:5765 (1978).
Cubells et al., *J Neurochem* 65:502–509 (1995).
Davies et al., *J Clin Endocrinol Metab* 72:867–875 (1991).
Davies et al., *Am J Med* 82:193–201 (1987).
Davis et al., *Circ Res* 61:187–190 (1987).
de Groot, C. J., et al., *Biochemical & Biophysical Research Communications* 124:882–888 (1984).
Demanet, J. C., *Cardiology* 61 suppl 1:213–224 (1976).
DeStefano et al., *American Journal of Human Genetics* 63:1425–1430 (1998).
Eichenlaub et al., *J. Bacteriol.* 138:559–566 (1979).
Esler et al., *Physicol Rev* 70:963–985 (1990).

Esler et al., *American Journal of Physiology* 260: R817–R823 (1991).
Fouad et al., *Ann Int Med* 104:298–303 (1986)
Fraser et al., *Br Med J* 2:27–32 (1981).
Furlan et al., *Circulation* 98:2154–2159 (1998).
Gaffney et al., *Chest* 83:436–438 (1983).
Giros et al., *J Biol Chem* 269:15985–15988 (1994).
Goldberg et al., *Clinical & Experimental Hypertension—Part A, Theory & Practice* 4:595–604 (1982).
Goldstein et al., *Circulation* 78:41–48 (1988).
Goldstein et al., *J Clin Invest* 81:213–220 (1988).
Gribskov et al., *Nucl. Acids. Res.* 14:6745 (1986).
Halushka et al. (1999) *Nature Genetics* 22:239–247.
Harlow et al., 1988, *Antibodies: a Laboratory Manual*, Cold Spring Harbor Laboratory, Cold Spring Harbor, N.Y.
Horisberger et al., *Histochem.* 82:219 (1985).
Howell et al., *Antibodies A Laboratory Manual* Cold Spring Harbor Laboratory, (1988).
Ishikawa et al. (1978) *Scand. J. Immunol.* 8:43
Jacob et al., *Circulation* 96:575–580 (1997).
Jacob et al., *Am J Med* 103:128–133 (1997).
Jacob et al., *Circulation* 99:1706–1712 (1999).
Jordan et al., *Chin J. Physiol* 40:1–8 (1997).
Jordan et al., *Am J. Med. Sci.* (1999).
Kyte & Doolittle, *J. Mol. Biol.* 157:105–132 (1982).
Low et al., *Neurology* 45:S19–S25 (1995).
Maniatis et. al., *Molecular Cloning: A Laboratory Manual*, Cold Spring Harbor, N.Y., p 280–281 (1982).
McKinney et al. (1966) *Anal Biochem.* 14:421
Messing et al., *Third Cleveland Symposium on Macro Molecular and Recombinant DNA* Ed. Walton, A., (Elsevier, Amsterdam) (1981).
Mosqueda-Garcia, R., *Disorders of the Autonomic Nervous System* 25–59 (1995).
Needleman et al., *J. Mol. Biol.* 48:443 (1970).
Novak et al., *Stroke* 29:1876–1881 (1998).
Novak et al., *J Aut N Syst* 61:313–320 (1996).
Novi, A. M., *Anatomical Record* 160:123–141 (1968).
O'Sullivan et al. (1978) *FEBS Letters* 95:311
Pasternac et al., *Am J Med* 73:783–790 (1982).
*PCR. A Practical Approach*, ILR Press, Eds. McPherson, et al. (1992).
Pörzgen et al., *Biochimica et Biophysica Acta* 1398:365–370 (1998).
Puddu et al., *Am Heart J* 105:422–428 (1983).
Riley et al., *Clin Sci* 80:633–639 (1991).
Robinson et al., (1984) *Infect. Immun.* 46:361–366
Rosen et al., *Am J Med* 72:847–850 (1982).
Saiki et al., *Bio/Technology* 3:1008–1012 (1985).
Sambrook et al., *Molecular Cloning: A Laboratory Manual* (Cold Spring Harbor Press, Cold Spring Harbor, N.Y.) (1989).
Schmidt, R. D., *Clin. Chim. Acta.* 74:39–42 (1977).
Schondorf et al., *Neurology* 43:132–137 (1993).
Schondorf et al., *Am J Med Sc* 317:117–123 (1999).
Schwartz et al., eds., *Atlas of Protein Sequence and Structure*, National Biomedical Research Foundation, pp. 357–358 (1979).
Shannon et al., *Hypertension* 101–107 (1998).
Shannon et al., *Circulation* 98:1–336 (1998).
Shoup et al., *Clin Chem* 23:1268–1274 (1977).
Smith et al., *Adv. Appl. Math.* 2:482 (1981).
Stober et al., *American Journal of Medical Genetics* 67:523–532 (1996).
Streeten et al., *J Lab Clin Med* 111:326–335 (1988).
Streeten, D. H., *J Clin Invest* 86:1582–1588 (1990).
Streeten, D. H., *Orthostatic Disorders of the Circulation: Mechanisms, Manifestations, and Treatment* 111–125 (1987).
Tung et al., *J Pharm Exp Ther* 227:484–490 (1983).
U.S. Pat. No. 5,286,634
U.S. Pat. No. 5,399,346
U.S. Pat. No. 4,196,265
U.S. Pat. No. 4,458,066
U.S. Pat. No. 4,554,101
U.S. Pat. No. 4,683,195
U.S. Pat. No. 4,683,202
U.S. Pat. No. 4,736,866
U.S. Pat. No. 4,769,331
U.S. Pat. No. 4,965,188
U.S. Pat. No. 5,162,215
U.S. Pat. No. 5,279,833;
U.S. Pat. No. 5,625,125
U.S. Pat. No. 5,641,484
U.S. Pat. No. 5,489,742
U.S. Pat. No. 5,550,316
U.S. Pat. No. 5,573,933
U.S. Pat. No. 5,614,396
U.S. Pat. No. 5,741,957
U.S. Pat. No. 5,643,567
U.S. Pat. No. 5,646,008
U.S. Pat. No. 5,648,061
U.S. Pat. No. 5,651,964
Walsh et al., *J Clin Psychopharmacol* 12:163–168 (1992).
Wooley, C. F., *Circulation* 53:749–751 (1976).

It will be understood that various details of the invention can be changed without departing from the scope of the invention. Furthermore, the foregoing description is for the purpose of illustration only, and not for the purpose of limitation—the invention being defined by the claims.

What is claimed is:

1. A method of screening for susceptibility to sub-optimal norepinephrine (NE) transport resulting in decreased NE clearance in a subject, the method comprising:
   (a) obtaining a biological sample from the subject, wherein the biological sample comprises a nucleic acid sample; and
   (b) detecting a polymorphism of a NE transporter gene in the biological sample from the subject, wherein the polymorphism of the NE transporter gene comprises a G to C transversion within NE transporter exon 9 (nucleotides 129–257 of SEQ ID NO: 15), the presence of the polymorphism indicating the susceptibility of the subject to sub-optimal norepinephrine transport resulting in decreased NE clearance.

2. A method of screening for susceptibility to sub-optimal norepinephrine (NE) transport resulting in decreased NE clearance in a subject, the method comprising:
   (a) obtaining a biological sample from the subject, wherein the biological sample comprises a nucleic acid sample; and
   (b) detecting a polymorphism of a NE transporter gene in the biological sample from the subject, wherein the polymorphism of the NE transporter gene comprises a G to C transversion within NE transporter exon 9 (nucleotides 129–257 of SEQ ID NO: 15) and encodes a NE transporter polypeptide having a proline moiety at amino acid 457 of SEQ ID NO: 1, the presence of the polymorphism indicating the susceptibility of the subject to sub-optimal norepinephrine transport resulting in decreased NE clearance.

3. The method of claim 2, wherein the polymorphism is detected by amplifying a target nucleic acid in the nucleic acid sample from the subject using an amplification technique.

4. The method of claim 3, wherein the polymorphism is detected by amplifying a target nucleic acid in the nucleic acid sample from the subject using an oligonucleotide pair, wherein a first oligonucleotide of the pair hybridizes to a first portion of the NE transporter gene, wherein the first portion includes the polymorphism of the NE transporter gene, and wherein the second of the oligonucleotide pair hybridizes to a second portion of the NE transporter gene that is adjacent to the first portion.

5. A method of screening for susceptibility to sub-optimal norepinephrine (NE) transport resulting in decreased NE clearance in a subject, the method comprising:
   (a) obtaining a biological sample from the subject, wherein the biological sample comprises a nucleic acid sample; and
   (b) detecting a polymorphism of a NE transporter gene encoding an amino acid change in the biological sample from the subject, wherein the polymorphism of the NE transporter gene is detected by amplifying a target nucleic acid in the nucleic acid sample from the subject using an oligonucleotide pair, wherein a first oligonucleotide of the pair hybridizes to a first portion of the NE transporter gene including exon 9 (nucleotides 129–257 of SEQ ID NO: 15) and the polymorphism of the NE transporter gene, and wherein the second oligonucleotide of the pair hybridizes to a second portion of the NE transporter gene that is adjacent to the first portion, the presence of the polymorphism indicating the susceptibility of the subject to sub-optimal norepinephrine transport resulting in decreased NE clearance.

6. The method of claim 4, wherein the first and the second oligonucleotides each further comprise a detectable label, and wherein the label of the first oligonucleotide is distinguishable from the label of the second oligonucleotide.

7. The method of claim 6, wherein said label of said first oligonucleotide is a radiolabel, and wherein said label of said second oligonucleotide is a biotin label.

8. The method of claim 1 or 2, wherein the polymorphism is detected by sequencing a target nucleic acid in the nucleic acid sample from the subject.

9. The method of claim 8, wherein the sequencing comprises dideoxy sequencing.

10. A method of screening for susceptibility to sub-optimal norepinephrine (NE) transport resulting in decreased NE clearance in a subject, the method comprising:
(a) obtaining a biological sample from the subject, wherein the biological sample comprises a nucleic acid sample; and
(b) detecting a polymorphism of a NE transporter gene in the biological sample from the subject, wherein the polymorphism of the NE transporter gene is detected by contacting a target nucleic acid in the nucleic acid sample from the subject with a reagent that detects the presence of the NE transporter polymorphism and detecting the reagent, wherein the reagent detects a G to C transversion within NE transporter exon 9 (nucleotides 129–257 of SEQ ID NO: 15), the presence of the polymorphism indicating the susceptibility of the subject to sub-optimal norepinephrine transport resulting in decreased NE clearance.

11. A method of screening for susceptibility to sub-optimal norepinephrine (NE) transport resulting in decreased NE clearance in a subject, the method comprising:
(a) obtaining a biological sample from the subject, wherein the biological sample comprises a nucleic acid sample; and
(b) detecting a polymorphism of a NE transporter gene in the biological sample from the subject, wherein the polymorphism of the NE transporter gene is detected by contacting a target nucleic acid in the nucleic acid sample from the subject with a reagent that detects the presence of the NE transporter polymorphism and detecting the reagent, wherein the reagent is an oligonucleotide primer as set forth in SEQ ID NO:9 or SEQ ID NO:10, the presence of the polymorphism indicating the susceptibility of the subject to sub-optimal norepinephrine transport resulting in decreased NE clearance.

12. The method of claim 1, wherein the subject is a human subject.

13. The method of claim 2, wherein the susceptibility of the subject to sub-optimal NE transport is further characterized as susceptibility to orthostatic intolerance.

14. The method of claim 2, wherein the polymorphism results in a norepinephrine transporter comprising an amino acid sequence as set forth in SEQ ID NO: 4.

* * * * *